US010045914B2

(12) United States Patent
Yuyama et al.

(10) Patent No.: US 10,045,914 B2
(45) Date of Patent: Aug. 14, 2018

(54) MEDICINE DISPENSING APPARATUS, METHOD OF DISPENSING MEDICINES, MEDICINE DISPENSING PROGRAM AND STORAGE MEDIUM

(71) Applicant: YUYAMA MFG. CO., LTD., Toyonaka-shi, Osaka (JP)

(72) Inventors: Hiroyuki Yuyama, Toyonaka-shi (JP); Tooru Tanaka, Toyonaka-shi (JP); Tomohiro Sugimoto, Toyonaka-shi (JP); Tetsuya Terada, Toyonaka-shi (JP); Kento Miwa, Toyonaka-shi (JP)

(73) Assignee: YUYAMA MFG. CO., LTD., Toyonaka-shi (JP)

( * ) Notice: Subject to any disclaimer, the term of this patent is extended or adjusted under 35 U.S.C. 154(b) by 7 days.

(21) Appl. No.: 14/411,079

(22) PCT Filed: Dec. 3, 2013

(86) PCT No.: PCT/JP2013/082420
§ 371 (c)(1),
(2) Date: Dec. 23, 2014

(87) PCT Pub. No.: WO2014/112221
PCT Pub. Date: Jul. 24, 2014

(65) Prior Publication Data
US 2015/0190312 A1    Jul. 9, 2015

(30) Foreign Application Priority Data

Jan. 18, 2013  (JP) ................................. 2013-007722
Sep. 13, 2013  (JP) ................................. 2013-190091

(51) Int. Cl.
*A61J 7/00*     (2006.01)
*G07F 11/00*    (2006.01)
(Continued)

(52) U.S. Cl.
CPC ............... *A61J 7/0084* (2013.01); *A61J 7/02* (2013.01); *B65B 35/06* (2013.01);
(Continued)

(58) Field of Classification Search
None
See application file for complete search history.

(56) References Cited

U.S. PATENT DOCUMENTS 5,671,592 A * 9/1997 Yuyama .............. G07F 17/0092
                                                  53/168
8,855,811 B1 * 10/2014 Schultz ..................... A61J 7/02
                                                  700/236
(Continued)

FOREIGN PATENT DOCUMENTS

EP    1704844 A1    9/2006
JP    08-119202 A   5/1996
(Continued)

OTHER PUBLICATIONS

WIPO, Japanese International Search Authority, International Search Report dated Mar. 18, 2014 in International Patent Application No. PCT/JP2013/082420, with English translation, 5 pages.
(Continued)

*Primary Examiner* — Anna M Momper
*Assistant Examiner* — Stephen L Akridge
(74) *Attorney, Agent, or Firm* — Masuvalley & Partners

(57) ABSTRACT

Provided is a medicine dispensing apparatus including a plurality of medicine cassettes for respectively dispensing desired types of medicines. The medicine dispensing apparatus allocates medicine information on a medicine to be dispensed to one of the medicine cassettes when the medicine information is given. Then, the medicine dispensing apparatus drives the medicine cassette according to a predetermined driving condition corresponding to the medicine
(Continued)

information allocated to the medicine cassette to dispense the medicine from the medicine cassette. By using the medicine dispensing apparatus, it is possible to reduce a user work for dispensing the desired types of medicines.

13 Claims, 40 Drawing Sheets

(51) Int. Cl.
  *G07F 17/00* (2006.01)
  *G06F 19/00* (2018.01)
  *B65B 35/06* (2006.01)
  *A61J 7/02* (2006.01)

(52) U.S. Cl.
  CPC ........ *G06F 19/3462* (2013.01); *G07F 11/002* (2013.01); *G07F 17/0092* (2013.01)

(56) References Cited

U.S. PATENT DOCUMENTS

| | | | | |
|---|---|---|---|---|
| 2003/0065421 | A1* | 4/2003 | Didriksen | B65G 1/00 700/230 |
| 2005/0125097 | A1* | 6/2005 | Chudy | G06F 19/3462 700/236 |
| 2005/0162403 | A1* | 7/2005 | Kim | B65B 5/103 345/173 |
| 2005/0256609 | A1* | 11/2005 | Kim | G07F 9/026 700/236 |
| 2006/0058724 | A1* | 3/2006 | Handfield | A61J 7/0084 604/20 |
| 2007/0150092 | A1* | 6/2007 | Ohmura | G06F 19/3462 700/231 |
| 2007/0208595 | A1* | 9/2007 | Ohmura | G06F 19/3462 705/2 |
| 2008/0077274 | A1* | 3/2008 | Kim | G06F 19/3462 700/237 |
| 2008/0083769 | A1* | 4/2008 | Yuyama | G06Q 50/22 221/1 |
| 2008/0149656 | A1* | 6/2008 | Yuyama | G06Q 10/10 221/2 |
| 2009/0037020 | A1* | 2/2009 | Brown | G06F 19/3462 700/240 |
| 2010/0077707 | A1* | 4/2010 | Kondo | B65B 5/103 53/493 |
| 2010/0121486 | A1* | 5/2010 | Yuyama | G07F 11/44 700/227 |
| 2010/0287880 | A1* | 11/2010 | Yasunaga | A61J 7/0084 53/64 |
| 2011/0170655 | A1* | 7/2011 | Yuyama | G07F 11/66 377/6 |
| 2012/0024423 | A1* | 2/2012 | Imai | B65B 43/42 141/391 |
| 2012/0190342 | A1* | 7/2012 | Seibert | G07D 11/0063 455/411 |
| 2012/0216485 | A1* | 8/2012 | Amano | G07F 11/44 53/64 |
| 2012/0324829 | A1* | 12/2012 | Omura | B65B 1/28 53/147 |
| 2013/0284755 | A1* | 10/2013 | Yuyama | A61J 7/02 221/13 |

FOREIGN PATENT DOCUMENTS

| | | |
|---|---|---|
| JP | H10-19902 A | 5/1998 |
| JP | H11314601 A | 11/1999 |
| JP | 2000-354620 A | 12/2000 |
| JP | 2001-087353 A | 4/2001 |
| JP | 2001-335002 A | 12/2001 |
| JP | 2006-051178 A | 2/2006 |
| JP | 2007-246114 A | 9/2007 |
| JP | 2010-082052 A | 4/2010 |
| JP | 2011-104077 A | 6/2011 |
| JP | 2013-013777 A | 1/2013 |
| WO | 2007/119303 A1 | 10/2007 |
| WO | WO2011/102491 A1 | 8/2011 |
| WO | 2012/099189 A1 | 7/2012 |

OTHER PUBLICATIONS

European Patent Office, Extended European Search Report dated Sep. 3, 2015 in European Patent Application No. EP13871890.3-1955/2853252, 12 pages.

Japan Patent Office, Notice of Opposition dated May 16, 2017 in Japanese Patent Application No. 2014-538940, total 55 pages.

* cited by examiner

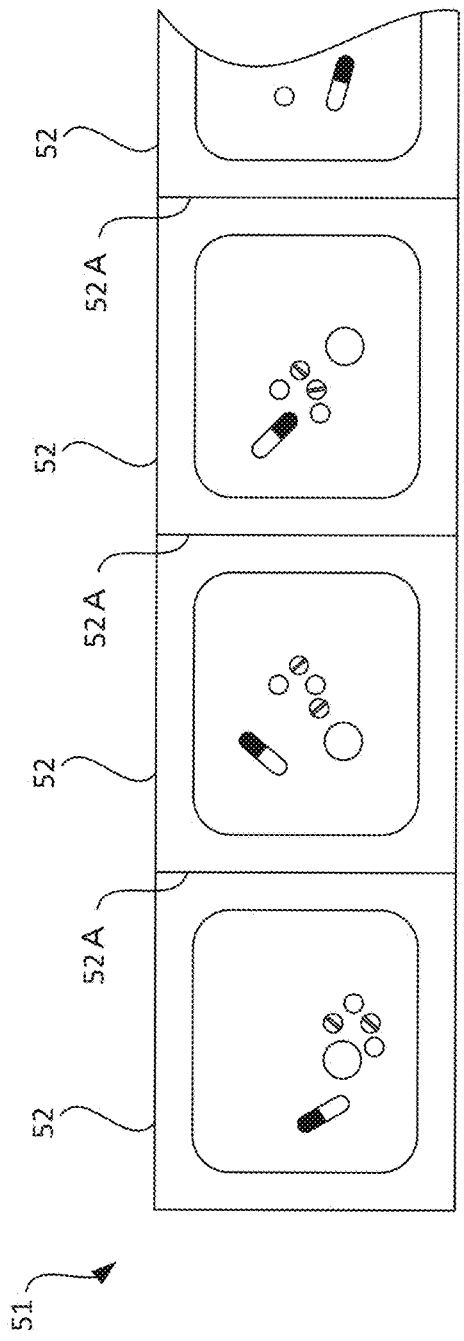

FIG. 10

| Medicine ID | Driving condition | | | |
|---|---|---|---|---|
| | Height of dispensing path | Width of dispensing path | Dispensing speed | Reverse rotation control |
| M 1 | h 1 1 [mm] | w 1 1 [mm] | v 1 1 [Tablets / min] | ON |
| M 2 | h 1 2 [mm] | w 1 2 [mm] | v 1 2 [Tablets / min] | OFF |
| M 3 | h 1 3 [mm] | w 1 3 [mm] | v 1 3 [Tablets / min] | OFF |
| M 4 | h 1 4 [mm] | w 1 4 [mm] | v 1 4 [Tablets / min] | ON |
| . . . | . . . | . . . | . . . | . . . |

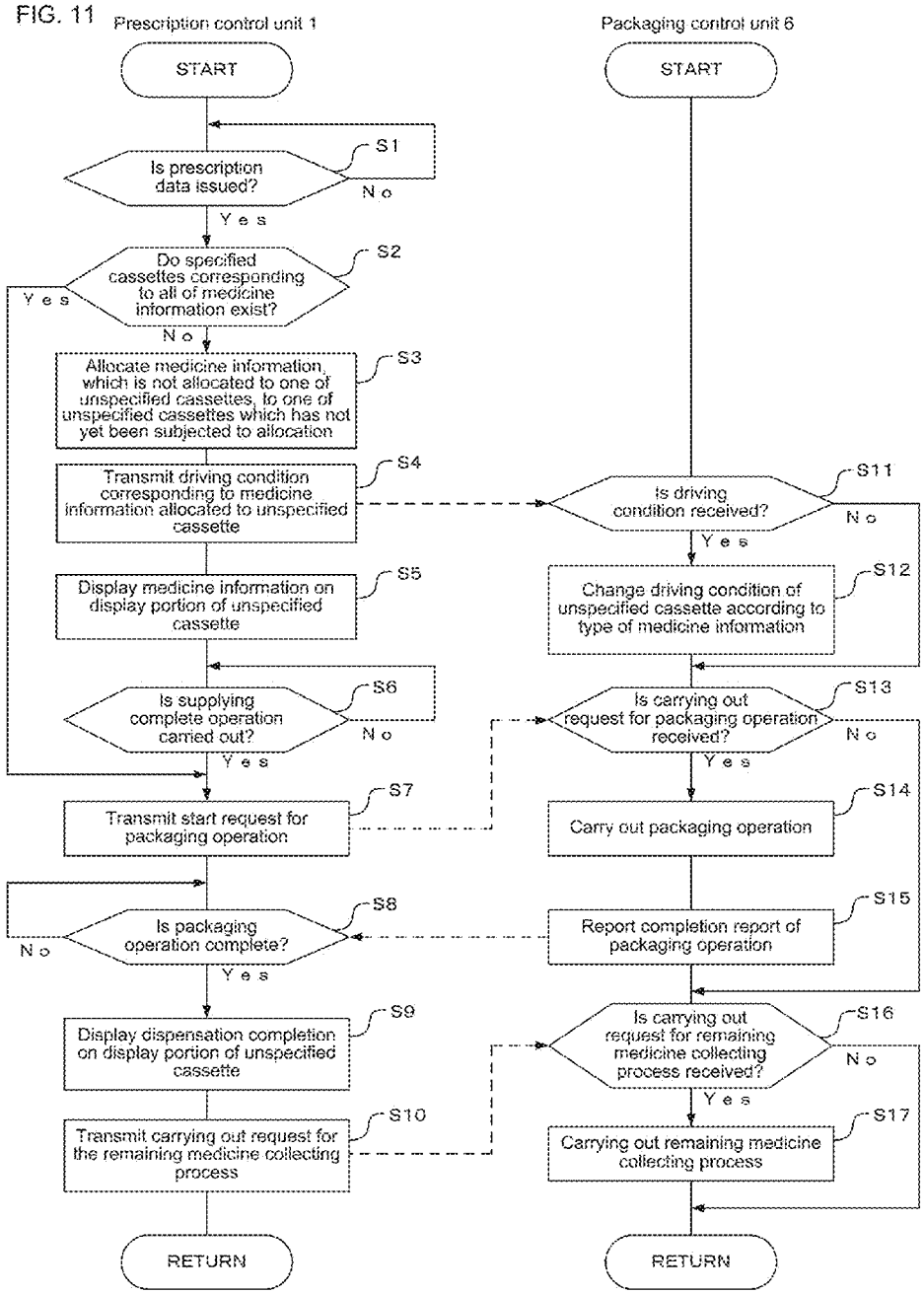

(C)

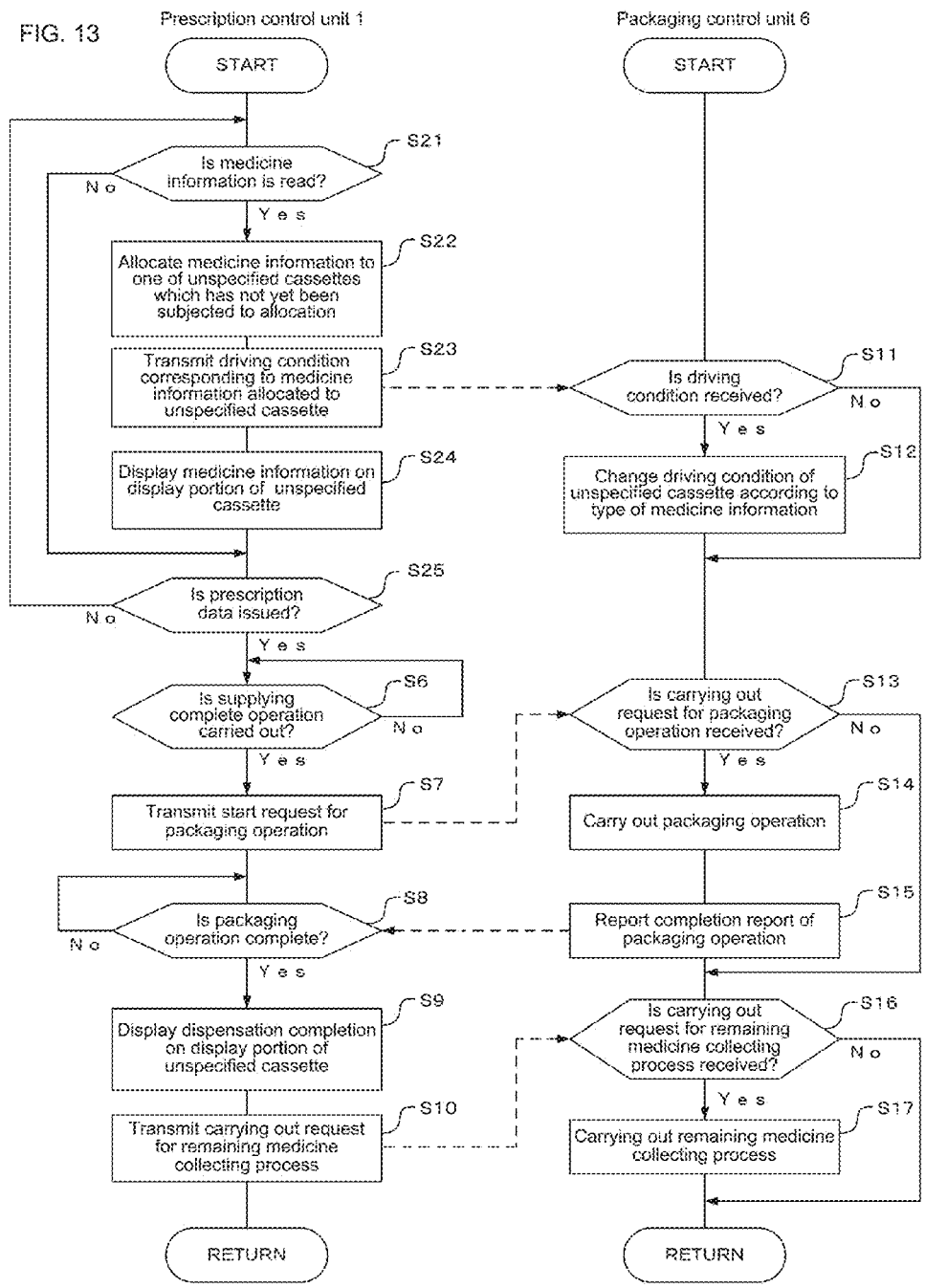

FIG. 18A

| Unspecified cassette | Medicine ID |
|---|---|
| C 1 | R P 1 - M 1 |
| C 2 | R P 1 - M 2 |
| C 3 | R P 1 - M 3 |
| C 4 | - |

| Unspecified cassette | Medicine ID |
|---|---|
| C 1 | R P 1 - M 1 |
| C 2 | R P 1 - M 2 |
| C 3 | R P 1 - M 3 |
| C 4 | R P 2 - M 4 |

| Unspecified cassette | Medicine ID |
|---|---|
| C 1 | - |
| C 2 | - |
| C 3 | - |
| C 4 | R P 2 - M 4 |

| Unspecified cassette | Medicine ID |
|---|---|
| C 1 | R P 2 - M 5 |
| C 2 | - |
| C 3 | - |
| C 4 | R P 2 - M 4 |

| Unspecified cassette | Medicine ID |
|---|---|
| C 1 | R P 1 - M 1 |
| C 2 | R P 1 - M 2 |
| C 3 | R P 1 - M 3 |
| C 4 | - |

| Unspecified cassette | Medicine ID |
|---|---|
| C 1 | R P 1 - M 1 |
| C 2 | R P 1 - M 2 |
| C 3 | R P 1 - M 3 |
| C 4 | R P 2 - M 5 |

| Unspecified cassette | Medicine ID |
|---|---|
| C 1 | - |
| C 2 | - |
| C 3 | - |
| C 4 | R P 2 - M 5 |

| Unspecified cassette | Medicine ID |
|---|---|
| C 1 | R P 2 - M 4 |
| C 2 | - |
| C 3 | - |
| C 4 | R P 2 - M 5 |

| Unspecified cassette | Medicine ID |
|---|---|
| C 1 | R P 1 - M 1 |
| C 2 | R P 1 - M 2 |
| C 3 | R P 1 - M 3 |
| C 4 | - |

| Unspecified cassette | Medicine ID |
|---|---|
| C 1 | R P 1 - M 1 |
| C 2 | R P 1 - M 2 |
| C 3 | R P 1 - M 3 |
| C 4 | R P 2 - M 4 |

| Unspecified cassette | Medicine ID |
|---|---|
| C 1 | - |
| C 2 | - |
| C 3 | - |
| C 4 | R P 2 - M 4 |

| Unspecified cassette | Medicine ID |
|---|---|
| C 1 | - |
| C 2 | R P 2 - M 2 |
| C 3 | - |
| C 4 | R P 2 - M 4 |

| Unspecified cassette | Medicine ID |
|---|---|
| C 1 | R P 1 - M 1 |
| C 2 | R P 1 - M 2 |
| C 3 | R P 1 - M 3 |
| C 4 | - |

FIG. 21B

| Unspecified cassette | Medicine ID |
|---|---|
| C 1 | R P 1 - M 1 |
| C 2 | R P 1 - M 2 |
| C 3 | R P 1 - M 3 |
| C 4 | R P 2 - M 2 |

FIG. 21C

| Unspecified cassette | Medicine ID |
|---|---|
| C 1 | - |
| C 2 | - |
| C 3 | - |
| C 4 | R P 2 - M 2 |

FIG. 21D

| Unspecified cassette | Medicine ID |
|---|---|
| C 1 | R P 2 - M 4 |
| C 2 | - |
| C 3 | - |
| C 4 | R P 2 - M 2 |

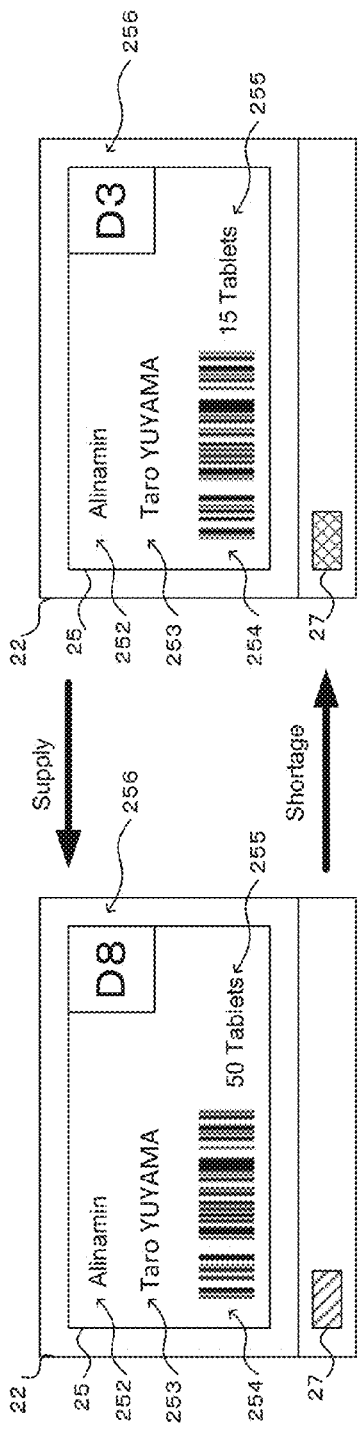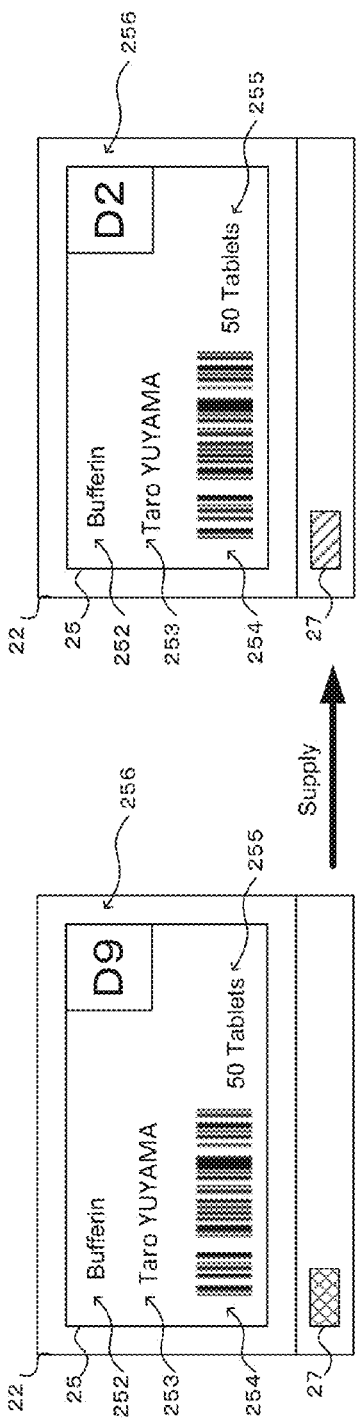

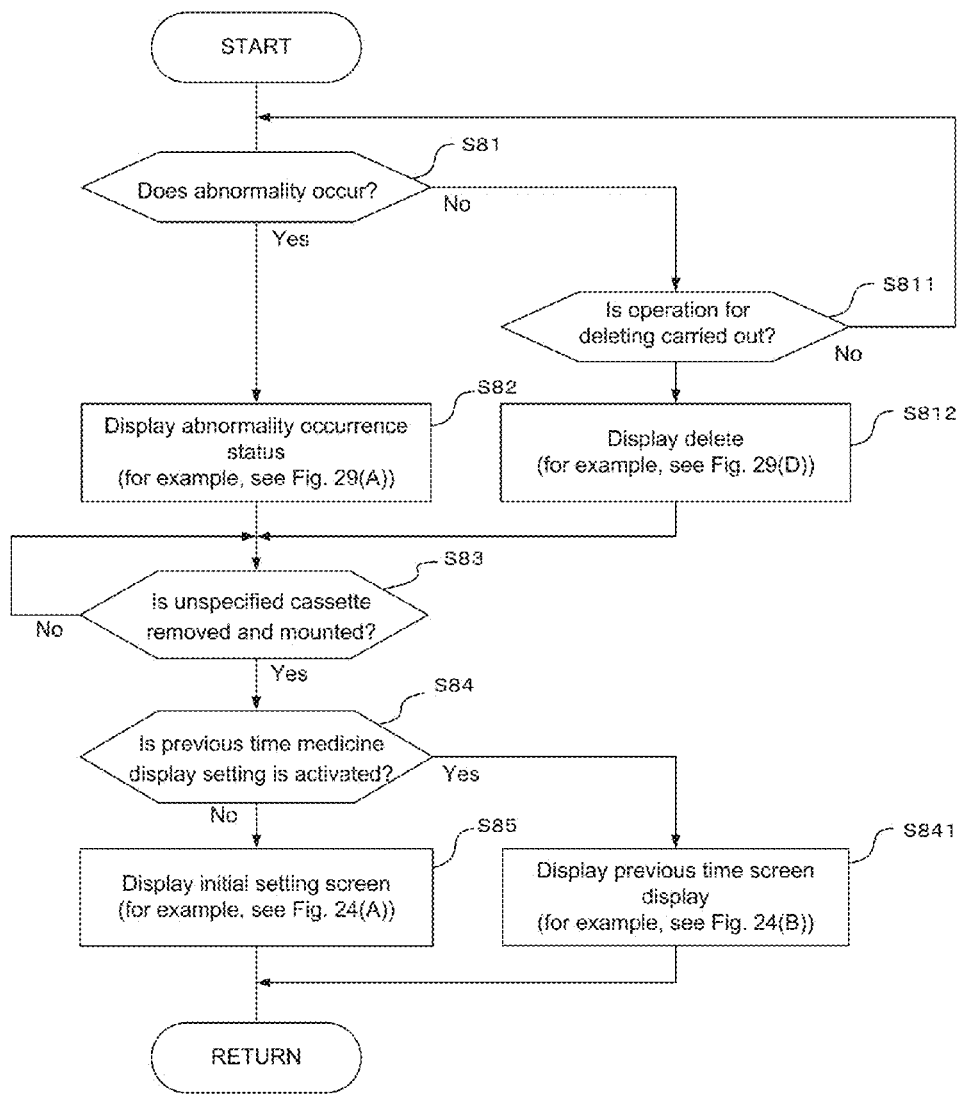

FIG. 30

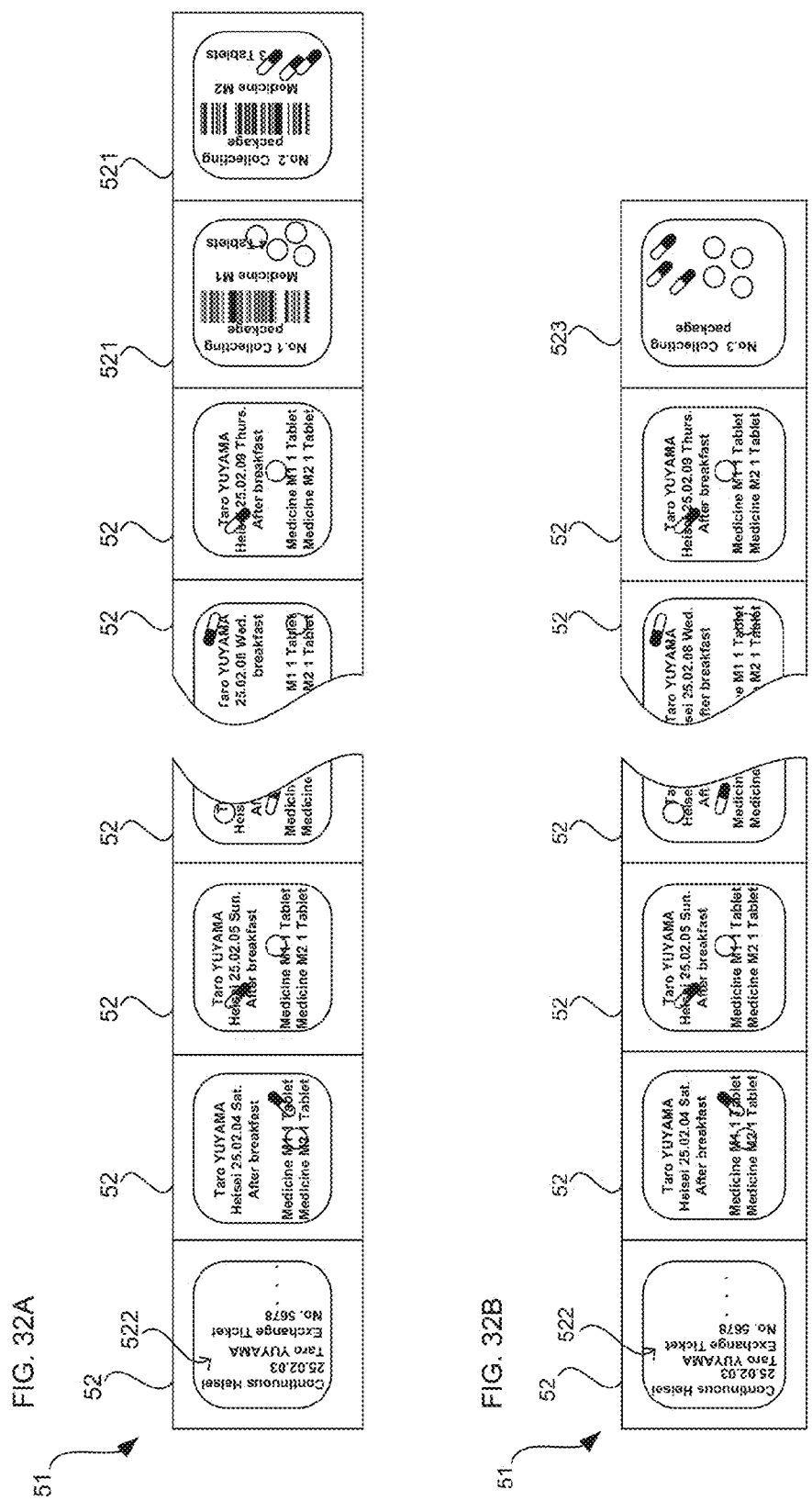

123

| Collecting Number | Medicine Code | Medicine Name |
|---|---|---|
| 1 | MED10 | Medicine M1 |
| 2 | MED20 | Medicine M2 |
| 3 | MED10 | Medicine M1 |

| Collection Number | Medicine Code | Medicine Name | Number of medicines |
|---|---|---|---|
| 1 | MED10 | Medicine M1 | 4 |
| 2 | MED20 | Medicine M2 | 4 |
| 3 | MED10 | Medicine M1 | 3 |
| 4 | MED10 | Medicine M1 | 5 |

FIG. 34B

MEDICINE DISPENSING APPARATUS, METHOD OF DISPENSING MEDICINES, MEDICINE DISPENSING PROGRAM AND STORAGE MEDIUM

RELATED APPLICATIONS

This application is the U.S. National Phase of and claims priority to International Patent Application No. PCT/JP2013/082420, International Filing Date Dec. 3, 2013, entitled Drug Delivery Device, Drug Delivery Method, Drug Delivery Program, And Recording Medium, which claims benefit of Japanese Application No. JP2013-007722, filed Jan. 18, 2013, and Japanese Application No. JP2013-190091 filed Sep. 13, 2013, all of which are incorporated herein by reference in their entireties.

TECHNICAL FIELD

The present invention relates to a medicine dispensing apparatus for automatically dispensing medicines from a plurality of medicine cassettes.

BACKGROUND ART

From before, there has been known a medicine dispensing apparatus which includes a plurality of tablet cassettes for containing predetermined types of tablets and is configured to automatically dispense the tablets contained in the tablet cassettes on the basis of prescription data (for example, see patent document 1). In such a type of medicine dispensing apparatus, since types of tablets which can be dispensed from the tablet dispensing apparatus are respectively allocated to the tablet cassettes in advance, a large number of tablet cassettes are required for allowing the medicine dispensing apparatus to deal with a wide various types of tablets. This results in upsizing of the medicine dispensing apparatus.

On the other hand, there has been also known a medicine dispensing apparatus which includes a manual packaging unit for dispensing tablets supplied into a plurality of boxes arranged in a matrix pattern, in units of the boxes (for example, see patent document 1). Since such a type of medicine dispensing apparatus can automatically dispense desired types of tablets in units of boxes with the manual packaging unit, it is possible to deal with a wide various types of tablets without a large number of tablet cassettes.

RELATED ART DOCUMENT

Patent Document

Patent document 1: JP 2011-104077A

SUMMARY OF THE INVENTION

Problems to be Solved by the Invention

However, there is a problem in that it is a complicated work for a user to supply the tablets into the boxes of the manual packaging unit and this work becomes a big burden on the user. Especially, it is a significantly complicated work for the user to supply various types of medicines having different administration times into the boxes corresponding to the different administration times. Further, since the user manually supplies the tablets into each of the boxes, there is a risk that prescription errors occur due to human errors.

Accordingly, it is an object of the present invention to provide a medicine dispensing apparatus, a method of dispensing medicines, a medicine dispensing program and a computer-readable storage medium storing the medicine dispensing program which can reduce a user work for dispensing desired types of medicines.

Means of Solving the Problems

A medicine dispensing apparatus according to the present invention includes a plurality of medicine cassettes, allocating means and driving control means. The medicine cassettes can respectively dispense desired types of medicines. The allocating means allocates medicine information on a medicine to be dispensed to one of the medicine cassettes when the medicine information is given. The driving control means drives the medicine cassette according to a predetermined driving condition corresponding to the medicine information allocated to the medicine cassette by the allocating means to dispense the medicine from the medicine cassette. For example, the medicine is a tablet.

A method of dispensing medicines with a medicine dispensing apparatus including a plurality of medicine cassettes for respectively dispensing desired types of medicines according to the present invention includes allocating medicine information on a medicine to be dispensed to one of the medicine cassettes when the medicine information is given and driving the medicine cassette according to a driving condition predetermined so as to correspond to the medicine information allocated in the allocating, to dispense the medicine from the medicine cassette.

A medicine dispensing program according to the present invention allows a computer to execute a method of dispensing a medicine. The method includes allocating medicine information on a medicine to be dispensed to one of a plurality of medicine cassettes for respectively dispensing desired types of medicines when the medicine information is given and driving the medicine cassette according to a driving condition predetermined so as to corresponding to the medicine information allocated in the allocating, to dispense the medicine from the medicine cassette.

A storage medium according to the present invention is a computer-readable storage medium storing the medicine dispensing program described above.

Effect of the Invention

According to the present invention, it is possible to reduce a user work for dispensing desired types of medicines.

BRIEF DESCRIPTION OF THE DRAWINGS

FIG. 8 is a view showing one example of a result of packaging tablets.

FIG. 9 is a view showing one example of allocation information.

FIG. 10 is a view showing one example of driving correspondence information.

FIG. 11 is a flow chart for explaining one example of each of procedures for a medicine dispensing process and a packaging control process.

FIG. 13 is a flow chart for explaining another example of the procedure for the medicine dispensing process.

FIG. 18 is a view for illustrating a transition of the allocation information at the time of carrying out the subsequent prescription allocating process.

FIG. 19 is a view for illustrating another transition of the allocation information at the time of carrying out the subsequent prescription allocating process.

FIG. 20 is a view for illustrating other transition of the allocation information at the time of carrying out the subsequent prescription allocating process.

FIG. 21 is a view for illustrating the other transition of the allocation information at the time of carrying out the subsequent prescription allocating process.

FIG. 27 is a view showing a display example at the time of carrying out the continuous use display process.

FIG. 28 is a flow chart for explaining one example of a procedure for an exceptional display process.

FIG. 30 is a view showing a transition example of a state of the unspecified cassette and a display state of the display portion.

FIG. 32 is a view showing one example of a charta sheet to be dispensed from the packaging unit.

FIG. 34 is a view showing one example of a result of carrying out the remaining medicine reuse process.

DETAILED DESCRIPTION OF THE PREFERRED EMBODIMENTS

Hereinafter, description will be given to embodiments of the present invention with reference to the accompanying drawings for facilitating the understanding of the present invention.

First Embodiment

First, description will be given to a schematic configuration of a medicine dispensing apparatus 100 according to a first embodiment of the present invention with reference to FIGS. 1 and 2.

Figure 1:
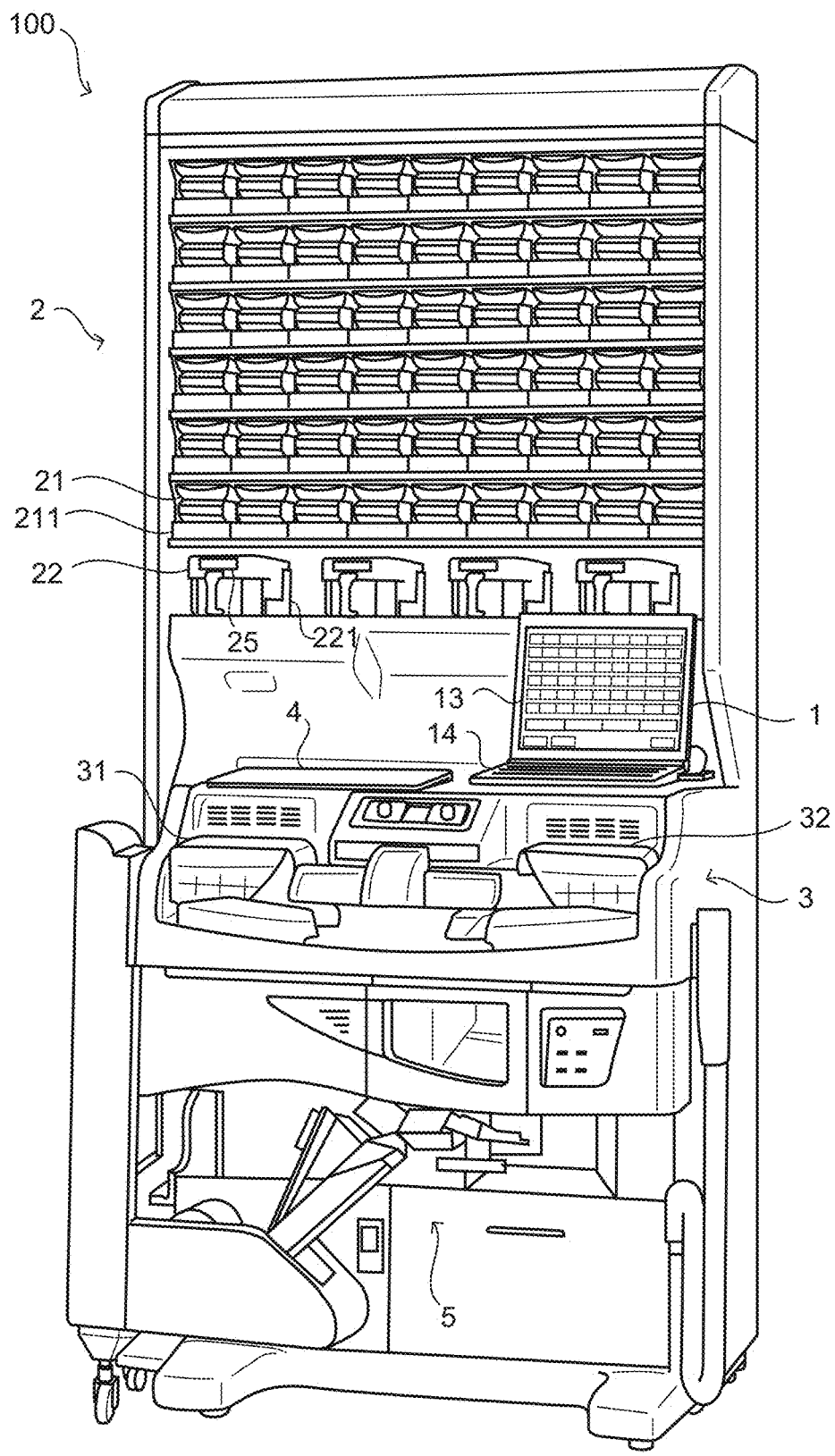
FIG. 1 is an external view showing a medicine dispensing apparatus according to an embodiment of the present invention.
Figure 2:
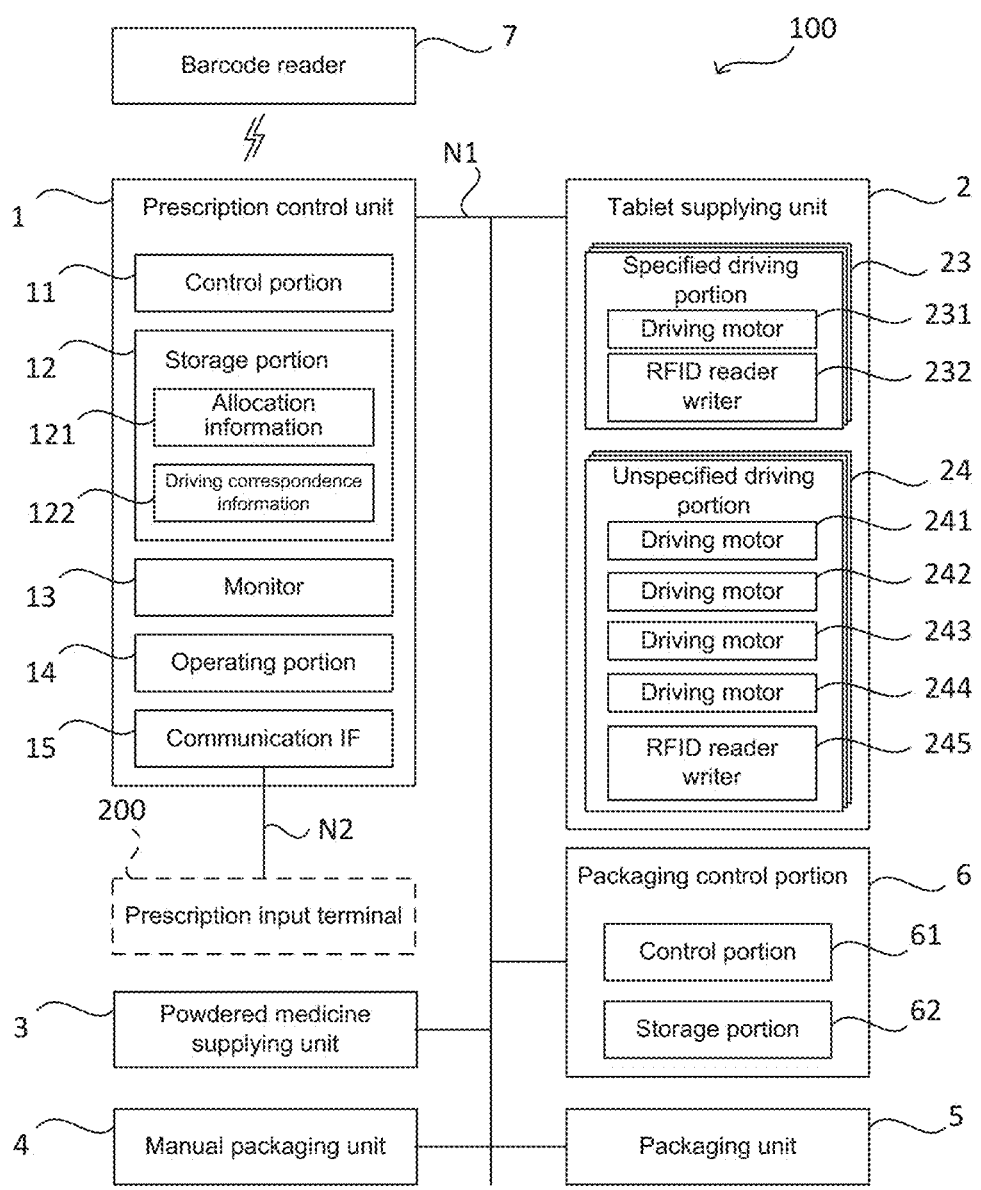
FIG. 2 is a block diagram showing a system configuration of the medicine dispensing apparatus according to the embodiment of the present invention.

As shown in FIGS. 1 and 2, the medicine dispensing apparatus 100 includes a prescription control unit 1, a tablet supplying unit 2, a powdered medicine supplying unit 3, a manual packaging unit 4, a packaging unit 5, a packaging control unit 6, a barcode reader 7 and the like. The prescription control unit 1, the tablet supplying unit 2, the powdered medicine supplying unit 3, the manual packaging unit 4, the packaging unit 5 and the packaging control unit 6 are mutually connected by an internal bus N1. Further, the prescription control unit 1 and the barcode reader 7 can carry out wireless communication according to various communication standards such as a wireless LAN and Bluetooth (registered trade-mark). The medicine dispensing apparatus 100 is controlled by the prescription control unit 1 and the packaging control unit 6, and causes the packaging unit 5 to package tablets and powdered medicine supplied from the tablet supplying unit 2, the powdered medicine supplying unit 3 or the manual packaging unit 4, in units of packages according to various information such as an administration time, and dispenses the packaged tablets and powdered medicine.

Although the medicine dispensing apparatus 100 includes both the powdered medicine supplying unit 3 and the manual packaging unit 4 in this embodiment, another configuration in which the medicine dispensing apparatus 100 includes only one of the powdered medicine supplying unit 3 and the manual packaging unit 4 or does not include the powdered medicine supplying unit 3 and the manual packaging unit 4 may be considered as another embodiment.

[Tablet Supplying Unit 2]

The tablet supplying unit 2 includes a plurality of specified cassettes 21 (corresponding to a plurality of specified medicine cassettes) which can respectively dispense predetermined specific types of tablets one by one (unit amount) and a plurality of unspecified cassettes 22 (corresponding to a plurality of medicine cassettes) which can respectively dispense desired types of medicines one by one (unit amount). Specifically, in the example shown in FIG. 1, the tablet supplying unit 2 includes 54 specified cassettes 21 in total arranged in a matrix of 6 rows and 9 columns and 4 unspecified cassettes in total arranged in a one row. The tablet which can be dispensed from each of the specified cassettes and each of the unspecified cassettes includes various solid medicines having various shapes such as a small round-shaped medicine, a spherical-shaped medicine and a capsular medicine.

Each of the specified cassettes 21 is configured to be detachably mounted on each of mounting portions 211 provided in the tablet supplying unit 2. Each of the mounting portions 211 includes a specified driving portion 23 for individually driving the corresponding specified cassette 21. Each of the specified driving portions 23 includes a driving motor 231 for supplying driving force to a driving mechanism of the corresponding specified cassette 21 and an RFID (Radio Frequency Identification) reader writer 232 which is information reading means for reading/writing information from and to an RFID tag (not shown in the drawings) provided at the corresponding specified cassette 21 with RFID wireless communication technique.

Positions where the RFID tag (not shown in the drawings) and the RFID reader writer 232 are provided may be relatively set so that the RFID reader writer 232 can read/write information from and to the RFID tag (not shown in the drawings) in a state where the specified cassette 21 is mounted on the mounting portion 211.

The RFID tag (not shown in the drawings) is a non-volatile storage medium for storing some information such as cassette identification information for identifying each of the specified cassettes 21. The cassette identification information is written to the RFID tag by the prescription control unit 1 at the time of an initial setting of the medicine dispensing apparatus 100 or the like. In this regard, another configuration having no specified cassettes 21 and having only the plurality of unspecified cassettes 22 may be considered as another embodiment.

Each of the unspecified cassettes 22 is configured to be detachably mounted on each of mounting portions 221 provided in the tablet supplying unit 2. Another configuration in which each of the unspecified cassettes 22 is configured to be mounted on each of the mounting portions 221 in a drawable state may be considered as another embodiment. Each of the mounting portions 221 includes an unspecified driving portion 24 for individually driving the corresponding unspecified cassette 22. Each of the unspecified driving portions 24 includes a plurality of driving motors 241 to 244 (one example of driving means) for supplying driving force to a driving mechanism of the corresponding unspecified cassette 22 and an RFID reader writer 245 which is information reading means for reading/writing information from and to an RFID tag 26 (see FIG. 6) provided at the corresponding unspecified cassette 22 with the RFID wireless communication technique.

Positions where the RFID tag 26 and the RFID reader writer 245 are provided may be relatively set so that the RFID reader writer 245 can read/write information from and to the RFID tag 26 in a state where the unspecified cassette 22 is mounted on the mounting portion 221.

The RFID tag 26 is a non-volatile storage medium for storing some information such as cassette identification information for identifying each of the unspecified cassettes 22 and medicine information allocated to each of the unspecified cassettes 22 in a medicine dispensing process described below (see FIG. 11).

The medicine information is information for identifying a type of tablet (medicine). Examples of the medicine information include a medicine name, a medicine ID, a medicine code, a JAN code, an RSS code and a QR code (registered trade-mark). Each of the JAN code and the RSS code is numerical numbers or textual information represented by a one-dimensional code (barcode). The QR code (registered trade-mark) is numerical numbers or textual information represented by a two-dimensional code.

The number of the unspecified cassettes 22 may be different from the number of the mounting portions 221. For example, it is possible to take a configuration in which a user can select an arbitrary unspecified cassette 22 from unspecified cassettes 22 which exceed in number the mounting portions 221 and mount the selected unspecified cassette 22 on one of the mounting portions 221. Especially, it is possible to take another configuration in which the tablet supplying unit 2 includes the plurality of unspecified cassettes 22 which can be respectively mounted on the corresponding mounting portions 221. This discussion regarding the unspecified cassettes 22 and the mounting portions 221 can be applied to the specified cassettes 21 and the mounting portions 211 thereof.

[Specified Cassette 21]

Figure 3:
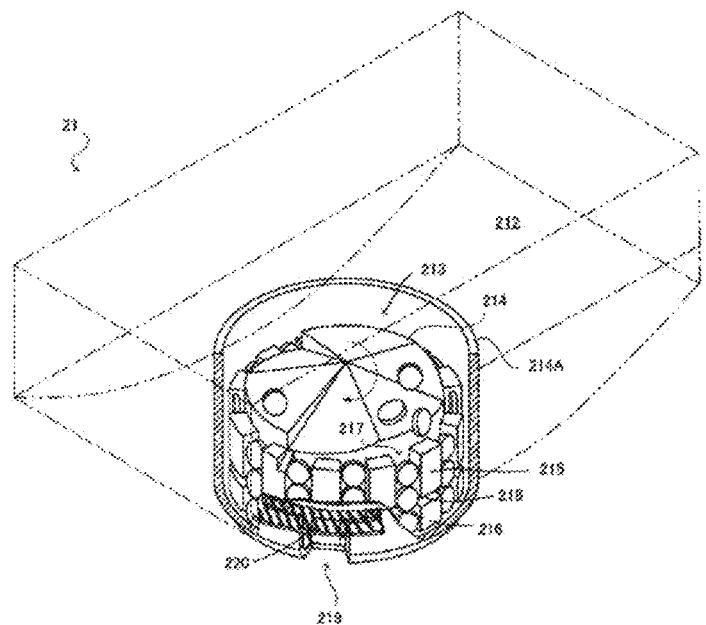
FIG. 3 is a perspective view for illustrating a structure of an specified cassette.

Here, description will be given to one example of the specified cassette 21 with reference to FIG. 3. It is noted that a structure of the specified cassette 21 described below is merely one example, and thus it is possible to take any other structure as the structure of the specified cassette 21 as long as it has the same function. FIG. 3 is a view showing the structure of the specified cassette 21 with a cover member, which covers a top portion of the specified cassette 21, being omitted.

Since types of tablets respectively contained in the specified cassettes 21 are predetermined, medicine information on the tablet to be contained in each of the specified cassettes 21 is written on a front surface of the specified cassette 21 in advance.

As shown in FIG. 3, the specified cassette 21 includes a tablet containing portion 212 for containing a plurality of tablets and a tablet discharging portion 213 for discharging the tablets contained in the tablet containing portion 212 one by one. The tablet discharging portion 213 is provided in a concave portion formed on a substantially central portion of the tablet containing portion 212. The tablets in the tablet containing portion 212 are downwardly conveyed toward the tablet discharging portion 213 in turn.

The tablet discharging portion 213 includes a rotor rotatably supported by a housing of the specified cassette 21 and an inner wall 214A surrounding an outer periphery of the rotor 214. The rotor 214 is connected to the driving motor 231 of the specified driving portion 23 through a drive transmission system such as various gears (not shown in the drawings) when the specified cassette 21 is mounted on the mounting portion 211. Further, ribs 215 and ribs 216 are formed on an outer peripheral surface of the rotor 214 at predetermined intervals. Thus, gaps 217 surrounded by the ribs 215, the ribs 216 and the inner wall 214A are intermittently formed on the outer periphery of the rotor 214. A width of each gap 217 is set depending on the predetermined type of tablet to be contained in the specified cassette 21, thus the width of each gap 217 corresponds to a width of one tablet.

Gaps 218 are formed between the ribs 215 and the ribs 216 so as to surround the outer peripheral surface of the rotor 214. A height position of an upper end of each of the ribs 215 and the ribs 216 is set depending on the predetermined type of tablet to be contained in the specified cassette 21. Specifically, the height position of the upper end of each of the ribs 215 is set so that a total height of the rib 215, the gap 218 and the rib 216 corresponds to a height of three tablets as shown in FIG. 3. Thus, three of the tablets can be putted in each of the gaps 217 of the rotor 213. Further, a height position of an upper end of each of the ribs 216 is set so that a height of each of the ribs 216 corresponds to a height of one tablet.

On the other hand, a discharging port 219 for discharging the tablet from the rotor 214 is formed on the inner wall 214A. Further, a partition plate 220 inserted into the gaps 218 is provided at the discharging port 219. This partition plate 220 makes it possible to prevent two of the three tablets putted in each of the gaps 217 from dropping and allows the lowest one of the three tablets to be discharged. Thus, in the specified cassette 21, the rotor 214 is driven by the driving motor 231 to discharge the tablets contained in the tablet containing portion 212 one by one (in a unit of one tablet).

[Unspecified Cassette 22]

Next, description will be given to one example of the unspecified cassette 22 with reference to FIGS. 4 to 7. It is noted that a structure of the unspecified cassette 22 described below is merely one example, and thus it is possible to take any other structure as the structure of the unspecified cassette 22 as long as it has the same function. For example, other examples of the unspecified cassette 22 are disclosed in JP 2010-535683A and JP 2010-115493A.

Figure 4:
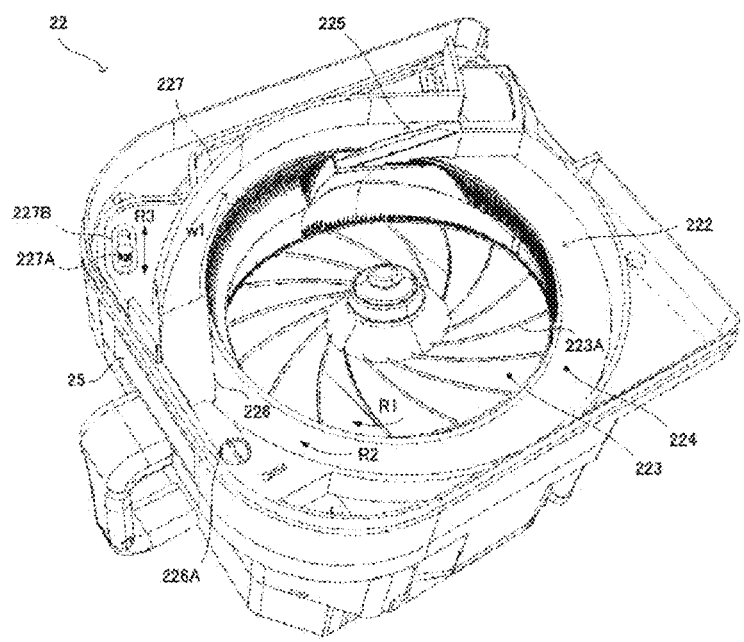
FIG. 4 is a perspective view for illustrating a structure of an unspecified cassette.
Figure 5:
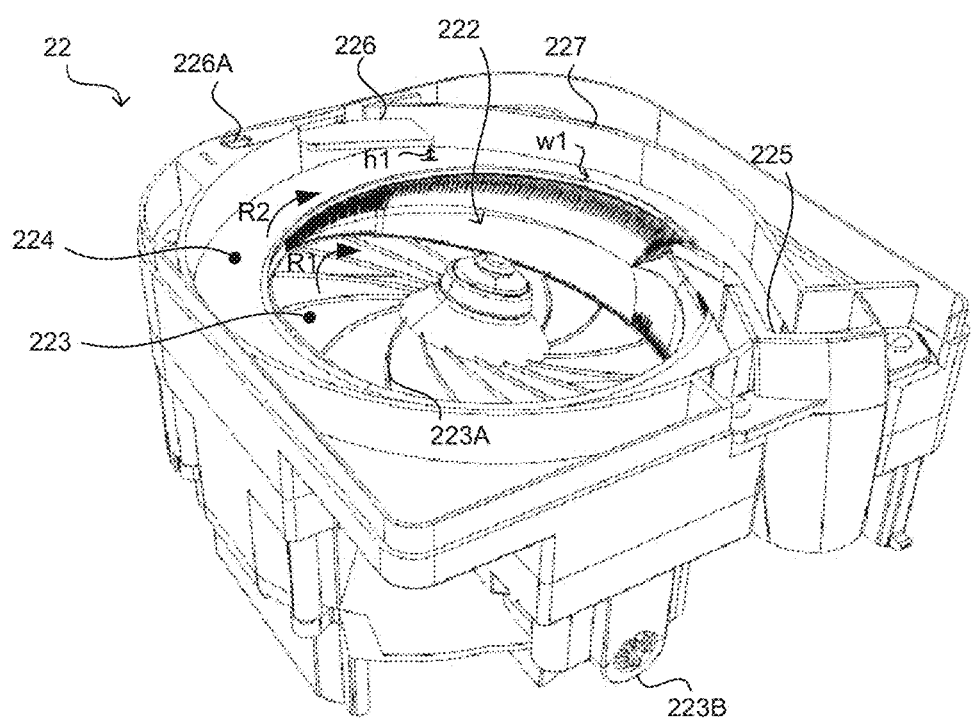
FIG. 5 is another perspective view for illustrating the structure of the unspecified cassette.
Figure 6:
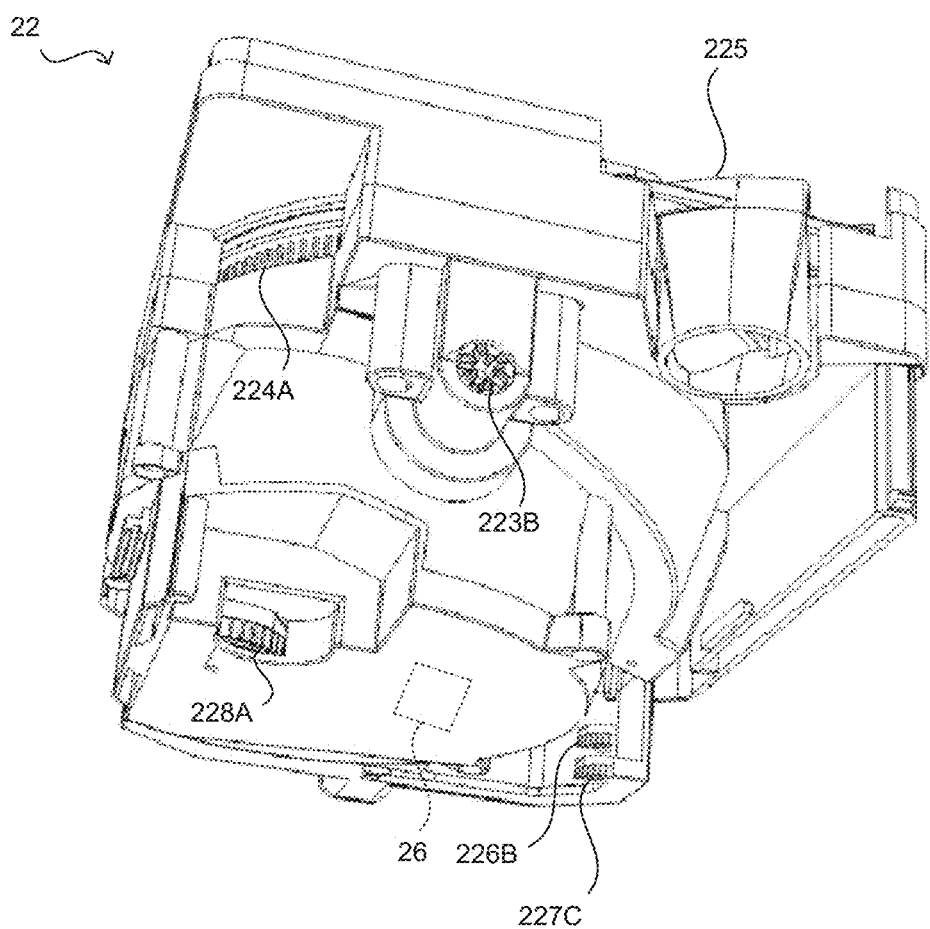
FIG. 6 is another perspective view for illustrating the structure of the unspecified cassette.

As shown in FIGS. 4 to 6, the unspecified cassette 22 includes a tablet containing portion 222 for containing a lot of tablets, a first rotating body 223 and a second rotating body 224. The first rotating body 223 and the second rotating body 224 are used for dispensing the tablets from the tablet containing portion 222. In this case, the first rotating body 223 and the second rotating body 224 are examples of dispensing means and a driving mechanism. Each of FIGS. 4 to 6 is a view showing the unspecified cassette 22 with a cover member, which covers a top portion of the unspecified cassette 22, being omitted. The unspecified cassette 22 may take any other configuration as long as it can dispense the tablets in a predetermined unit amount. For example, the unspecified cassette 22 may take another configuration which can dispense the tablets not in a unit of one tablet but in units of some tablets.

The first rotating body 223 is a disk-shaped member forming a bottom surface of the tablet containing portion 222. An rotational axis of the first rotating body 223 inclines with respect to a vertical direction at a predetermined specific angle, and an upper surface of the first rotating body 223 inclines with respect to a horizontal plane at the predetermined specific angle. Further, radial ribs 223A are formed on the upper surface of the first rotating body 223 at specific intervals. The first rotating body 223 is rotatably supported by the housing of the unspecified cassette 22 and connected to a driving gear 223B shown in FIGS. 5 and 6.

Figure 7:
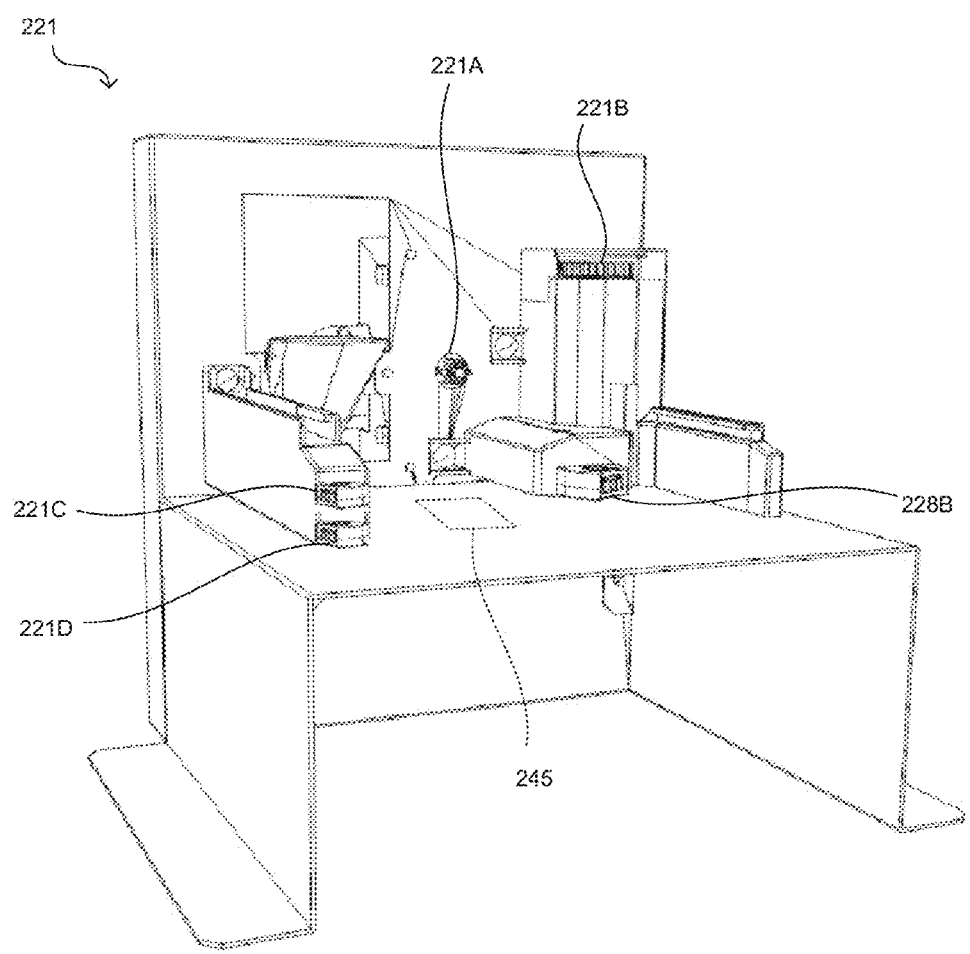
FIG. 7 is a perspective view for illustrating a structure of a mounting portion of the unspecified cassette.

The second rotating body 224 is an annular hollow member arranged around the first rotating body 223 in planar view thereof. The second rotating body 224 may be considered as one example of a conveying member for conveying the tablets in the tablet containing portion 22 toward a dispensing port 225 to dispense the tablets. An upper end portion of the first rotating body 223 is positioned on the same horizontal plane as the second rotating body 224. Further, the second rotating body 224 is rotatably supported by the housing of the unspecified cassette 22 and a driving gear 224A is formed on an outer peripheral surface of the second rotating body 224 as shown in FIG. 6. On the other hand, as shown in FIG. 7, the mounting portion 221 includes a driving gear 221A engaged with the driving gear 223B of the first rotating body 223 when the unspecified cassette 22 is mounted on the mounting portion 221 and a driving gear 221B engaged with the driving gear 224A of the second rotating body 224 when the unspecified cassette 22 is mounted on the mounting portion 221. The driving gear 221A is connected to the driving motor 241 of the unspecified driving portion 24. The driving gear 221B is connected to the driving motor 242 of the unspecified driving portion 24.

Furthermore, as shown in FIGS. 4 and 5, the unspecified cassette 22 includes a height restriction member 226 and a width restriction member 227 which are arranged on a dispensing path on which the tablets are conveyed toward the dispensing port 225 by means of the second rotating body 224.

The height restriction member 226 restricts a size in a height direction of the tablet to be conveyed toward the dispensing port 225 by means of the second rotating body 224. The width restriction member 227 restricts a size in a width direction of the tablet to be conveyed toward the dispensing port 225 by means of the second rotating body 224. This makes it possible to dispense only the tablet, which has a height equal to or less than a height h1 restricted by the height restriction member 226 and a width equal to or less than a width w1 restricted by the width restriction member 227, from the dispensing port 225 among tablets having various sizes. Thus, in the case where the height h1 and the width w1 respectively correspond to a height and a width of one tablet contained in the tablet containing portion 222, the unspecified cassette 22 can dispense the tablet in the unit of one tablet.

The unspecified cassette 22 also includes a height adjusting portion 226A for changing the height h1 restricted by the height restriction member 226 and a width adjusting portion 227A for changing the width w1 restricted by the width restriction member 227. In this case, the height adjusting portion 226A and the width adjusting portion 227A may be considered as examples of path adjusting means and a driving mechanism. A pinion gear engaged with a rack (gear) formed in an inner surface of an elongated hole 227B formed in the width restriction member 227 is provided on an outer peripheral surface of the width adjusting portion 227A.

The height adjusting portion 226A is rotatably supported by the housing of the unspecified cassette 22 and connected to a driving gear 226B shown in FIG. 6. The height adjusting portion 226A moves a position of a lower end of the height restriction member 226 in the vertical direction by being rotationally driven, and thereby changes the height h1 restricted by the height restriction member 226.

The width adjusting portion 227A is rotatably supported by the housing of the unspecified cassette 22 and connected to a driving gear 227C shown in FIG. 6. The width adjusting portion 227A changes a projection amount of the width restriction member 227 toward the tablet containing portion 222 by being rotationally driven, and thereby changes the width w1 restricted by the width restriction member 227. Specifically, the projection amount of the width restriction member 227 toward the tablet containing portion 222 is changed when each of the width adjusting portion 227A and the elongated hole 227B is relatively moved in a direction of an arrowed line R3 (see FIG. 4) by the rotation of the width adjusting portion 227A.

On the other hand, as shown in FIG. 7, the mounting portion 221 includes a driving gear 221C engaged with the driving gear 226B when the unspecified cassette 22 is mounted on the mounting portion 221 and a driving gear 221D engaged with the driving gear 227C when the unspecified cassette 22 is mounted on the mounting portion 221. The driving gear 221C is connected to the driving motor 243 of the unspecified driving portion 24. The driving gear 221D is connected to the driving motor 224 of the unspecified driving portion 24.

As shown in FIGS. 6 and 7, the unspecified cassette 22 and the mounting portion 221 include a driving gear 228A and the mounting portion 221 includes a driving gear 228B. The driving gears 228A and 228B are connected with each other when the unspecified cassette 22 is mounted on the mounting portion 221. The driving gear 228A is connected to a raising and lowering mechanism (not shown in the drawings) for raising and lowering the first rotating body 223 in the vertical direction. The driving gear 228B is connected to a driving motor (not shown in the drawings). With this configuration, since driving force is transmitted from the driving gear 228B to the driving gear 228A when the driving motor is driven, it is possible to raise and lower the first rotating body 223 with the raising and lowering mechanism. Thus, it is possible to arbitrarily adjust the number of the tablets which can be contained in the tablet containing portion 22 by raising and lowering the first rotating body 223.

In the unspecified cassette 22, the tablets in the tablet containing portion 222 are discharged from the first rotating body 223 to the second rotating body 224 when the first rotating body 223 is rotated in a rotational direction R1 (see FIGS. 4 and 5). Further, in the unspecified cassette 22, the tablets on the second rotating body 224 are conveyed toward the dispensing port 225 when the second rotating body 224 is rotated in a rotational direction R2 (see FIGS. 4 and 5).

Among the tablets conveyed by the second rotating body 224, the tablets stacked in the height direction will contact with the height restriction member 226 and return to the tablet containing portion 222. Further, among the tablets conveyed by the second rotating body 224, the tablets conveyed in line in the width direction will contact with the width restriction portion member 227 and return to the tablet containing portion 222.

Thus, in the unspecified cassette 22, the tablets having a size corresponding to the height h1 restricted by the height restriction member 226 and the width w1 restricted by the width restriction member 227 are conveyed toward the dispensing port 225 one by one in a state where the tablets are arranged in line on the second rotating body 224 in a circumferential direction thereof. Therefore, the unspecified cassette 22 can dispense the tablets contained in the tablet containing portion 222 in the unit of one tablet and control a dispensed amount of the tablets.

As described above, it is possible to change the height h1 restricted by the height restriction member 226 and the width w1 restricted by the width restricted member 227 by means of the unspecified cassette 22, and thereby dispensing desired types of tablets in the unit of one tablet.

Further, as shown in FIGS. 1 to 4, a display portion 25 (one example of the medicine displaying means), which can change display contents thereof, is provided at each of the unspecified cassettes 22. In this case, each of the display portions 25 is an electronic paper which can keep displaying the display contents even in a non-energizing state once the display contents have been written in an energizing state.

Specifically, connectors (not shown in the drawings) are respectively provided at each of the unspecified cassette 22 and the mounting portion 221. The connectors provided at the unspecified cassette 22 and the mounting portion 221 are connected with each other when the unspecified cassette 22 is mounted on the mounting portion 221. The display portion 25 is connected to the connector of the unspecified cassette 22 and the prescription control unit 1 is connected to the connector of the mounting portion 221. When the unspecified cassette 22 is mounted on the mounting portion 221, the display portion 25 and the prescription control unit 1 are electrically connected through the connectors. This allows the prescription control unit 1 to change a display state of each of the display portions 25. The display portion 25 is not limited to the electronic paper and may be other displaying means such as a liquid crystal display. Further, the display portion 25 may be provided at each of the mounting portions 221, on which each of the unspecified cassettes 22 corresponding to each of the mounting portions 221 is mounted.

As shown in FIG. 6, each of the unspecified cassettes 22 has a built-in RFID tag 26 for storing various information. The RFID tag 26 is a non-volatile storage medium which can rewrite stored information with the RFID reader writer 245. As described above, the RFID tag 26 is used for storing various information such as the cassette identification information for identifying each of the unspecified cassettes 22 and the medicine information allocated to each of the unspecified cassettes 22. The RFID tag 26 is equipped on a control board provided in each of the unspecified cassettes 22. The control board has a function of changing the display state of the display portion 25 of the unspecified cassette 22 according to a control signal from the prescription unit 1. Further, on the control board, an electric circuit is provided. The electric circuit is driven by electric power supplied through the connector, electric power supplied from an electric storage portion such as a battery equipped on the control board or electric power supplied at the time of writing the information to the RFID tag 26. Further, another configuration in which each of the unspecified cassettes 22 has other storage medium such as an EEPROM to which the prescription unit 1 can read and write information through the connector may be considered as another embodiment.

[Powdered Medicine Supplying Unit 3]

As shown in FIG. 1, the powdered medicine supplying unit 3 has two supplying portions 31 and 32. The powdered medicine supplying unit 3 can supply powdered medicine supplied into each of the supplying portions 31 and 32 to the packaging unit 5 in units of packages which are predetermined by the prescription control unit 1 according to various information such as the administration time.

Specifically, the powdered medicine supplying unit 3 includes two dispensing portions. One dispensing portion uniformly spreads powdered medicine supplied into the supplying portion 31 into a disc shape to scrape out the uniformed powdered medicine for each specific angle interval corresponding to a package. The other dispensing portion uniformly spreads powdered medicine supplied into the supplying portion 32 into a disc shape to scrape out the uniformed powdered medicine for each specific angle interval corresponding to a package. Powdered medicine to be supplied into the powdered medicine supplying unit 3 is measured in advance with a weighing device as a total amount of a prescription medicine to be prescribed to a patient.

[Manual Packaging Unit 4]

The manual packaging unit 4 includes a manual distributing portion on which there are provided a plurality of boxes into which tablets are respectively supplied in the units of packages and a manual dispensing portion for selectively dispensing the tablets contained in the boxes from each of the boxes. In the manual distributing portion, the plurality of boxes are arranged in matrix. The manual dispensing portion may take another configuration which can dispense the tablets contained in each of the boxes by selectively opening and closing a bottom surface of each of the boxes of the manual distributing portion, for example. In the medicine dispensing apparatus 100, the manual packaging unit 4 is used for dispensing a small amount of tablets less than one tablet such as a half of tablet. Since the manual packaging unit 4 is well known, description to the manual packaging unit 4 is omitted in the specification. In the conventional art, the manual packaging unit 4 is also used for dispensing any types of tablets not contained in the specified cassettes 21. On the other hand, the medicine dispensing apparatus 100 can dispense desired types of tablets by utilizing the unspecified cassettes 22. Needless to say, the medicine dispensing apparatus 100 can dispense desired types of tablets not contained in the specified cassettes 21 by utilizing the manual packaging unit 4.

[Packaging Unit 5]

The packaging unit 5 is one example of packaging means for packaging medicines supplied from the tablet supplying unit 2, the powdered medicine supplying unit 3 or the manual packaging unit 4 into one sheet of packaging paper in the units of packages according to the various information such as the administration time. For example, the packaging unit 5 packages the medicines in the units of packages with a transparent or semi-transparent roll charta sheet and seals the medicines with welding or the like. This makes it possible to discharge the charta sheet, in which the medicines are packaged in the units of packages, from the packaging unit 5.

FIG. 8 is a view showing one example of a charta sheet 51 discharged from the packaging unit 5. As shown in FIG. 8, a plurality of sheets of packaging paper in which a plurality of tablets are packaged in the units of packages are continuously formed in the charta sheet 51. Further, cutoff dotted lines 52A (perforated lines) for easily separating each sheet of the packaging paper 52 are formed between the adjacent sheets of the packaging paper 52. In a case where prescription data contains a powdered medicine, the packaging unit 5 can package the powdered medicine supplied from the powdered medicine supplying unit 3 into the sheet of the packaging paper 52 together with the tablets. Further, a printing portion (not shown in the drawings) for printing information on each sheet of the packaging paper 52 is provided at the packaging unit 5 and the printing portion can print prescription information such as a patient name, an administration time, a prescription medicine and a prescription amount on a surface of each sheet of the packaging paper 52.

[Packaging Control Unit 6]

As shown FIG. 2, the packaging control unit 6 includes a control portion 61 and a storage portion 62 and controls the tablet supplying unit 2, the powdered medicine supplying unit 3, the manual packaging unit 4, the packaging unit 5 and the like to allow the medicine dispensing apparatus 100 to carry out a packaging operation. The packaging control unit 6 is built in the medicine dispensing apparatus 100.

The control portion 61 is control means having a CPU, a RAM, a ROM, an EEPROM or the like. The control portion 61 controls the CPU to carry out various processes depending on various programs stored in the ROM, the EEPROM or the like in advance. The RAM and the EEPROM are utilized as a temporary storage memory (working area) for the various processes carried out by the CPU. The control portion 61 may be an integrated circuit such as an ASIC or a DSP.

The storage portion 62 is storage means such as a hard disk device or a SSD (Solid State Drive) for storing various data. Specifically, a packaging control program for allowing a computer such as the control portion 61 to carry out a packaging process described below (see a right side of FIG. 11) is stored in the storage portion 62 in advance. The packaging control program is stored in a computer-readable storage medium such as a CD, a DVD and a semiconductor memory and retrieved by a reading device such as a disk drive (not shown in the drawings) to be installed into the storage portion 12. The present invention can be interpreted as an invention of the computer-readable storage medium storing the packaging control program.

[Barcode Reader 7]

The barcode reader 7 can read a code for identifying a medicine. The barcode reader 7 is code reading means for reading the JAN code, the RSS code or the QR code (registered trade-mark) written on a tablet container (such as a box and a bottle) or a PTP sheet placed on a medicine shelf in a pharmacy. For example, the barcode reader 7 is a portable device such as a PDA. The barcode reader 7 may be a well-known picking auxiliary device which is used by a pharmacist or the like for picking out medicines from the medicine shelf according to the prescription. The picking auxiliary device is used when the pharmacist or the like picks out the medicines from the medicine shelf to manually prepare the medicines according to the prescription. For example, the picking auxiliary device identifies the medicines from the JAN code and matches the identified medicines with the prescription data.

Then, the information read by the barcode reader 7 is inputted into the prescription control unit 1 with wireless communication of the barcode reader 7. By utilizing the wireless communication in this manner, it is possible to freely bring the barcode reader 7 to the medicine dispensing apparatus 100 or the medicine shelf and carry out a work for supplying tablets into the unspecified cassettes 22 at an arbitrary location. Regardless to say, the barcode reader 7 may be connected to the prescription control unit 1 with a wired connection. In a case where a plurality of medicine dispensing apparatuses 100 are provided in the pharmacy, a plurality of barcode readers 7 are respectively provided in the plurality of medicine dispensing apparatuses 100.

[Prescription Control Unit 1]

The prescription control unit 1 is a computer for generally controlling the medicine dispensing apparatus 100. As shown in FIGS. 1 and 2, the prescription control unit 1 includes a control portion 11, a storage portion 12, a monitor 13, an operating portion 14, a communication IF 15 and the like.

The control portion 11 is control means having a CPU, a RAM, a ROM, an EEPROM and the like. The control portion 11 controls the CPU to carry out various processes depending on various programs stored in the ROM, the EEPROM, the storage portion 12 or the like in advance. The RAM and the EEPROM are utilized as a temporary storage memory (working area) for the various processes carried out by the CPU. The control portion 11 may be an integrated circuit such as an ASIC and a DSP.

The storage portion 12 is storage means such as a hard disk device or a SSD (Solid State Drive) for storing various data. Specifically, a medicine dispensing program for allowing a computer such as the control portion 11 or the like to carry out the medicine dispensing process described below (see a left side of FIG. 11) is stored in the storage portion 12 in advance.

The medicine dispensing program is stored in a computer-readable storage medium such as a CD, a DVD and a semiconductor memory and retrieved by a reading device such as a disk drive (not shown in the drawings) to be installed into the storage portion 12. The present invention can be interpreted as an invention of the computer-readable storage medium storing the medicine dispensing program.

The storage portion 12 also stores various databases such as a medicine master, a patient master, a cassette master and a pharmacy master. The control portion 11 can update the various databases stored in the storage portion 12 based on data read from a storage medium such as a CD, a DVD and a semiconductor memory by a reading device such as a disk drive (not shown in the drawings). Further, the control portion 11 can change items in the various databases depending on a user operation performed on the operating portion 14.

The medicine master contains information on each medicine such as a medicine ID, a medicine code, a medicine name, a JAN code (or an RSS code), a medicine bottle code, a category (a dosage form: a powdered medicine, a tablet, pharmaceutical solution, a medicine for external use and the like), a medicine size (height and width), a specific gravity, a type of medicine (a common medicine, a poisonous medicine, a narcotic drug, a powerful medicine, an antipsychotic medicine, a therapeutic medicine or the like), a blending variation, an excipient and a precaution. The patient master contains information on a patient such as a patient ID, a name, a gender, an age, a medical history, a prescription medicine history, family information, a hospital department, a hospital ward and a hospital room. The pharmacy master contains information on a pharmacy such as a pharmacy name, a pharmacist name and a pharmacist ID. The cassette master is information indicating a correspondence relationship between cassette identification information of each of the specified cassettes 21 and the medicine information allocated to each of the specified cassettes 21. The cassette master is registered by the control portion 11 depending on, for example, a user operation performed on the operating portion 14 at the time of the initial setting of the medicine dispensing apparatus 100.

Further, the storage portion 12 stores allocation information 121 indicating an allocation state between each of the unspecified cassettes 22 and the medicine information and driving correspondence information indicating a correspondence relationship between the medicine information and the driving conditions of each of the unspecified cassettes 22. In this case, the storage portion 12 is examples of allocation information storage means and driving correspondence information storage means. The allocation information 121 and the driving correspondence information 122 are used in the medicine dispensing process (described below) carried out by the control portion 11.

FIG. 9 is a view showing one example of the allocation information 121. FIG. 10 is a view showing one example of the driving correspondence information 12.

As shown in FIG. 9, medicine IDs respectively indicating types of medicines allocated to each of the unspecified cassettes 22 at present are stored in the allocation information 121 as medicine information. Regardless to say, other medicine information such as a tablet name, a medicine code and a JAN code (or an RSS code) may be stored instead of the medicine ID. Here, it is assumed that cassette numbers "C1" to "C4" are preliminarily set to the four unspecified cassettes 22 which are arranged in the tablet supplying unit 2 from left to right in turn. The cassette identification information is further stored in the RFID tag 26 of each of the unspecified cassettes 22. In the allocation information 121, a message indicating "non-allocation state" is stored in the unspecified cassette 22 which has not yet been subjected to the allocation of the medicine information. Specifically, in the allocation information 121 shown in FIG. 9, medicine information having a medicine ID "M1" is allocated to the unspecified cassette 22 having the cassette number "C1," medicine information having a medicine ID "M2" is allocated to the unspecified cassette 22 having the cassette number "C3," and messages indicating the non-allocation state are respectively allocated to the unspecified cassettes having the cassette numbers "C2" and "C4." It is noted that a data structure of the allocation information 121 shown in FIG. 9 is merely one example and the allocation information 121 may be information stored in the storage portion 12 as, for example, one element of the medicine master. In this case, the cassette identification information for each of the unspecified cassettes 22 to which medicine information on medicines are respectively allocated is stored so as to correspond to the medicines contained in the medicine master.

Further, as shown in FIG. 10, driving conditions predetermined so as to correspond to the medicine information are contained in the driving condition information 122. Each of the driving conditions contains three conditions including a previous driving condition related to adjustment of the unspecified cassette 22 before a start of a dispensation of the tablets from the unspecified cassette 22, an under-driving condition related to driving control during the dispensation of the tablets from the unspecified cassette 22 and a driving stop condition related to driving control to be performed when the dispensation of the tablets from the unspecified cassette 22 is stopped.

Specifically, the example of the driving correspondence information 122 is shown in FIG. 10 as the driving conditions respectively corresponding to the tablets having the medicine IDs "M1," "M2," "M3" and "M4." The driving correspondence information 122 stores information related to items of a height of the dispensing path, a width of the dispensing path, a dispensing speed and a reverse rotation control. It is noted that the driving conditions described above are merely one example. For example, in a case where the unspecified cassette 22 dispenses the tablets one by one with utilizing vibration, a frequency or amplitude of the vibration may be defined as the driving condition.

The height of the dispensing path and the width of the dispensing path are merely examples of the previous driving condition. The height of the dispensing path and the width of the dispensing path are the height h1 and the width w1 (see FIG. 5) which are preliminarily set as values for dispensing the tablets one by one from the dispensing port 225 by the second rotating body 224 of the unspecified cassette 22.

The dispensing speed is merely one example of the under-driving condition. The dispensing speed is indicated in each medicine information as a suitable rotating speed of the second rotating body 224 at the time of the dispensation of the tablets from the unspecified cassette 22. For example, if the size of the tablet is small and the rotating speed of the driving motor 242 is fast, extra tablets are not likely to be dispensed until the driving motor 242 is stopped. On the other hand, if the size of the tablet is large, the extra tablets are not dispensed until the driving motor 242 is stopped even if the rotating speed of the driving motor 242 is fast. Thus, the dispensing speed of the tablets set as the driving condition, that is, a conveying speed of the tablets by means of the second rotating body 224 may be variable depending on the size of the tablet to be dispensed. Specifically, in the case where the size of the tablet is large, the dispensing speed may be set so as to be slower than the dispensing speed in the case where the size of the tablet is small. The dispensing speed is not limited to a form "tablets/min" shown in FIG. 10. The dispensing speed may be stored in a form of the rotating speed of the second rotating body 224, the rotating speed of the driving motor 242 or the like. Further, not only the rotating speed of the second rotating body 224 but also a rotating speed of the first rotating body 223 may be set as the driving condition.

The item of the reverse rotation control is merely one example of the driving stop condition. The item of the reverse rotation operation is information related to a condition for determining whether or not a reverse rotation operation, which switches a conveying direction of the tablets to a reverse direction by means of the second rotating body 224, is carried out at the time of stopping the dispensation of the tablets from the unspecified cassette 22. For example, for a tablet having a spherical shape or the like, which has a risk that the tablets remaining on the second rotating body 224 are likely to be rolled and be extra dispensed when only the driving of the second rotating body 224 is stopped, the reverse rotation control is set to be "ON." This makes it possible to prevent the tablets from being extra dispensed at the time of stopping the dispensation of the tablet from the unspecified cassette 22. On the other hand, for the tablet having a shape, which is not likely to be rolled when the driving of the second rotating body 224 is stopped, the reverse rotation control is set to be "OFF." In this case, reverse rotation operation is unnecessary and not carried out.

It is noted that a data structure of the driving correspondence information 122 shown in FIG. 10 is merely one example and the driving conditions defined by the driving correspondence information 122 may be stored in the storage portion 12 as, for example, one element of the medicine master.

In this embodiment, description will be given to the case where the driving correspondence information 122 contains each item of the height of the dispensing path, the width of the dispending path, the dispensing speed and the reverse rotation control as the driving conditions (see FIG. 10) corresponding to each medicine information.

On the other hand, another configuration in which the medicine dispensing apparatus 100 utilizes one or more of the items of the height of the dispensing path, the width of the dispensing path and the reverse rotation condition as the driving conditions may be considered as another embodiment.

Namely, one or more of the previous driving condition, the under-driving condition and the driving stop condition may be set in the medicine dispensing apparatus 100 as the driving condition corresponding to each medicine information in advance.

Furthermore, other configuration in which a plurality of conditions such as the previous driving condition, the under-driving condition and the driving stop condition are set as the driving conditions corresponding to each medicine information in advance and the medicine dispensing apparatus 100 can select one or more of the conditions such as the previous driving condition, the under-driving condition and the driving stop condition as the driving conditions to be used may be considered as other embodiment.

The monitor 13 is displaying means such as a liquid crystal display for displaying various information and an operation screen according to a control command from the control portion 11. For example, various information such as an input screen for inputting prescription data and a selection screen for selecting prescription data is displayed on the monitor 13.

The operating portion 14 is operating means such as a keyboard, a mouse and a touch panel for receiving a user operation. The operating portion 14 inputs an operation signal corresponding to the user operation into the control portion 11. For example, the operating portion receives various operation inputs such as an input operation for the prescription data at the input screen displayed on the monitor 13, a selection operation for the prescription data at the selection screen and an issuing operation of the prescription data for requesting a start of the packaging operation according to the prescription data.

The communication IF 15 is a communication interface for connecting the medicine dispensing apparatus 100 to a communication network N2 such as a LAN. The communication IF 15 carries out data communication between the medicine dispensing apparatus 100 and a host system such as a prescription input terminal 200 connected through the communication network N2. For example, the prescription input terminal 200 is an electronic medical record system provided in a hospital or a nursing facility, a prescription management system provided in a pharmacy inside or outside a hospital or the like. The communication IF 15 also includes a wireless communication interface such as a wireless communication card for carrying out wireless data communication between the medicine dispensing apparatus 100 and various wireless communication devices such as the barcode reader 7.

The communication IF 15 receives prescription data from the prescription input terminal 200 to input the prescription data into the control portion 11. For example, the communication IF 15 monitors whether or not prescription data is stored in a predetermined storage area of storage means provided in the prescription input terminal 200. In a case where the prescription data is stored in the predetermined storage area of the storage means, the communication IF 15 retrieves the prescription data from the predetermined storage area. Needless to say, the communication IF 15 may receive the prescription data transmitted from the prescription input terminal 200.

[Medicine Dispensing Process and Packaging Control Process]

Hereinafter, description will be given to examples of procedures for the medicine dispensing process carried out by the control portion 11 of the prescription control unit 1 in the medicine dispensing apparatus 100 and the packaging control process carried out by the control portion 61 of the packaging control unit 6 in the medicine dispensing apparatus 100. Hereinafter, the procedures carried out by the control portion 11 will be referred to as step S1, S2 . . . and the procedures carried out by the control portion 61 will be referred to as step S11, S12 . . . . In this regard, a series of processes, which are carried out by either one of the control portion 11 and the control portion 61 and can provide the same results as results of the medicine dispensing process and the packaging control process, may be carried out.

(Prescription Control Unit 1 Side: Step S1)

First, at a step S1, the control portion 11 determines whether or not an issuing request for prescription data is issued. Specifically, in a case where an issuing operation for issuing the prescription data registered in advance is carried out to the operating portion 14, the control portion 11 determines that the issuing request for the prescription data is issued. The prescription data is prescription data obtained from a host system such as the prescription input terminal 200 or registered by a user operation performed on the operating portion 14 and then stored in the storage portion 12.

The control portion 11 holds the process at the step S1 on standby until the issuing request for the prescription data is issued (the case of determining "No" at the step S1). On the other hand, the control portion 11 shifts the process to a step S2 in a case where the control portion 11 determines that the issuing request for the prescription data is issued (the case of determining "Yes" at the step S1). In this regard, another configuration in which the control portion 11 may determine that the issuing request for the prescription data is issued without detecting the issuing operation when the prescription data is received from the host system such as the prescription input terminal 200 and then shift the process to the step S2 may be considered as another embodiment.

(Prescription Control Unit 1 Side: Step S2)

Next, at the step S2, the control portion 11 determines whether or not there exist the specified cassettes 21 which correspond to all of medicine information inputted as medicine information specified in the prescription data in which tablets are designated to be dispensed. Specifically, the control portion 11 determines, on the basis of the cassette master stored in the storage portion 12, whether or not types of tablets not allocated to the specified cassettes 21 are contained in the prescription data. The cassette master is updated by the control portion 11 on the basis of medicine information, which is read from the RFID tags (not shown in the drawings) respectively provided at the specified cassettes 21, by means of a reading device such as the RFID reader writer 232 respectively provided at the mounting portions 211. Further, the control portion 11 allows the monitor 13 to display an edit screen for editing the cassette master to update the cassette master according to a user operation performed on the operating portion 14 on the edit screen.

In a case where the control portion 11 determines that the specified cassettes 21 corresponding to all of the medicine information on the tablets to be dispensed do not exist (the case of determining "No" at the step 2), that is, in a case where the types of tablets not allocated to the specified cassettes 21 are specified in the prescription data as prescription medicines, the control portion 11 shifts the process to a step S3.

On the other hand, in a case where the control portion 11 determines that the specified cassettes 21 corresponding to all of the medicine information on the tablets to be dispensed exist (the case of determining "Yes" at the step S2), that is, in a case where all types of tablets specified in the prescription data as the prescription medicines are respectively contained in the specified cassettes 21, the control portion 11 shifts the process to a step S7. In this case, at the step S7, a start request for the packaging operation which is the same as the conventional art is transmitted to the control portion 61 through each of the specified cassettes 21 to carry out a process for the packaging operation.

In another configuration in which the medicine dispensing apparatus 100 does not include any specified cassettes 21, it is possible to omit the step S2 from the process and directly shift the process from the step S1 to the step S3 when the control portion 11 determines that the issuing request for the prescription data is issued at the step S1.

Further, allocation exclusion medicine information which is set in advance may be stored in the storage portion 12 as medicine information which should not be allocated to the unspecified cassettes 22. Furthermore, in a case where the specified cassette 21 corresponding to the medicine information on the tablet to be dispensed does not exist and the medicine information on the tablets to be dispensed matches the allocation exclusion medicine information, the control portion 11 may allow the monitor to display a message indicating that the manual packaging unit 4 should be used without allocating the medicine information to one of the unspecified cassettes 22. For example, if a tablet which has high possibility that the tablet allows colored powder adhere to the unspecified cassette 22 is set as the allocation exclusion medicine information, it is possible to prevent the colored powder from adhering to another tablet which is to be subsequently contained in the unspecified cassette 22. Further, medicine information on a tablet, which has a shape not suitable for the dispensation from the unspecified cassette 22, may be set as the allocation exclusion medicine information. In this case, the control portion 11 allows the monitor 13 to display a message indicating that the manual packaging unit 4 should be used. Another configuration in which the control portion 11 determines whether or not the medicine information on the tablet to be dispensed matches the allocation exclusion medicine information without determining whether or not the specified cassette 21 corresponding to the medicine information on the tablets to be dispensed exists may be considered as another embodiment. In this case, another configuration in which the control portion 11 allows the monitor 13 to display a message indicating that the manual packaging unit 4 should be used without allocating the medicine information to one of the unspecified cassettes 22 when the medicine information on the tablets to be dispensed matches the allocation exclusion medicine information may be considered as another embodiment.

(Prescription Control Unit 1 Side: Step S3)

At the step S3, among the inputted medicine information on the tablets designated to be dispensed by the prescription data, if there are no specified cassettes having a medicine corresponding to the medicine information, the control portion 11 allocates the medicine information to one of the unspecified cassettes 22 which has not yet been subjected to the allocation. In a case where a plurality of medicine information are contained in the prescription data and there are no specified cassettes having medicines corresponding to the medicine information, the control portion 11 allocates the plurality of medicine information to the unspecified cassettes 22 respectively. In the case where the medicine information on the tablets to be dispensed is inputted by the prescription data in this manner, the control portion 11 carries out this process (allocating step) for allocating the medicine information to one of the unspecified cassettes 22. Such operation of the control portion 11 is one example of allocating means.

Specifically, the control portion 11 carries out a process for identifying the unspecified cassette 22, which is in a communication possible state (controllable state) at present, among the unspecified cassettes 22. For example, the control portion 11 determines that the unspecified cassette 22, which completes reading of information from the RFID tag 26 by means of the RFID reader writer 232, is in the communication possible state among the unspecified cassettes 22.

Then, the control portion 11 determines, on the basis of the allocation information 121 (see FIG. 9), whether or not current medicine information has been allocated to one of the unspecified cassettes 22 in the communication possible state to allocate the medicine information on the medicine to be dispensed to the unspecified cassette 22 which has not yet been subjected to the allocation. At this time, the control portion 11 selects one of the unspecified cassettes 22 to which the medicine information should be allocated and then updates the contents of the allocation information 121 according to this allocation result. The unspecified cassette 22 to which the medicine information is allocated in this manner can communicate with the control portion 11 and write information to the electronic paper 25 by means of the control portion 11. The control portion 11 may pick out each of the unspecified cassettes 22 as candidates for allocation objects without determining whether or not each of the unspecified cassettes 22 is in the communication possible state.

In this step, there is possibility that there exist a plurality of candidates for the unspecified cassette 22 to which the medicine information should be allocated. In this case, the control portion 11 may determine, on the basis of a predetermined priority order, whether or not each of the unspecified cassettes 22 has been already subjected to the allocation of the medicine information. Then, the control portion 11 allocates the medicine information to the unspecified cassette 22 which is first determined that the medicine information has not yet been subjected to the allocation. Further, the control portion 11 may determine whether or not each of the medicine information has been already allocated to each of the unspecified cassettes 22 in order from the unspecified cassette 22 having a less use frequency. Then, the control portion 11 allocates the medicine information to the unspecified cassette 22 which is first determined that the medicine information has not yet been subjected to the allocation so that the use frequencies of the unspecified cassettes 22 are equalized with each other. Furthermore, the control portion 11 may select the unspecified cassette to which the medicine information was allocated just before from the unspecified cassettes 22, if the allocated medicine information is the same as the present medicine information on the tablets to be dispensed in this time or tablet size contained in the allocated medicine information is nearly the same as the tablet size of the tablets to be dispensed in this time. In a case where the unspecified cassette 22 to which the medicine information is not allocated does not exist, the control portion 11 allows the monitor 13 to display a message indicating that the unspecified cassette 22 does not exist to report it to the user.

At the step S3, the control portion 11 controls the RFID reader writer 232 to store the medicine information, which is allocated to the unspecified cassette 22, in the RFID tag 26 of the unspecified cassette 22 to which the medicine information is allocated. At this time, the control portion 11 may store, on the basis of the prescription data, various information such as a dispensed amount of the tablets indicated in the medicine information, a patient name, an allocation time and date, a pharmacist name in charge and identification information of prescription in the RFID tag 26 of the unspecified cassette 22 together with the medicine information.

On the other hand, there is possibility that the medicine information is not stored in the RFID tag 26 of the unspecified cassette 22. Specifically, there is possibility that the cassette identification information is stored in the RFID tag 26 in advance and the RFID reader writer 245 is an RFID reader which can only read information. In this case, the control portion 11 also recognizes the medicine information allocated to the unspecified cassette 22 on the basis of the allocation information and the cassette identification information read from the RFID tag 26 (see FIG. 9).

(Prescription Control Unit 1 Side: Step S4)

At the step S4, the control portion 11 identifies a driving conditions corresponding to the medicine information on the tablets to be dispensed on the basis of the driving correspondence information 122 (see FIG. 10) to transmit the driving conditions and the cassette identification information allocated to the unspecified cassette 22 to the control portion 61. With this configuration, the control portion 61 can drive the unspecified cassette 22 according to the driving conditions. In the case of driving the unspecified cassette 22 by carrying out the process at the step S4, the control portion 11 driving the unspecified cassette 22 according to the driving condition may be considered as driving control means.

Another configuration in which the control portion 11 allows the monitor 13 to display the cassette identification information of the unspecified cassettes 22 and setting contents of the driving conditions respectively corresponding to the unspecified cassettes 22 and changes the setting contents of the driving conditions according to a user operation performed on the operating portion 14 may be considered as another embodiment. In this regard, the changed setting contents are reported from the control portion 11 to the control portion 61. This makes it possible to change the driving conditions of the unspecified cassette 22 for dispensing the tablets from the unspecified cassette 22 by means of a user arbitrary operation input. Further, the user can confirm the setting contents of the driving conditions corresponding to the medicine information on the tablets to be dispensed by referring to the monitor 13.

(Packaging Control Unit 6 Side: Step S11)

On the other hand, in the packaging control unit 6, the control portion 61 determines whether or not the driving conditions are received from the control portion 11 at a step S11. The control portion 61 shifts the process to a step S12 in a case where the control portion 61 determines that the driving conditions are received (the case of determining "Yes" at the step S11). On the other hand, the control portion 61 shifts the process to a step S13 in a case where the control portion 61 determines that the driving conditions are not received (the case of determining "No" at the step S11). The control portion 61 associates the driving conditions received from the control portion 11 with the cassette identification information of the unspecified cassette 22, to which the medicine information is allocated, to store the driving conditions in the storage portion 62.

(Packaging Control Unit 6 Side: Step S12)

At the step S12, the control portion 61 drives the unspecified cassette 22 corresponding to the cassette identification information received together with the driving condition according to the previous driving condition to change the height of the dispensing path and the width of the dispensing path. Thus, in the medicine dispensing apparatus 100, in a case where the driving condition contains the previous driving condition, the control portion 61 drives the unspecified cassette 22 according to the previous driving condition (the height and the width of the dispensing path) and then carries out the dispensation of the tablets from the unspecified cassette (step S14).

Specifically, the control portion 61 controls the height adjusting portion 226A and the width adjusting portion 227A according to the driving condition to change a type of tablet which can be currently dispensed from the unspecified cassette 22 in the unit of one tablet to a type of tablet designated by the medicine information allocated at the step S3. First, the control portion 61 drives the driving motor 233 and the driving motor 234 to return positions of the height restriction member 226 and the width restriction member 227 to initial states. Then, the control portion 61 drives the height adjusting portion 226A with the driving motor 233 to change the height h1 restricted by the height restriction member 226 of the unspecified cassette 22 to the height of the dispensing path designated by the driving condition. Further, the control portion 61 drives the width adjusting portion 227A with the driving motor 234 to change the width w1 restricted by the width restriction member 227 of the unspecified cassette 22 to the width of the dispensing path designated by the driving condition. Needless to say, if the control portion 61 takes another configuration which can detect current status of the height restriction member 226 and the width restriction member 227, the control portion 61 can drive the driving motor 233 and the driving motor 234 on the basis of that detection result.

Once the height h1 and the width w1 of the dispensing path are changed according to the driving condition in this manner, the unspecified cassette 22 can one by one dispense the tablets designated to be dispensed by the medicine information allocated at the step S3 and control the dispensed amount of the tablets. In this case, the control portion 61 carrying out the process at the step S12 (driving control step) is one example of driving control means.

In this regard, there is possibility that the unspecified cassette 22 is in a state where the unspecified cassette 22 is not mounted on the mounting portion 221 at the time of allocating the medicine information to the unspecified cassette 22. In this case, the control portion cannot drive the unspecified cassette 22 according to the driving condition at the step S12. Thus, the control portion 61 stores flag information indicating whether or not the driving condition received from the control portion is reflected to the unspecified cassette 22 in the storage portion 62 and updates the flag information as required. The control portion 61 refers to the flag information at the time of starting the packaging operation at a step S14 described below. In a case where the driving condition is not reflected to the unspecified cassette 22 to be used in the packaging operation, the control portion drives the unspecified cassette 22 according to the driving condition to change the height h1 and the width w1 of the dispensing path before the packaging operation is carried out.

Another configuration in which the driving condition does not contain the previous driving condition and the height h1 and the width w1 of the dispensing path can be arbitrarily adjusted by manually activating the height adjusting portion 226A and the width adjusting portion 227A of the unspecified cassette 22 may be considered as another embodiment. In this case, the user adjusts the height h1 and the width w1 of the dispensing path of the unspecified cassette 22 and then mounts the unspecified cassette 22 on the mounting portion 221 of the tablet supplying unit 2. The height adjusting portion 226A and the width adjusting portion 227A may take configurations in which the height adjusting portion 226A and the width adjusting portion 227A can be activated by a rotating operation with a tool such as a driver, for example.

(Prescription Control Unit 1 Side: Step S5)

Next, at a step S5, the control portion 11 allows the display portion 25 of the unspecified cassette 22 to which the medicine information is allocated at the step S3 to display the medicine information allocated to the unspecified cassette 22. In this case, the control portion 11 carrying out this displaying process is one example of display control means.

Figure 12A:
FIG. 12 is a view showing display examples of a display portion of the unspecified cassette.

For example, the control portion 11 extracts predetermined information on display items from the prescription data to allow the display portion 25 to display the information. FIG. 12(A) is a view showing a display example of the medicine information on the display portion 25. As shown in FIG. 12(A), the display portion 25 displays "A Tablet (M1)" which is a medicine name (medicine ID) of the tablet allocated to the unspecified cassette 22, "15 tablets" which is a dispensed amount (amount to be dispensed) and a JAN code (barcode). It is noted that the display example of the medicine information shown in FIG. 12(A) is merely one example and the display portion 25 may display various information such as a patient name, an allocation time and date and a name of person in charge.

Since the display portion 25 is the electronic paper, a display state of the display portion 25 is kept even if the unspecified cassette 22 is removed from the mounting portion 221 after the medicine information is displayed at the step S5. Thus, for example, even if the user brings the unspecified cassette into the medicine shelf, the user can confirm the medicine information on the tablet to be supplied into the unspecified cassette 22 by visually inspecting the display portion 25. Thus, it is possible to suppress human errors of the user at the time of supplying the tablets into the unspecified cassette 22. Further, it is possible to take another configuration which prevents the unspecified cassette 22 from being removed from the mounting portion 221 with a rocking mechanism provided at the mounting portion 221 until the medicine information is displayed on the display portion 25 of the unspecified cassette 22. Furthermore, the control portion 11 may carry out the step S5 on condition that the control portion 11 has completed the adjustments of the height of the dispensing path and the width of the dispensing path of the unspecified cassette 22 according to the previous driving condition for the unspecified cassette 22.

(Prescription Control Unit 1 Side: Step S6)

Then, at a step S6, the control portion 11 determines whether or not a supplying complete operation, which means that the supplying of the tablets into the unspecified cassette 22 is completed, is carried out to the operating portion 14. Specifically, the user removes the unspecified cassette 22 from the tablet supplying unit 2 after the medicine information is allocated to the unspecified cassette 22 at the step S3 and then the medicine information is displayed on the display portion 25 of the unspecified cassette 22. Then, the user supplies the tablets in a required amount into the unspecified cassette 22 with referring to a prescription sheet corresponding to the prescription data or the medicine information displayed on the display portion 25. Then, the user mounts the unspecified cassette 22 to the tablet supplying unit 2 to carry out the supplying complete operation to the operating portion 14. In a case where a plurality of medicine information are allocated to the plurality of unspecified cassettes 22 at the step S3, the control portion 11 determines whether or not a plurality of supplying complete operations are carried out to all of the unspecified cassettes 22 respectively corresponding the plurality of medicine information.

The control portion 11 holds the process at the step S6 on standby until the supplying complete operation is carried out (the case of determining "No" at the step S6). On the other hand, the control portion 11 shifts the process to a step S7 when the control portion 11 determines that the supplying complete operation is carried out (the case of determining "Yes" at the step S6).

In this regard, it is possible to take another configuration in which a mounting and removing detection sensor for detecting mounting and removing of the unspecified cassette 22 is provided at the mounting portion 221 and the control portion 11 reports, on the basis of a detection result from the mounting and removing detection sensor, a message indicating that the supplying of the tablets into the unspecified cassette 22 is not carried out. Namely, the control portion 11 reports an error to the user when the supplying complete operation is carried out in a state where the removing of the unspecified cassette 22 is not detected by the mounting and removing detection sensor even once during a period from allocating the medicine information to the unspecified cassette 22 to carrying out the supplying complete operation. This reporting is carried out by, for example, reporting means such as the monitor 13 and a speaker (not shown in the drawings). Further, at the step S6, the control portion 11 may determine that the supplying of the tablets into the unspecified cassette 22 completes when the mounting and removing detection sensor detects the mounting and removing of the unspecified cassette 22 and then shift the process to the step S7.

(Prescription Control Unit 1 Side: Step S7)

At the step S7, the control portion 11 transmits a start request for the packaging operation based on the prescription data to the control portion 61.

Especially, for the packaging operation of tablets which are not contained in the specified cassettes 21 but contained in the medicine information and designated to be dispensed by the prescription data, the control portion 11 transmits the start request, for example, in the following procedures.

First, the control portion 11 retrieves the cassette identification information of each of the unspecified cassettes 22 from the RFID tags 26 of the unspecified cassettes 22 respectively mounted on the mounting portions 211 to identify the unspecified cassettes 22 mounted on the mounting portions 221 at present. This makes it possible for the control portion 11 to identify the unspecified cassettes 22 respectively mounted on the mounting portions 221, thus the user can arbitrarily mount each of the unspecified cassettes 22 on any one of the mounting portions 221. For example, in a case where the unspecified cassettes 22 are again mounted on the mounting portions 221 so that mounting positions of the unspecified cassettes are changed after the plurality of medicine information are allocated to the plurality of unspecified cassettes 22 at the step S3 and each of the unspecified cassettes 22 is removed from each of the mounting portions 211, the control portion 11 can recognize the mounting portions 221 on which the unspecified cassettes 22 are respectively mounted. Further, another configuration in which the unspecified cassettes 22 can be respectively mounted on the mounting portions 221 in a structurally one-to-one attachable relationship may be considered as another example of the tablet supplying unit 2. For example, concave-convex portions, which can be engaged with each other, may be formed on each of the unspecified cassettes 22 and each of the mounting portions 221 and only specific one of the unspecified cassettes 22 can be mounted on specific one of the mounting portions 221. In this case, the one unspecified cassette 22 which can be mounted on the one mounting portion 211 is uniquely determined, and thus information indicating the correspondence relationship between each of the mounting portions 221 and the medicine information may be stored in the storage portion 12 as the allocation information 121 (see FIG. 9).

Among the unspecified cassettes 22, the control portion 11 identifies, on the basis of the allocation information 121, each of the unspecified cassettes 22 in which tablets indicated in the medicine information are contained. Then, for each of the medicine information specified in the prescription data, the control portion 11 transmits information required for the packaging operation, such as the cassette identification information of the unspecified cassette 22 to which the medicine information is allocated, the identification information of the mounting portion 221 on which the unspecified cassette 22 is mounted and the dispensed amount of tablets, to the control portion 61.

(Packaging Control Unit 6 Side: Step S13)

On the other hand, in the packaging control unit 6, the control portion 61 determines whether or not the start request for the packaging operation is received from the control portion 11 at a step S13. The control portion 61 shifts the process to a step S14 in a case where the start request for the packaging operation is received (the case of determining "Yes" at the step S13). On the other hand, the control portion 61 shifts the process to the step S16 in a case where the start request for the packaging operation is not received (the case of determining "No" at the step S13).

(Packaging Control Unit 6 Side: Step S14)

At the step S14, according to the start request for the packaging operation, the control portion 61 carries out the packaging operation in which required medicines are dispensed from the tablet supplying unit 2, the powdered medicine supplying unit 3 and the manual packaging unit 4 and then the packaging unit 5 packages the medicines in the units of packages according to various information such as the administration time. In this specification, description will be given to a dispensing operation for dispensing tablets by means of the tablet supplying unit 2 with omitting description to controls for the powdered medicine supplying unit 3, the manual packaging unit 4 and the packaging unit 5 because these controls are the same as the conventional art.

According to the driving conditions corresponding to the medicine information allocated at the step S3, in the tablet supplying unit 2, the control portion 61 changes rotating speed of the driving motor 242 of the unspecified driving portion 24 which is driven at the time of the dispensation of the tablets from the unspecified cassette 22. Namely, the rotating speed of the second rotating body 224 at the time of the dispensation of the tablets from the unspecified cassette 22 is changed to change the dispensing speed of the tablets from the unspecified cassette 22 depending on the type of tablet. In this case, the control portion 11 carrying out this process is one example of driving control means.

Specifically, the control portion 61 drives the driving motor 241 and the driving motor 242 corresponding to the unspecified cassettes 22 to which the medicine information on the tablets to be dispensed is allocated to dispense the tablets by rotating the first rotating body 223 and the second rotating body 224. At this time, the control portion 61 drives the driving motor 242 according to the dispensing speed determined as the driving conditions corresponding to the medicine information in the driving correspondence information 122. With this configuration, in the unspecified cassette 22, the dispensing speed of the tablets by means of the second rotating body 224 is changed to suitable speed for the type of tablet. In the medicine dispensing apparatus 100, the control portion 61 drives the unspecified cassette 22 according to the under-driving condition (dispensing speed) to dispense the tablet from the unspecified cassette 22 in the case where the driving conditions contain the under-driving condition as described above. In a case where the unspecified cassette 22 takes another configuration in which the unspecified cassette 22 does not include the height restriction member 226 and the width restriction member 227, the control portion 61 may change only the dispensing speed of the tablets from the unspecified cassette 22. Further, the driving speed of the driving motor 231 may be constant or changed depending on the type of tablet. In the packaging operation, the number of the tablets dispensed from the unspecified cassette 22 is counted by a counter (which is one example of counting means and not shown in the drawings) having an optical sensor provided at the dispensing port 225 of the unspecified cassette 22 and then inputted into the control portion 61 as a discharged number. With this configuration, the control portion 61 can control the driving of the unspecified cassette 22 on the basis of the discharged amount inputted from the counter to dispense the tablets from the unspecified cassette 22 in the predetermined dispensed amount (prescription amount).

The control portion 61 carries out a stopping control for stopping the dispensation of the tablet from the unspecified cassette 22 according to the status of the reverse rotation operation contained in the driving conditions corresponding to the medicine information in the driving correspondence information 122. In this case, the control portion 11 carrying out this process is one example of driving control means. In the medicine dispensing apparatus 100, in a case where the driving condition contains the driving stop condition as described above, the control portion 61 drives the unspecified cassette 22 according to the driving stop condition (the status of the reverse rotation operation) when the dispensation of the tablets in the prescription amount predetermined by the prescription data terminates and then stops the driving of the unspecified cassette 22.

Specifically, in a case where the reverse rotation control in the driving correspondence information is set "ON," the control portion 61 carries out the reverse rotation operation for switching the conveying direction of the tablets by the second rotating body 224 to a reverse direction at the time of stopping the dispensation of the tablets form the unspecified cassette 22. For example, when the number of the tablets counted by the counter having the optical sensor (not shown in the drawings) provided at the dispensing port 225 reaches the dispensed amount, the control portion 61 allows the driving motor 242 to rotate in a reverse direction for a predetermined period which is set in advance. With this configuration, in a case where tablets having shapes easily likely to be rotated are put on the second rotating body 224, it is possible to prevent the tablets from being extra dispensed from the dispensing port 225. Further it is possible to take another configuration in which an opening closing shutter is provided at the dispensing port 225 and the shutter is closed when the number of the tablets counted by the counter reaches the dispensed amount.

On the other hand, in a case where the reverse rotation control in the driving correspondence information is set "OFF," the control portion 61 does not carry out the reverse rotation operation, which is unnecessary in this case, at the time of stopping the dispensation of the tablet form the unspecified cassette 22. Timing for starting the reverse rotation operation may be the time when the number of the tablets counted by the counter reaches a number which is less than the dispensed amount by a predetermined number. In the case of starting the reverse rotation operation at this timing, the predetermined numbers corresponding to each of the medicine information are stored in the driving correspondence information 122 in advance. This makes it possible to start the reverse rotation operation before the number of the tablets counted by the counter reaches the dispensed amount, and thereby preventing the tablets from being extra dispensed from the dispensing port 225. Further, the reverse rotation operation may be carried out each time one tablet is dispensed after the number of tablets counted by the counter reaches a number less than the dispensed amount by the predetermined number.

In this embodiment, the configuration in which the height h1 of the height restriction member 226 of the unspecified cassette 22 and the width w1 of the width restriction member 227 of the unspecified cassette 22 are changed according the driving condition at the step S4 is described as one example. On the other hand, another configuration in which the control portion 61 changes the height h1 of the height restriction member 226 and the width w1 of the width restriction member 227 just before the packaging operation is started at the step S7 may be considered as another embodiment. Namely, the reflection of the previous driving condition to the unspecified cassette 22 may be carried out at any timing as long as the reflection is carried out before the packaging operation is started.

(Packaging Control Unit 6 Side: Step S15)

Then, when the packaging operation completes at the step 14, the control portion 61 transmits a completion report of the packaging operation to the control portion 11 at a subsequent step S15.

(Prescription Control Unit 1 Side: Step S8)

In contrast, in the prescription control unit 1, the control portion 11 waits for the completion report of the packaging operation from the control portion 61 (the case of determining "No" at the step S8). When the control portion 11 receives the completion report of the packaging operation, the control portion 11 shifts the process to a step S9.

(Prescription Control Unit 1 Side: Step S9)

At the subsequent step S9, the control portion allows the display portion 25 of the unspecified cassette 22 which completes the dispensation to display an indication of "dispensation completion."

Figure 12B:

FIG. 12(B) is a view showing a display example of the dispensation completion. In the display example shown in FIG. 12(B), a large cross mark is displayed on all over the display portion 25 while the medicine information is displayed on the display portion 25. This makes it possible to report the user that the dispensation of the tablets from the unspecified cassette 22, on which the display portion 25 is provided, completes. As shown in FIG. 12(B), in the case where the cross mark, which indicates the dispensation completion and is displayed on the display portion 25, does not overlap the JAN code, it is possible to read the JAN code with the barcode reader 7 or the like after the dispensation completion.

Further, other configurations in which words "dispensation complete" are displayed on the display portion 25 and the medicine information is deleted from the display portion 25 may be considered as other display examples of the display portion 25.

(Prescription Control Unit 1 Side: Step S10)

The tablets should not remain in each of the unspecified cassettes 22 used in the packaging operation after the packaging operation is completed. However, in a case where the tablets in an extra amount are supplied into the unspecified cassette 22 by the user by mistake or in an intended manner, the tablets remaining in the unspecified cassette 22 would be dispensed when the unspecified cassette 22 is subsequently used. Thus, it is necessary to collect the tablets remaining in the unspecified cassette 22 in this case.

For the purpose of collecting the tablets, at a step S10, the control portion 11 transmits a carrying out request for a remaining medicine collecting process for discharging the tablets from the unspecified cassette 22 used in the packaging operation to the control portion 61. In a case where the unspecified cassette 22 has not been used in the packaging operation, the control portion 11 does not transmit the carrying out request for the remaining medicine collecting process to the control portion 61. The control portion 11 may allow the monitor 13 to display a selection screen for selecting whether or not the carrying out request for the remaining medicine collecting process regarding the unspecified cassette 22 used in the packaging operation should be transmitted to the control portion 61. Thus, the control portion 11 can switch whether or not the carrying out request for the remaining medicine collecting process should be transmitted to the control portion 61 depending on a user operation performed on the operating portion 14.

(Packaging Control Unit 6 Side: Step S16)

On the other hand, the control portion 61 determines whether or not the carrying out request for the remaining medicine collecting process is transmitted at a step S16. The control portion 61 shifts the process to a step S17 in a case where the control portion 61 receives the carrying out request for the remaining medicine collecting process from the control portion 11 (the case of determining "Yes" at the step S16). On the other hand, the control portion 61 shifts the process to the step S11 in a case where the control portion 61 does not receive the carrying out request for the remaining medicine collecting process from the control portion 11 (the case of determining "No" at the step S16).

(Packaging Control Unit 6 Side: Step S17)

At the step S17, the control portion 61 drives the first rotating body 223 and the second rotating body 224 of the unspecified cassette 22 for a predetermined period to carry out the remaining medicine collecting process for dispensing the tablets from the unspecified cassette 22. In this case, the control portion 61 carrying out the remaining medicine collecting process is one example of remaining medicine collecting means. At this time, the control portion 61 may change a discharge destination of the tablets dispensed from the unspecified cassette 22 from the packaging unit 5 to a medicine discharge tray (not shown in the drawings) provided in the medicine dispensing apparatus 100. With this configuration, in the case where the tablets remain in the unspecified cassette 22, it is possible to discharge the tablets to the medicine discharge tray during the predetermined period, and thereby preventing the tablets from remaining in the unspecified cassette 22. Further, the control portion 61 may allow the display portion 25 of the unspecified cassette 22 to display a message indicating that collection of the tablets from the unspecified cassette 22 completes after the control portion 61 drives the unspecified cassette 22 for the predetermined period. In this regard, for displaying the message indicating that the collection of the tablets from the unspecified cassette 22 completes, simple display means such as a LED which can display the message with a lighting method or a lighting color may be used.

Instead of discharging the tablets to the medicine discharge tray, the tablets remaining in the unspecified cassette 22 may be discharged in a state where the tablets are packaged in a sheet of packaging paper by the packaging unit 5. In this case, the control portion 61 may print, on the packaging paper, one or more of a medicine name, a medicine ID, a medicine code of the tablet, a JAN code, a patient name, a collection time and date and a name of a person in charge of collection by controlling a printing portion (not shown in the drawings) provided at the packaging unit 5. In a case where some types of tablets are collected from the plurality of unspecified cassettes 22, it is preferred that the tablets are separately packaged in different sheets of the packaging paper in correspondence with the types of tablets (that is, one sheet of the packaging paper does not contain some types of tablets but contains only one type of tablet). With this configuration, the control portion 61 can collate the JAN codes on the sheets of the packaging paper read by the barcode reader 7 with JAN codes written on the tablet containers placed on the medicine shelf, to which the types of tablets should be separately returned. Thus, the user can surely return the tablets packaged in the sheets of the packaging paper to the medicine shelf. The control portion 61 allows the monitor 13 of the prescription control unit 1 to display a collation result and store the collation result in the storage portion 12 as a return history of the tablet. Further, the collation result may be displayed by using not only the monitor 13 but also, for example, an audio output of a speaker (not shown in the drawings) provided in the medicine dispensing apparatus 100 or the barcode reader 7. Furthermore, in a case where an information processing apparatus such as a computer communicably connected to the medicine dispensing apparatus 100 is provided on the medicine shelf, the control portion 61 may allow a display portion provided in the information processing apparatus to display the collation result.

Further, there is possibility that a lot of tablets remain in the unspecified cassette 22 after the packaging operation completes. In this case, there is a risk that one sheet of the packaging paper cannot contain all of the tablets. Thus, in a case of collecting the tablets remaining in the unspecified cassette 22 with the packaging paper 52, the tablets remaining in the unspecified cassette 22 may be packaged in one sheet of the packaging paper 52 in units of predetermined number. In a case where the number of the tablets collected from the unspecified cassette 22 reaches the predetermined number, the control portion 61 may stop the remaining medicine collecting process. This makes it possible to suppress waste of time for collecting the tablets and waste of the packaging paper 52. In this case, the control portion 61 transmits a control signal indicating that a lot of tablets remain in the unspecified cassette 22 to the control portion 11. With this configuration, the control portion can recognize that the remaining medicine collecting process is stopped because the number of the tablets remaining in the unspecified cassettes is equal to or larger than the predetermined number, and then the control portion 11 can report the user this event with, for example, the monitor 13.

As described above, with the medicine dispensing apparatus 100, the user can automatically dispense desired types of tablets, which are not contained in the specified cassettes 21 in advance, only by respectively supplying the types of tablets into the unspecified cassettes 22 in bulk. Therefore, it is possible to reduce a user work compared with the conventional case where it is necessary to manually supply tablets into each of the boxes of the manual packaging unit 4, and thereby preventing user's human errors at the time of supplying the tablets.

Further, since the plurality of unspecified cassettes 22 are provided in the medicine dispensing apparatus 100, the medicine dispensing apparatus 100 can allocate various different medicine information to each of the unspecified cassettes 22. Thus, even if types of tablets which are not contained in the specified cassettes 21 are designated to be dispensed by the prescription data, the medicine dispensing apparatus 100 can carry out the packaging operation with the plurality of unspecified cassettes 22 on the basis of the prescription data. Further, the medicine dispensing apparatus 100 can continuously carry out a plurality of packaging operations based on a plurality of prescription data with the plurality of unspecified cassettes 22.

[Preparing Method with the Medicine Dispensing Apparatus 100]

Here, a concrete example of a preparing method carried out by the user with the medicine dispensing apparatus 100 will be described. Hereinafter, a case of preparing prescription data LP1, which contains one type of tablet contained in the specified cassette 21 and two types of tablets not contained in the specified cassettes 21 as prescription medicines, will be described as one example of the method.

First, the user operates the operating portion 14 to select the prescription data LP1 inputted into the medicine dispensing apparatus 100 and carry out an issuing operation for issuing the prescription data 100. With this configuration, in the medicine dispensing apparatus 100, the medicine information of the two types of tablets which are not contained in the specified cassettes 21 but contained in the prescription data LP1 are allocated to two of the unspecified cassettes 22 which have not yet been subjected to the allocation. At this time, the height h1 of the height restriction member 226 and the width w1 of the width restriction member 227 of each of the unspecified cassettes 22 are also changed according to the driving condition corresponding to the medicine information. Then, the medicine information allocated to each of the unspecified cassettes 22 is displayed on the display portion 25 of each of the unspecified cassettes 22.

Next, the user removes the unspecified cassette from the medicine dispensing apparatus 100 with confirming the medicine information displayed on the display portion 25. Then, the user supplies the tablets taken from the medicine shelf into the unspecified cassette in a required amount and then mounts the unspecified cassette 22 on the mounting portion 221 of the medicine dispensing apparatus 100. This work is carried out to the two unspecified cassettes 22. At this time, the user may collate the tablet designated by the medicine information displayed on the display portion 25 with the tablet taken from the medicine shelf by utilizing a collation function of the medicine dispensing apparatus 100 described below.

Next, the user operates the operating portion 14 to carry out a supplying complete operation indicating that the supplying of the tablets to each of the unspecified cassettes 22 completes. This allows the medicine dispensing apparatus 100 to dispense, on the basis of the prescription data LP1, the one type of tablet contained in the specified cassette 21 and the two types of tablets contained in the two unspecified cassettes 22 in the units of packages according to various information such as the administration time to package the tablets in the sheets of the packaging paper in the units of packages.

[Other Functions of the Medicine Dispensing Apparatus 100]

Hereinafter, description will be given to other functions of the medicine dispensing apparatus 100. It is noted that realization approaches for various functions described below are merely examples and the realization approaches are not limited to the following approaches as long as they can provide the similar functions.

[Collating Function at the Time of Supplying Tablets]

The medicine dispensing apparatus 100 has a collating function of collating the tablet taken from the medicine shelf by utilizing a JAN code (barcode) to be displayed on the display portion 25. Specifically, the user reads the JAN code displayed on the display portion 25 and the JAN code written on a tablet container or a PTP sheet taken from the medicine shelf with the barcode reader 7. This allows the control portion 11 to collate information of both of the JAN codes read by the barcode reader 7 with each other. Then, the control portion 11 allows the monitor 13 of the prescription control unit 1 to display a collation result. For example, in a case where the prescription data is displayed on the monitor 13 of the prescription control unit 1, the control portion 11 may give a color to a displaying screen for the medicine information, which has the collation result "matched," among the medicine information contained in the prescription data for indicating that the collation result is "matched."

As described above, since the medicine dispensing apparatus 100 can collate the tablet designated by the medicine information allocated to the unspecified cassette 22 with the tablet supplied into the unspecified cassette 22, it is possible to suppress user's human errors at the time of supplying the tablet into the unspecified cassette 22. In a configuration in which the JAN code is not displayed on the display portion 25, the control portion 11 may collate whether or not the JAN code read from the tablet container or the PTP sheet by the barcode reader 7 matches the tablet designated by the medicine information contained in the prescription data.

[Function of Using the Unspecified Cassette 22 as a Specified Cassette]

The medicine dispensing apparatus 100 has a function of using the unspecified cassette 22 in the same manner as the specified cassette 21.

Specifically, the control portion 11 allows the monitor 13 to display an initial setting screen for setting the medicine information corresponding to each of the unspecified cassettes 22 in advance when a predetermined specific operating input is carried out to the operating portion 14. Then, when an operating input for selecting the medicine information corresponding to one of the unspecified cassettes 22 is carried out, the control portion 11 allocates the selected medicine information to the unspecified cassette 22. At this time, the control portion 11 changes the driving conditions for the unspecified cassette 22 and allows the display portion 25 to display the medicine information in the same manner as the step S4 and the step S5 of the medicine dispensing process. Further, the control portion 11 allows the display portion 25 of the unspecified cassette 22 to display a tablet specifying screen for indicating that the type of tablet to be dispensed is specified.

Figure 12C:

FIG. 12(C) is a view showing one example of the tablet specifying screen. In the example shown in FIG. 12(C), a medicine name, a medicine ID of tablet and a JAN code are displayed on the display portion 25 and a black frame 251 is also displayed on a marginal region of the display portion 25 as the tablet specifying display. Further, a configuration in which a word "specified" is displayed, a predetermined mark for indicating that the unspecified cassette 22 becomes a specified state is displayed or a black and white presentation is reversed may be considered as another example of the tablet specifying screen.

In this manner, the unspecified cassette 22 to which the corresponding medicine information is set at the initial setting screen in advance (hereinafter, such a unspecified cassette 22 is referred to as "pseudo specified cassette 22A") is excluded from allocation objects at the step S3 in the medicine dispensing process.

Specifically, the control portion 11 updates an allocation state of the pseudo specified cassette 22A in the allocation information 122 stored in the storage portion 12 to "specified." With this configuration, the control portion 11 excludes the pseudo specified cassette 22A from the candidates for the unspecified cassettes 22 to which the medicine information can be allocated at the step S3 in the medicine dispensing process.

Needless to say, the control portion 11 can return the allocation state of the unspecified cassette 22 to an initial state by canceling the allocation of the medicine information to the pseudo specified cassette 22A according to an operating input inputted to the operating portion 14 at the initial setting screen.

As described above, the medicine dispensing apparatus 100 can use the unspecified cassette 22 in the same manner as the specified cassette 21 as required. Thus, for example, the user who uses the unspecified cassettes 22 with low frequency of use can efficiently utilize such an unspecified cassette 22 as the pseudo specified cassette 22A. Further, in a case where the medicine dispensing apparatus 100 takes a configuration in which the medicine dispensing apparatus 100 does not have the specified cassettes 21 and has only the unspecified cassettes 22, it is possible to arbitrarily set a balance between advantages of the specified cassettes 21 and advantages of the unspecified cassettes 22, and thereby improving flexibility of this system.

At the step S9 in the medicine dispensing process, the dispensing completion is displayed on the display portion 25 of the unspecified cassette 22 when the dispensation of the tablets from the unspecified cassette 22 completes. In contrast, in the case of utilizing the unspecified cassette 22 as the pseudo specified cassette 22A, the pseudo specified cassette 22A is used in subsequent packaging operations in the same manner as the specified cassette 21 even after the dispensation of the tablets from the pseudo specified cassette 22A completes. Thus, for the pseudo specified cassette 22A among the unspecified cassettes 22, the control portion 11 does not allow the display portion 25 to display the dispensation completion even when the dispensation completes.

[Cassette Recognizing Function]

The medicine dispensing apparatus 100 has a cassette recognizing function for easily recognizing the unspecified cassette 22 into which the tablet should be supplied at the time of supplying the tablet into the unspecified cassette 22. Specifically, when one of the medicine information contained in the prescription data displayed on the monitor 13 is selected by the user operation, the control portion 11 changes the display state of the display portion 25 of the unspecified cassette 22 to which this medicine information is allocated. For example, the control portion 11 may blink the display screen of the display portion 25 or reversing a black/white part of the display screen of the display portion 25.

Thus, the user can visually inspect and confirm the display portion 25 to easily recognize the unspecified cassette 22 into which the tablet should be supplied. In this regard, a light emitting portion such as a LED may be provided at each of the unspecified cassettes 22 or each of the mounting portions 221 of the unspecified cassettes 22 and the control portion 11 may change a lighting method (lighting or blinking method) or a lighting color of the light emitting portion.

[Status Display Function]

The medicine dispensing apparatus 100 has a status display function of allowing the display portion 25 of each of the unspecified cassettes 22 to display working information indicating a working status of each of the unspecified cassettes 22.

Specifically, the control portion 11 allows the display portion 25 to display the working status of the unspecified cassette 22. For example, in a case where the medicine information is not allocated to the unspecified cassette 22, the control portion 11 allows the display portion 25 to display a working status "not allocated." In another case where the medicine information is allocated to the unspecified cassette 22, the control portion 11 allows the display portion 25 to display a working status "already allocated." In other case where the driving conditions of the unspecified cassette 22 are being changed, the control portion 11 allows the display portion 25 to display a working status "under calibration." In other case where the packaging operation with the unspecified cassette 22 is being carried out, the control portion 11 allows the display portion 25 to display a working status "under dispensation." In the other case where the packaging operation is completed, the control portion 11 allows the display portion 25 to display a working status "dispensation completion." In this case, the control portion 11 carrying out this display process is one example of display control means. With this configuration, the user can easily recognize the working status of each of the unspecified cassettes 22 by visually inspecting and confirming the display portion 25 of each of the unspecified cassettes 22. In this regard, a display method for a variety of the status information may be a method using words, but it is possible to use various display styles such as a display mark, a numeric character and blinking for the display method.

[Calibration Function]

The medicine dispensing apparatus 100 has a calibration function of registering the height and the width of the dispensing path, which are the previous driving conditions for dispensing the tablets from the unspecified cassette 22 one by one.

Specifically, the control portion 11 carries out the calibration process depending on a carrying out request for a calibration process in the initial setting of the medicine dispensing apparatus 100. In a case where the control portion 11 determines that the height and the width of the dispensing path corresponding to the medicine information are not registered in the driving correspondence information 122 at the step S4, the control portion 11 may allow the monitor 13 to display a screen for selecting whether or not the calibration process should be carried out depending on a user operation performed on the operating portion 14. The calibration process may be carried out by the control portion 61.

In the calibration process, the control portion first allows the monitor 13 to display a selection screen for selecting one of the unspecified cassettes 22 to select the unspecified cassette 22 to be used in the calibration process depending on a user operation performed on the operating portion 14. Then, once the one of the unspecified cassettes 22 has been selected, the control portion 11 allows the monitor 13 to display a message indicating that tablets should be supplied into the selected unspecified cassette 22 and then waits for a supplying complete operation of the tablets inputted by a user operation performed on the operating portion 14.

After the supplying complete operation is carried out, the control portion 11 drives the height adjusting portion 226A and the width adjusting portion 227A of the selected unspecified cassette 22 to change the height h1 restricted by the height restriction member 226 to a predetermined minimum size and the width w1 restricted by the width restriction member 227 to a predetermined maximum size. Then, the control portion 11 drives the first rotating body 223 and the second rotating body 224. At this time, since the height h1 becomes the minimum size, the conveying of the tablets on the second rotating body 224 is restricted by the height restriction member 226.

Subsequently, the control portion 11 controls the height adjusting portion 226A in a state where the first rotating body 223 and the second rotating body 224 are driven to gradually increase the height h1 restricted by the height restriction member 226. At this time, since the width w1 restricted by the width restriction member 227 becomes the maximum size, the tablets passing through the height restriction member 226 are conveyed toward the dispensing port 225. Then, when the height h1 reaches to a height dimension of one tablet contained in the tablet containing portion 223, the tablet is dispensed from the dispensing port 225 through the height restriction member 226. The control portion 11 stops the driving of the first rotating body 223 and the second rotating body 224 when the dispensation of the tablet from the dispensing port 225 is detected by the optical sensor (not shown in the drawings) provided at the dispensing port 225. At this time, the control portion 11 registers a value of the height h1 corresponding to a driving time period of the height adjusting portion 226A until passing of the tablet is detected by the optical sensor (not shown in the drawings) as the driving condition corresponding to the medicine information on the tablet. Needless to say, the driving time period itself may be registered as the driving condition.

Next, the control portion 11 controls the width adjusting portion 227A to change the width w1 restricted by the width restriction member 227 to a predetermined minimum size and then drives the first rotating body 223 and the second rotating body 224. At this time, since the height h1 is set so that the tablet can pass through the height restriction member 226, the tablet on the second rotating body 224 is conveyed toward the width restriction member 227. On the other hand, since the width w1 becomes the minimum size, the conveying of the tablets on the second rotating body 224 is restricted by the width restriction member 227. Subsequently, the control portion 11 controls the width adjusting portion 227A in the state that the first rotating body 223 and the second rotating body 224 are driven to gradually increase the width w1 restricted by the width restriction member 227. When the width w1 reaches to a width of one tablet contained in the tablet containing portion 223, the tablet is dispensed from the dispensing port 225 through the width restriction member 227. The control portion 11 stops the driving of the first rotating body 223 and the second rotating body 224 when the dispensation of the tablet from the dispensed port 225 is detected by the optical sensor (not shown in the drawings) provided at the dispensing port 225. At this time, the control portion 11 registers a value of the width w1 corresponding to a driving time period of the width adjusting portion 227A until passing of the tablet is detected by the optical sensor (not shown in the drawings) as the driving condition corresponding to the medicine information on the tablet. Needless to say, the driving time period itself may be registered as one of the driving conditions.

As described above, the medicine dispensing apparatus 100 can automatically register the previous driving condition for the medicine information whose previous driving condition is not registered in the driving correspondence information 122 by means of the calibration function.

Second Embodiment

In this second embodiment, another example of the medicine dispensing process carried out by the control portion 11 will be described with reference to FIG. 13. Specifically, in the medicine dispensing process according to this embodiment (see left side of FIG. 13), medicine information read by the barcode reader 7 is inputted as the medicine information on the tablet to be dispensed and allocated to one of the unspecified cassettes 22. Hereinafter, procedures (steps) carried out by the control portion 11 will be referred to as a step S21, S22 . . . . The same procedures as the procedures of the medicine dispensing process and the packaging control process shown in FIG. 11 are respectively numbered by the same numerical numbers and description to the same procedures is omitted.

(Step S21)

First, at a step S21, the control portion 11 determines whether or not a JAN code is inputted from the barcode reader 7 as the medicine information on the tablet to be dispensed. Namely, the user first takes the tablets from the medicine shelf with referring to the prescription sheet in which the prescription data is written and then reads the medicine information on the tablet from the tablet container or the PTP sheet by means of the barcode reader 7 instead of first carrying out the issuing operation for issuing the prescription data.

At this time, the control portion 11 shifts the process to a step S25 until the medicine information on the tablet to be dispensed is inputted from the barcode reader (the case of determining "No" at the step S21). On the other hand, the control portion 11 shifts the process to a step S22 in a case where the medicine information on the tablet to be dispensed is inputted from the barcode reader 7 (the case of determining "Yes" at the step S21).

(Step S22)

Next, at the step S22, the control portion 11 allocates the medicine information on the tablet to be dispensed, which is inputted at the step S21, to one of the unspecified cassettes 22 which has not yet been subjected to the allocation. In this case, the control portion 11 carrying out this process for allocating the medicine information to one of the unspecified cassettes 22 when the medicine information on the tablet to be dispensed is inputted form the barcode reader 7 is one example of allocating means. In this regard, since the allocation to the unspecified cassette 22 is carried out in the same manner as the step S3 (see FIG. 11), description to the allocation to the unspecified cassette 22 is omitted.

The control portion 11 may determine whether or not the specified cassette 21 corresponding to the medicine information inputted at the step S21 exists. In this case, the control portion 11 may carry out subsequent procedures after the step S22 only in a case where any specified cassette 21 corresponding to the medicine information does not exist. On the other hand, in a case where the specified cassette 21 corresponding to the medicine information exists, the control portion 11 may allow the monitor 13 of the prescription control unit 1 to display a message indicating that the specified cassette 21 exists and then return the process to the step S21.

(Steps S23 and S24)

At steps S23 and S24, the control portion 11 carries out the same procedures as the steps S4 and S5 (see FIG. 11). Namely, the control portion 11 transmits the driving conditions for each of the unspecified cassettes 22 to which the medicine information is allocated at the step S22 to the control portion 61 together with the cassette identification information for each of the unspecified cassettes 22 (step S23). Further, the control portion 11 allows the display portion 25 of each of the unspecified cassettes 22 to which the medicine information is allocated to display the medicine information allocated to each of the unspecified cassettes 22 and the like (step S24).

(Step S25)

Then, at a step S25, the control portion 11 determines whether or not the issuing request for the prescription data is issued in the same manner as the step S1 (see FIG. 11). Specifically, the control portion 11 determines that the issuing request is issued when the predetermined issuing operation for issuing the prescription data is carried out to the operating portion 14.

The control portion 11 returns the process to the step S21 in a case where the control portion 11 determines that the issuing request for the prescription data is not issued (the case of determining "No" at the step S25). On the other hand, the control portion 11 shifts the process to the step S6 to carry out the subsequent procedures in a case where the control portion 11 determines that the issuing request for the prescription data is issued (the case of determining "Yes" at the step S25). In this regard, it is possible to take another configuration in which the mounting and removing detection sensor for detecting the mounting and the removing of the unspecified cassette 22 is provided at the mounting portion 221 and the control portion 11 reports that the supplying of the tablet into the unspecified cassette 22 is not carried out on the basis of the detection result of the mounting and removing detection sensor. Namely, the control portion 11 reports an error to the user when the issuing operation for the prescription data is carried out in a state where the mounting and removing of the unspecified cassette 22 is not detected by the mounting and removing detection sensor during the time period from allocating the medicine information to the unspecified cassette 2 to carrying out the issuing operation. The reporting is carried out by, for example, reporting means such as the monitor 13 or the speaker (not shown in the drawings).

[Preparing Method with the Medicine Dispensing Apparatus 100 According to the Second Embodiment]

Here, a concrete example of a preparing method according to the second embodiment which is carried out by the user with the medicine dispensing apparatus 100 will be described. Hereinafter, the case of preparing the prescription data LP1, which contains one type of tablet contained in the specified cassette 21 and two types of tablets not contained in the specified cassettes 21 as prescription medicines, will be described as one example of the method.

First, the user reads the JAN codes of the two types of tablets not contained in the specified cassettes 21 from the tablet containers or the PTP sheets placed on the medicine shelf, in which the two types of tablets are respectively contained, by means of the barcode reader 7. With this configuration, in the medicine dispensing apparatus 100, the medicine information on the two types of tablets among the medicine information contained in the prescription data LP1, which are not allocated to the specified cassettes 21, is respectively allocated to two of the unspecified cassettes 22. At this time, the medicine information allocated to the two unspecified cassettes 22 is displayed on the display portions 25 of the two unspecified cassettes 22.

Next, the user confirms the medicine information displayed on the display portions 25 to remove the unspecified cassettes 22 from the medicine dispensing apparatus 100. Then, the user supplies the tablets taken from the medicine shelf into each of the unspecified cassettes 22 in a required amount and then mounts the unspecified cassettes 22 on the mounting portions 221 of the medicine dispensing apparatus 100. This work is carried out to each of the two unspecified cassettes 22.

Then, the user selects the prescription data LP1 inputted in the medicine dispensing apparatus 100 by operating the operating portion 14 to carry out the issuing operation for the prescription data LP1. As a result, in the medicine dispensing apparatus 100, the one type of tablet contained in the specified cassette 21 and the two types of tablets respectively contained in the two unspecified cassettes 22 are dispensed to the packaging unit 5 in the units of packages according to various information such as the administration time and then the packaging unit 5 packages the tablets into sheets of the packaging paper in the units of packages.

Third Embodiment

In this third embodiment, a medicine dispensing apparatus 300 which is a modified example of the medicine dispensing apparatus 100 described in the first embodiment will be described. The same matters as the medicine dispensing apparatus 100 are omitted from description to the medicine dispensing apparatus 300.

The medicine dispensing apparatus 300 includes an RFID reader writer 28 provided at a placing table of the medicine shelf on which tablets not yet supplied into the unspecified cassette 22 are placed. The RFID reader writer 28 has a wireless communication function of carrying out data communication with the prescription control unit 1 of the medicine dispensing apparatus 300 through the communication IF 15 with wireless communication. The RFID reader writer 28 detects the RFID tag 26 of the unspecified cassette 22 to detect that the unspecified cassette 22 is placed on the placing table and then report a detection result to the prescription control unit 1. The RFID reader writer 28 also receives information transmitted from the prescription control unit 1 to write the information into the RFID tag 26.

Positions where the RFID tag 26 and the RFID reader writer 28 are provided on each of the unspecified cassette 22 and the placing table may be relatively set so that the RFID tag 26 and the RFID reader writer 28 are positioned within an area in which the RFID reader writer 28 can read/write information of the RFID tag 26 in a state where the unspecified cassette 22 is placed on the placing table. Further, in a case where a information processing apparatus connected to the RFID reader writer 28 or the like is provided on the medicine shelf, a system containing the medicine dispensing apparatus 300 and the information processing apparatus may be considered as the medicine dispensing apparatus of the present invention.

In the medicine dispensing apparatus 300, a medicine allocating process (see FIG. 14) and a medicine dispensing process (see left side of FIG. 15), which are described below, are carried out by the control portion 11. The control portion 11 carries out procedures shown in FIGS. 14 and 15 in parallel.

Hereinafter, examples of the procedures of the medicine allocating process and the medicine dispensing process carried out by the control portion 11 in the medicine dispensing apparatus 300 will be described with reference to FIGS. 14 and 15. Hereinafter, the procedures (steps) carried out by the control portion 11 are referred to a step S31, S32 . . . and a step S41, S42 . . . . The same procedures as the procedures of the medicine dispensing process and the packaging control process shown in FIG. 11 are respectively numbered by the same numerical numbers and description to the same procedures is omitted.

Figure 14:
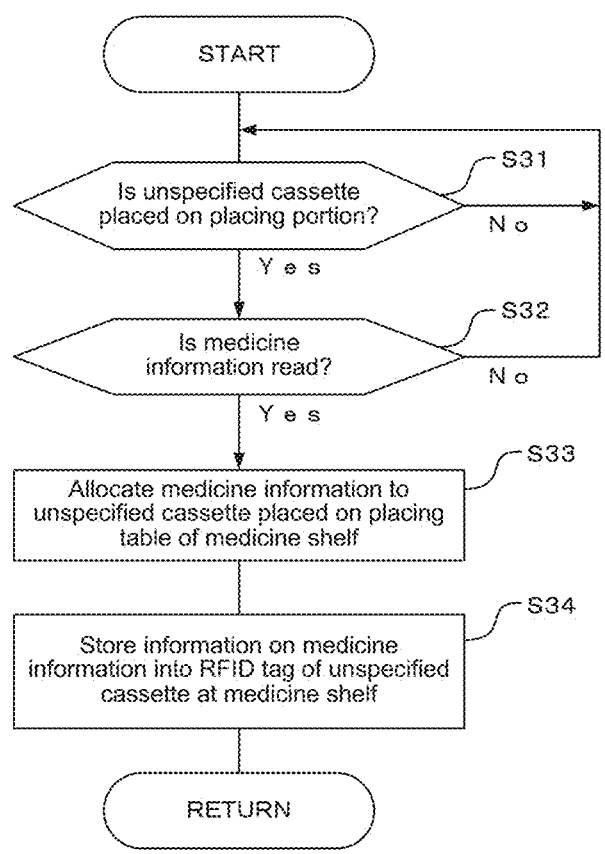
FIG. 14 is a flow chart for explaining one example of a procedure for a medicine allocating process.
Figure 15:
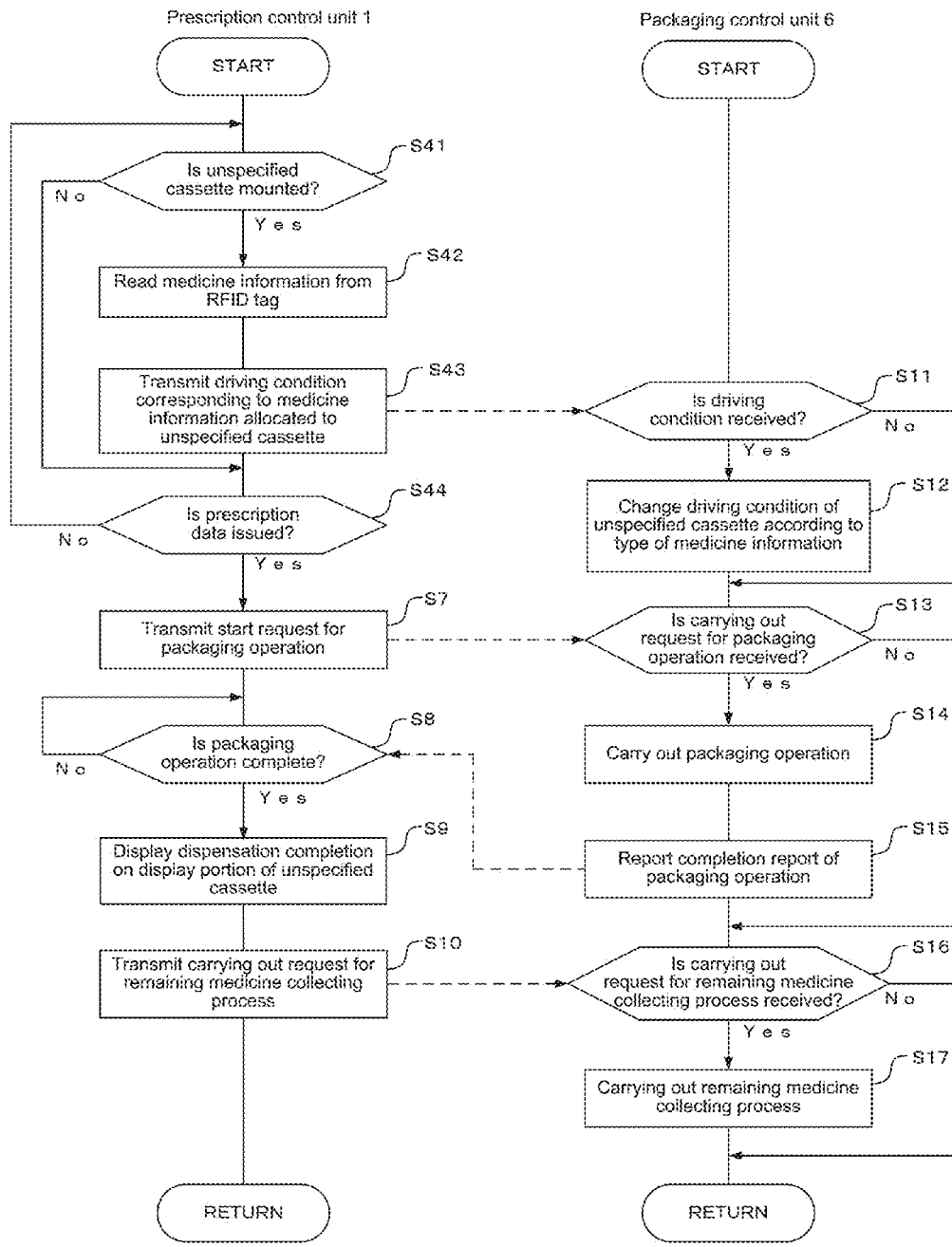
FIG. 15 is a flow chart for explaining other example of the procedure for the medicine dispensing process.

Further, another configuration in which the procedures shown in FIG. 14 are carried out by the information processing apparatus provided on the medicine shelf and the procedures shown in FIG. 15 are carried out by the control portion 11 of the medicine dispensing apparatus 300 may be considered as another embodiment. In this case, the information processing apparatus refers and edits the allocation information 121 stored in the storage portion 12 of the medicine dispensing apparatus 300.

[Medicine Allocating Process]

(Step S31)

First, at a step S31 in the medicine allocating process shown in FIG. 14, the control portion 11 determines whether or not the unspecified cassette 22 is placed on the placing table of the medicine shelf. Specifically, in a case where the RFID tag 26 of the unspecified cassette 22 is detected by the RFID reader writer 28, the control portion 11 determines that the unspecified cassette 22 is placed on the placing table. In the medicine dispensing apparatus 300, it is possible to take a configuration in which only the unspecified cassette 22 which has not yet been subjected to the allocation can be removed from the mounting portion 221 and the unspecified cassette 22 to which the medicine information has been already allocated cannot be removed from the mounting portion 221 with a mechanical rocking.

The control portion 11 holds the process on standby in a case where the unspecified cassette 22 is not placed on the placing table (the case of determining "No" at the step S31). On the other hand, the control portion shifts the process to a step S32 in a case where the unspecified cassette 22 is placed on the placing table of the medicine shelf (the case of determining "Yes" at the step S31).

(Step S32)

At the step S32, the control portion 11 determines whether or not the JAN code is read by the barcode reader 7 as the medicine information on the tablets to be dispensed in the same manner as the step S21 (see FIG. 13). Namely, the user takes the tablets from the medicine shelf or the like with referring to the prescription sheet in which the prescription data is written. Then, the user reads the medicine information on the tablet from the tablet container or the PTP sheet placed on the medicine shelf with the barcode reader 7.

At this time, the control portion 11 returns the process to the step S31 in a case where the control portion 11 determines that the medicine information on the tablets to be dispensed is not inputted from the barcode reader 7 (the case of determining "No" at the step S32). On the other hand, the control portion 11 shifts the process to a step S33 in a case where the control portion 11 determines that the medicine information on the tablets to be dispensed is inputted from the barcode reader 7 (the case of determining "Yes" at the step S32).

(Step S33)

At the step S33, the control portion 11 allocates the medicine information on the tablets to be dispensed, which is inputted at the step S32, to the unspecified cassette 22 placed on the placing table of the medicine shelf. In this case, the control portion 11 carrying out this process for allocating the medicine information to the unspecified cassette 22 when the medicine information on the tablet to be dispensed is read by the barcode reader 7 is also one example of the allocating means. At this time, the control portion 11 reflects the allocation state between the medicine information and the unspecified cassette 22 to the allocation information 121.

(Step S34)

Then, at a step S34, the control portion 11 carries out data communication with the RFID reader writer 28 through the communication IF 15 to store the medicine information into the RFID tag 26 of the unspecified cassette 22 placed on the placing table of the medicine shelf. At this time, in the unspecified cassette 22, the control board on which the RFID tag 26 is equipped allows the display portion 26 to fully or partially display the medicine information stored in the RFID tag 26 (see FIG. 12(A)).

[Medicine Dispensing Process]

(Step S41)

On the other hand, at a step S41 in the medicine dispensing process shown in FIG. 15, the control portion 11 determines whether or not the unspecified cassette 22 is mounted on the mounting portion 221 of the medicine dispensing apparatus 300. Namely, the control portion 11 determines whether or not a state of each of the mounting portions 221 is changed from a non-mounted state, in which the unspecified cassette 22 is not mounted on the mounting portion 221, to a mounted state. The control portion 11 determines whether or not the unspecified cassette 22 is mounted on the mounting portion 221 by detecting the RFID tag 26 of the unspecified cassette 22 with, for example, the RFID reader writer 245 provided at the mounting portion 221. Needless to say, it is possible to mechanically or optically detect the mounting of the unspecified cassette 22 with a mounting and removing detection sensor provided at the mounting portion 221.

At this time, the control portion 11 shifts the process to a step S44 in a case where the control portion 11 determines that the mounting of the unspecified cassette is not detected (the case of determining "No" at the step S41). On the other hand, the control portion 11 shifts the process to a step S42 in a case where the control portion 11 determines that the mounting of the unspecified cassette 22 is detected (the case of determining "Yes" at the step S41). The case where the control portion 11 determines that the mounting of the unspecified cassette 22 is not detected contains a case where the unspecified cassette 22 has been already mounted.

(Step S42)

Next, at the step S42, the control portion 11 reads the medicine information allocated to the unspecified cassette 22 from the RFID tag 26 of the unspecified cassette 22 whose mounting is detected at the step S41. At this time, the control portion 11 allows the monitor 13 to display an error indication and interrupts the medicine dispensing process in a case where there is a difference between the medicine information allocated to the unspecified cassette 22 and the contents of the allocation information 121. The control portion 11 may prioritize the medicine information read by the RFID reader writer 26 and update the allocation information 121.

(Step S43)

Then, at a step S43, the control portion 11 transmits the driving condition corresponding to the medicine information allocated to each of the unspecified cassettes 22 to the control portion 61 together with cassette identification information of each of the unspecified cassettes 22. With this configuration, the control portion 61 changes the height h1 restricted by the height restriction member 226 of the unspecified cassette and the width w1 restricted by the width restriction member 227 of the unspecified cassette 22 according to the previous driving condition in the driving condition corresponding to the medicine information allocated to the unspecified cassette 22.

(Step S44)

Then, at a step S44, the control portion 11 determines whether or not the issuing request for the prescription data is issued in the same manner as the step S25 (see FIG. 13). At this time, the control portion 11 returns the process to the step S41 in a case where the control portion 11 determines that the issuing request for the prescription data is not issued (the case of determining "No" at the step S44). On the other hand, the control portion 11 shifts the process to the step S7 in a case where the control portion 11 determines that the issuing request for the prescription data is issued (the case of determining "Yes" at the step S44). In the medicine dispensing process shown in FIG. 15, the step S6 is omitted because the supplying of the tablets into the unspecified cassette 22 is carried out on the medicine shelf in the medicine dispensing apparatus 300. However, the procedure of the step S6 may be carried out before the step S7.

[Preparing Method with the Medicine Dispensing Apparatus 300]

Here, a concrete example of a preparing method carried out by the user with the medicine dispensing apparatus 300 will be described. Hereinafter, the case of preparing the prescription data LP1, which contains one type of tablet contained in the specified cassette 21 and two types of tablets not contained in the specified cassettes 21 as prescription medicines, will be described as one example of the method.

First, the user removes two of the unspecified cassettes 22, which have not yet been subjected to the allocation, from the medicine dispensing apparatus 300 to bring the two unspecified cassettes 22 to the medicine shelf and places one of the two unspecified cassettes 22 on the placing table at which the RFID reader writer 28 is provided. Then, the user reads the JAN code of one of the two types of tablets not contained in the specified cassettes 21 from the tablet container or the PTP sheet placed on the container shelf (medicine shelf), in which the type of tablets are contained, by means of the barcode reader 7. With this configuration, in the medicine dispensing apparatus 300, the medicine information of the one type of tablets is allocated to the unspecified cassette 22 placed on the placing table of the medicine shelf. At this time, the medicine information is stored into the RFID tag 26 of the unspecified cassette 22 and the medicine information allocated to the unspecified cassette 22 is displayed on the display portion 25. Then, the user supplies the one type of tablets taken from the medicine shelf into the unspecified cassette 22 in a required amount.

Subsequently, the user places the other of the two unspecified cassettes 22 on the placing table at which the RFID reader writer 28 is provided. Then, the user reads the JAN code of the other of the two types of tablets not contained in the specified cassettes 21 from the tablet container or the PTP sheet placed on the container shelf (medicine shelf), in which the other type of tablets are contained, by means of the barcode reader 7. With this configuration, in the medicine dispensing apparatus 300, the medicine information on the other type of tablets is allocated to the unspecified cassette 22 placed on the placing table. At this time, the medicine information is stored into the RFID tag 26 of the unspecified cassette 22 and the medicine information allocated to the unspecified cassette 22 is displayed on the display portion 25. Then, the user supplies the other type of tablets taken from the medicine shelf into the unspecified cassette 22 in a required amount.

Then, the user mounts each of the unspecified cassettes 22 on each of the mounting portions 221 of the medicine dispensing apparatus 300. With this configuration, in the medicine dispensing apparatus 300, the medicine information stored in the RFID tag 26 of each of the unspecified cassettes 22 is retrieved.

Then, the user operates the operating portion 14 to select the prescription data LP1 inputted into the medicine dispensing apparatus 300 and carries out the issuing operation for the prescription data LP1. With this configuration, the medicine dispensing apparatus 300 can dispense, on the basis of the prescription data LP1, the one type of tablet contained in the specified cassette 21 and the two types of tablets contained in the unspecified cassettes 22 to the packaging unit 5 in the units of packages and package the tablets into the sheets of the packaging paper in the units of packages by means of the packaging unit 5.

Fourth Embodiment

Figure 16:
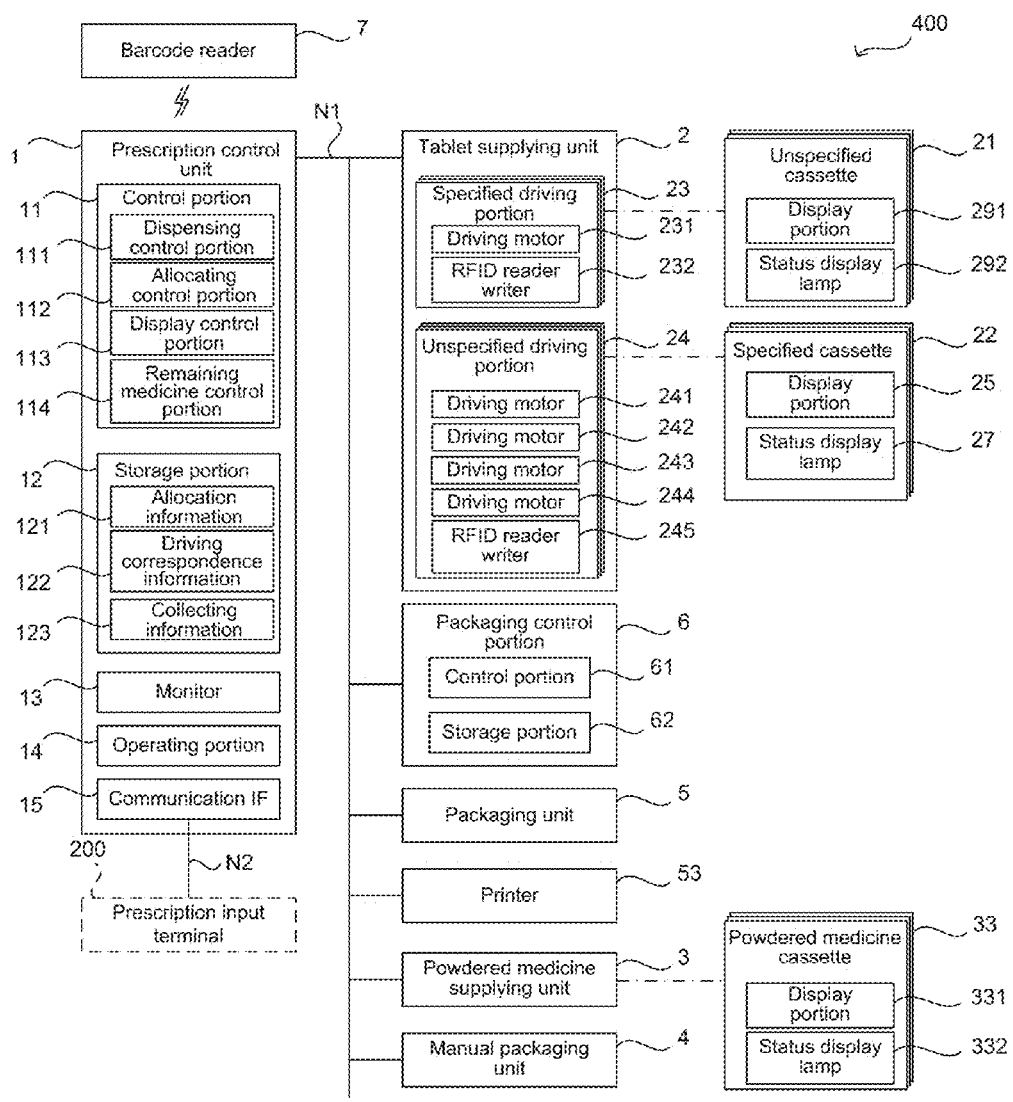
FIG. 16 is a block diagram for illustrating a system configuration of a medicine dispensing apparatus according to a fourth embodiment of the present invention.

FIG. 16 is a block diagram for illustrating a schematic configuration of a medicine dispensing apparatus 400 which is a modified example of the medicine dispensing apparatus 100 described in the description to the first embodiment. The same matters as the medicine dispensing apparatus 100 are omitted from description to the medicine dispensing apparatus 400. For example, in the medicine dispensing apparatus 400, since a subsequent prescription allocating process (see FIG. 17) described below is carried out, it is possible to improve work efficiency of the user using the medicine dispensing apparatus 400.

As shown in FIG. 16, the control portion 11 in the medicine dispensing apparatus 400 contains a dispensing control portion 111 and an allocating control portion 112. The control portion 11 carries out processes with the CPU depending on various programs preliminary stored in storage means such as the ROM, the EEPROM and the storage portion 12 to serve as the dispensing control portion 111 and the allocating control portion 112. The dispensing control portion 111 carries out the medicine dispensing process (see FIG. 11). The allocating control portion 112 carries out the subsequent prescription allocating process (see FIG. 17) described below. The medicine dispensing process and the subsequent prescription allocating process are carried out in substantially parallel.

[Subsequent Prescription Allocating Process]

Figure 17:
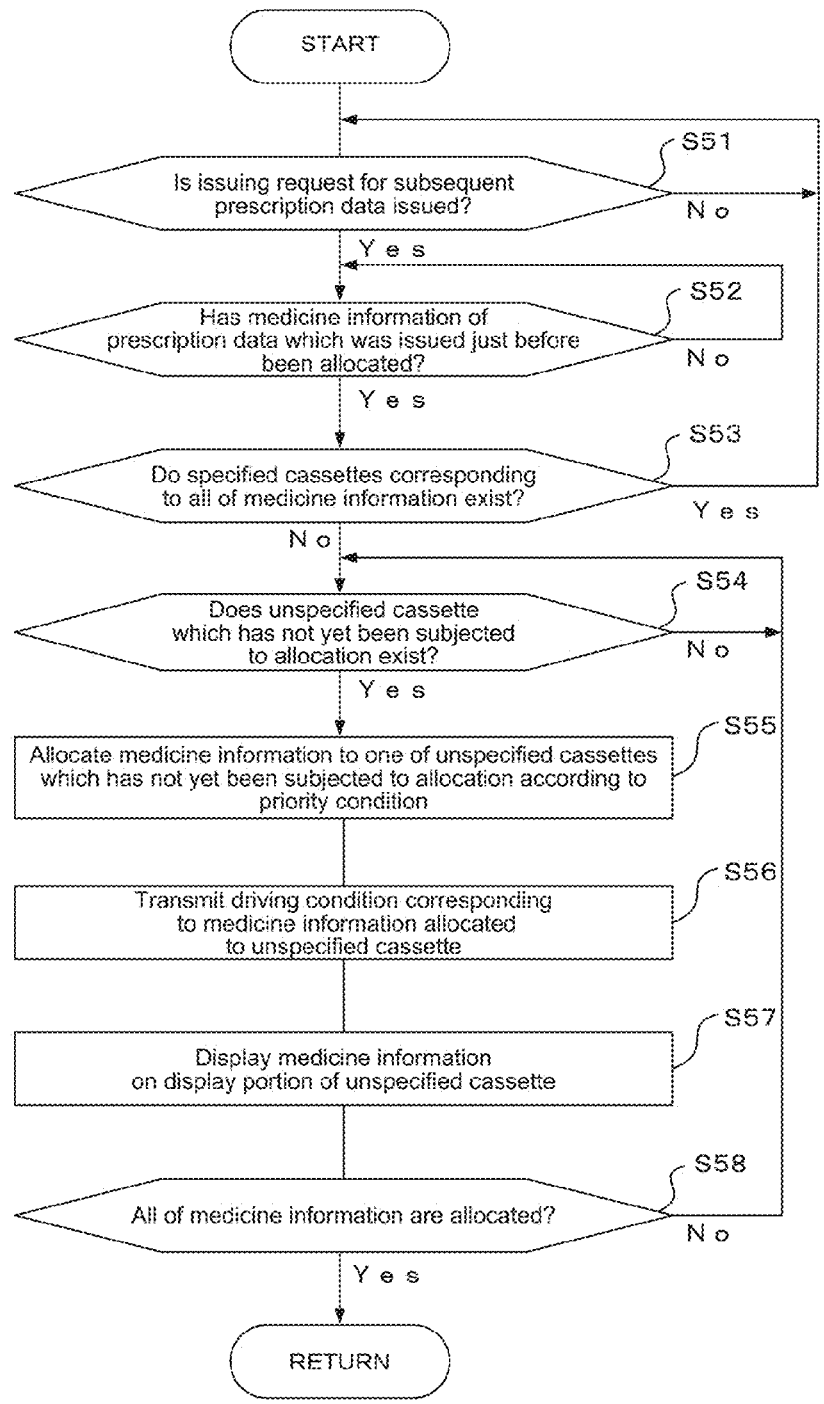
FIG. 17 is a flow chart for explaining one example of a procedure for a subsequent prescription allocating process.

The subsequent prescription allocating process is a process for controlling allocation of a subsequent prescription to one of the unspecified cassettes 22 when subsequent prescription data is issued in the medicine dispensing apparatus 400 before the dispensation of the medicine corresponding to the prescription data, which is previously issued, completes. FIG. 17 is a flow chart for explaining one example of a procedure for the subsequent prescription allocating process carried out by the allocating control portion 112 in the medicine dispensing apparatus 400.

<Step S51>

First, at a step S51, the allocating control portion 112 determines whether or not an issuing request for subsequent prescription data, which is subsequent to the prescription data currently issued, is issued. Hereinafter, the prescription data currently issued is referred to as "current prescription data" and the prescription data subsequent to the current prescription data is referred to as "subsequent prescription data." The allocating control portion 112 shifts the process to a step S52 in a case where the allocating control portion 112 determines that the issuing request for the subsequent prescription data is issued (the case of determining "Yes" at the step S51). On the other hand, the allocating control portion 112 holds the process at the step S51 on standby in a case where the issuing request for the subsequent prescription data is not issued (the case of determining "No" at the step S51). In a configuration in which it is possible to simultaneously issue a plurality of issuing requests for a plurality of prescription data, the allocating control portion 112 shifts the process to the step S52 if the second or following prescription data issued in an issuing order exists. Further, the allocating control portion 112 shifts the process to the step S52 even in a case where other prescription data is issued subsequent to the subsequent prescription data in the same manner.

<Step S52>

At the step S52, the allocating control portion 112 determines whether or not the allocation of the medicine information contained in the current prescription data to the unspecified cassette 22 completes. The allocating control portion 112 shifts the process to a step S53 in a case where the allocating control portion 112 determines that the allocation of the medicine information completes (the case of determining "Yes" at the step S52). On the other hand, the allocating control portion 112 holds the process at the step S52 on standby until the allocation of the medicine information completes (the case of determining "No" at the step S52). The allocating control portion 112 shifts the process to the step S51 when the dispensation of the tablet corresponding to the current prescription data completes while the allocating control portion 112 holds the process at the step S52 on standby.

<Step S53>

At the step S53, the allocating control portion 112 determines whether or not there exist the specified cassettes 21 corresponding to all of the medicine information on the tablet designated to be dispensed by the inputted subsequent prescription data. Namely, at the step S53, the allocating control portion 112 determines whether or not the prescription medicines contained in the subsequent prescription data contain a type of tablet which is not contained in the specified cassettes 21. The allocating control portion 112 shifts the process to a step S54 in a case where the specified cassettes 21 corresponding to all of the medicine information contained in the subsequent prescription data do not exist (the case of determining "No" at the step S53). On the other hand, the allocating control portion 112 returns the process to the step S51 in a case where the control portion 112 determines that the specified cassettes 21 corresponding to all of the medicine information contained in the subsequent prescription data exist (the case of determining "Yes" at the step S53). Namely, the allocation of the medicine information to the unspecified cassettes 22 is determined as unnecessary in the case where all types of tablets to be dispensed by the subsequent prescription data as the prescription medicines are contained in the specified cassettes 21.

<Step S54>

At the step S54, the allocating control portion 112 determines whether or not the unspecified cassette 22 which has not yet been subjected to the allocation exists among the unspecified cassettes 22. The allocating control portion 112 can determine whether or not the unspecified cassette 22 which has not yet been subjected to the allocation exists by referring to the allocation information 121 (see FIG. 9). The allocating control portion 112 shifts the process to a step S55 in a case where the allocating control portion 112 determines that the unspecified cassette 22 which has not yet been subjected to the allocation exists (the case of determining "Yes" at the step S54). On the other hand, the allocating control portion 112 returns the process to the step S54 in a case where the allocating control portion 112 determines that the unspecified cassette 22 which has not yet been subjected to the allocation does not exist (the case of determining "No" at the step S54). Namely, the allocating control portion 112 holds the process at the step S54 on standby until the unspecified cassette 22 becomes a non-allocated state after the unspecified cassette 22 is used in a case where the medicine information which should be allocated to the unspecified cassette 22 exists and the unspecified cassette 22 which has not yet been subjected to the allocation does not exist. Then, the allocating control portion 112 shifts the process to a step S55 when the unspecified cassette 22 becomes the non-allocated state after the unspecified cassette 22 is used for the current prescription data which is previous to the subsequent prescription data (the case of determining "Yes" at the step S54). The allocating control portion 112 shifts the process to the step S51 in a case where the dispensation of the tablets corresponding to the current prescription data completes while the allocating control portion 112 holds the process at the step S54 on standby.

<Step S55>

At the step S55, the allocating control portion 112 allocates the medicine information, which is not contained in any specified cassette 21, to one of the unspecified cassettes 22 which has not yet been subjected to the allocation among the medicine information inputted from the subsequent prescription data. At this time, in a case where a plurality of medicine information which should be allocated to the unspecified cassettes 22 exist in the subsequent prescription data, the allocating control portion 112 allocates, according to a predetermined priority condition, one of the medicine information, which has the highest priority at this time among the plurality of medicine information which are not allocated to the unspecified cassettes 22, to the unspecified cassette 22 which has not yet been subjected to the allocation. Namely, every time the step S55 is carried out for the same subsequent prescription data, one of the medicine information having the highest propriety at that time is allocated to one of the unspecified cassettes 22.

Here, description will be given to the priority condition. For example, the allocating control portion 112 carries out the step S55 according to a priority condition selected from the group consisting of a first priority condition to a fourth priority condition (which are described below) in advance by a user operation performed on the operating portion 14 at the initial setting screen or the like. Further, it is possible to use a combination of two or more of the first priority condition to the fourth priority condition. For example, if two of the medicine information are individually selected as medicine information having the highest priority according to the second priority condition, it is possible to further prioritize the two of the medicine information according to the first priority condition.

FIGS. 18 to 21 are views showing transitions of the allocation information 121 when the first priority condition to the fourth priority condition are used. As described above, in the allocation information 121, the cassette numbers "C1" to "C4" as the cassette identification information are preliminarily set to the four unspecified cassettes 22 which are arranged in the tablet supplying unit 2 from left to right in this order. Further, in FIGS. 18 to 21, a medicine ID of the medicine information of the current prescription data is labeled by "RP1" and a medicine ID of the medicine information of the subsequent prescription data is labeled by "RP2."

<First Priority Condition>

First, as the first priority condition that is one example of the priority condition, it may be defined that medicine information listed uppermost in the prescription data should be preferentially allocated to the unspecified cassette 22. For example, it is assumed that three of the medicine information having the medicine IDs "M1," "M2" and "M3" are contained in the current prescription data and two of the medicine information having the medicine IDs "M4" and "M5" are contained in the subsequent prescription data. Here, the medicine information having the medicine ID "M4" is listed upper than the medicine information having the medicine ID "M5," and the dispensed amount contained in the medicine information having the medicine ID "M4" is 10 tablets and the dispensed amount contained in the medicine information having the medicine ID "M5" is 30 tablets.

In this case, as shown in FIG. 18(A), each of the medicine information having the medicine IDs "M1" to "M3" is allocated to the unspecified cassettes 22 having the cassette numbers "C1" to "C3." Then, as shown in FIG. 18(B), the medicine information, which has the medicine ID "M4" and is listed uppermost side in the prescription data, is first allocated to the unspecified cassette 22 having the cassette number "C4." Then, after the dispensations of the tablets of the medicine IDs "M1," "M2" and "M3" complete as shown in FIG. 18(C), the medicine information having the medicine ID "M5" is allocated to the unspecified cassette 22 which has the cassette number "C1" and becomes the non-allocated state as shown in FIG. 18(D). Thus, by using the first priority condition, it is possible to achieve an operation easily understandable for the user because an order of the allocations to the unspecified cassettes 22 coincides with the listing order of the medicine information in the subsequent prescription data.

<Second Priority Condition>

In addition, as the second priority condition that is another example of the priority condition, it may be defined that the medicine information having the largest dispensed amount among those contained in the subsequent prescription data should be preferentially allocated to the unspecified cassettes 22. For example, it is assumed that three of the medicine information having the medicine IDs "M1," "M2" and "M3" are contained in the current prescription data and two of the medicine information having the medicine IDs "M4" and "M5" are contained in the subsequent prescription data. Here, the medicine information having the medicine ID "M4" is listed upper than the medicine information having the medicine ID "M5." Further, the dispensed amount contained in the medicine information having the medicine ID "M4" is 10 tablets and the dispensed amount contained in the medicine information having the medicine ID "M5" is 30 tablets.

In this case, as shown in FIG. 19(A), each of the medicine information having the medicine IDs "M1" to "M3" is allocated to the unspecified cassettes 22 having the cassette numbers "C1" to "C3." Then, as shown in FIG. 19(B), the medicine information which has the medicine ID "M5" and the dispensed amount larger than that of the medicine information having the medicine ID "M4" is first allocated to the unspecified cassette 22 having the cassette number "C4." Then, after the dispensations of the tablets having the medicine IDs "M1," "M2" and "M3" complete as shown in FIG. 19(C), the medicine information having the medicine ID "M4" is allocated to the unspecified cassette 22 which has the cassette number "C1" and becomes the non-allocated state as shown in FIG. 19(D). Thus, by using the second priority condition, it is possible to supply the medicine corresponding to the medicine information, which has the medicine ID "M5" and the large dispensed amount, to the unspecified cassette 22 while the dispensation of the medicine designated by the current prescription data is carried out, and thereby improving the work efficiency of the user.

<Third Priority Condition>

Further, as the third priority condition that is a still another example of the priority condition, it may be defined that among the medicine information contained in the subsequent prescription data, medicine information that is not contained in the current prescription data should be preferentially allocated to the unspecified cassettes 22. For example, it is assumed that three of the medicine information having the medicine IDs "M1," "M2" and "M3" are contained in the current prescription data and two of the medicine information having the medicine IDs "M4" and "M2" are contained in the subsequent prescription data.

In this case, as shown in FIG. 20(A), each of the medicine information having the medicine IDs "M1" to "M3" is allocated to the unspecified cassettes 22 having the cassette numbers "C1" to "C3." Then, as shown in FIG. 20(B), the medicine information having the medicine ID "M4" is first allocated to the unspecified cassette having the cassette number "C4." Namely, the medicine information having the medicine ID "M4" other than the medicine information having the medicine ID "M2" contained in both the current prescription data and the subsequent prescription data is preferentially allocated to the unspecified cassette 22. Then, after the dispensations of the tablets of the medicine IDs "M1," "M2" and "M3" complete as shown in FIG. 20(C), the medicine information having the medicine ID "M2" is allocated to the unspecified cassette 22, which has the cassette number "C2" and to which the medicine information having the medicine ID "M2" was allocated, among the unspecified cassettes 22 having the cassette numbers "C1" to "C3" which become the non-allocated states as shown in FIG. 20(D). By using the third priority condition, it is possible to prevent a medicine having a color differing from that of a previous medicine from being supplied into the same unspecified cassette 22, and thereby preventing powder or the like of the previous medicine from adhering to a subsequent medicine.

<Fourth Priority Condition>

Further, as the fourth priority condition that is a further example of the priority condition, it may be defined that among the medicine information contained in the subsequent prescription data, medicine information that is also contained in the current prescription data should be preferentially allocated to the unspecified cassettes 22. For example, it is assumed that three of the medicine information having the medicine IDs "M1," "M2" and "M3" are contained in the current prescription data and two of the medicine information having the medicine IDs "M4" and "M2" are contained in the subsequent prescription data.

In this case, as shown in FIG. 21(A), each of the medicine information having the medicine IDs "M1" to "M3" is allocated to the unspecified cassettes 22 having the cassette numbers "C1" to "C3." Then, as shown in FIG. 21(B), the medicine information having the medicine ID "M2" contained in the subsequent prescription data is first allocated to the unspecified cassette having the cassette number "C4." Then, after the dispensations of the tablets having the medicine IDs "M1," "M2" and "M3" complete as shown in FIG. 21(C), the medicine information having the medicine ID "M4" contained in the subsequent prescription data is allocated to the unspecified cassette 22 which has the cassette number "C1" and becomes the non-allocated state as shown in FIG. 21(D). By using the fourth priority condition, at the time of supplying the medicine corresponding to the medicine information having the medicine ID "M2" and contained in the current prescription data into the unspecified cassette 22 having the cassette number "C2," it is possible to supply the same medicine into the unspecified cassette 22 having the cassette number "C4" and to which the medicine information having the medicine ID "M2" is allocated and contained in the subsequent prescription data (as shown in FIG. 21(B)), thereby improving the work efficiency of the user.

Further, another configuration in which the allocation of the medicine information contained in the subsequent prescription data to the unspecified cassette 22 may be carried out only in a case where the number of the unspecified cassettes 22 which have not yet been subjected to the allocations is equal to or more than the number of the medicine information contained in the subsequent prescription data which should be allocated to the unspecified cassettes 22 may be considered as another embodiment. In the medicine dispensing apparatus having such a configuration, the allocations to the unspecified cassettes 22 for one prescription data are not carried out at different timings. Thus, the user can supply the medicines into the unspecified cassettes 22 in a unit of the prescription data.

<Step S56>

Then, at the step S56, the allocating control portion 112 transmits the driving condition corresponding to the medicine information allocated to the unspecified cassette 22 at the step S55 to the control portion 61. The process at the step S56 is the same as the process at the step S4 (see FIG. 11).

<Step S57>

At a step S57, the allocating control portion 112 allows the display portion 25 of the unspecified cassette 22 to display the medicine information allocated to the unspecified cassette 22 at the step S55. With this configuration, the user can supply the medicine into the unspecified cassette 22. The process at the step S57 is the same as the process at the step S5 (see FIG. 11). In the subsequent allocating process described here, the allocating control portion 112 carries out the steps S56 and S57 every time the medicine information, which should be allocated to the unspecified cassette 22 among the medicine information contained in the subsequent prescription data, is allocated to one of the unspecified cassettes 22. On the other hand, the allocating control portion 112 may carry out the steps S56 and S57 when all of the allocations of the medicine information, which should be allocated to the unspecified cassettes 22 among the medicine information contained in the subsequent prescription data, to the unspecified cassettes 22 complete.

<Step S58>

Next, at a step S58, the allocating control portion 112 determines whether or not all of the medicine information, which do not correspond to the specified cassettes 21 among the medicine information contained in the subsequent prescription data, are allocated to the unspecified cassettes 22. At this time, the allocating control portion 112 returns the process to the step S51 in a case where the allocating control portion 112 determines that all of the medicine information, which do not correspond to the specified cassettes 21, are allocated to the unspecified cassettes 22 (the case of determining "Yes" at the step S58). On the other hand, the allocating control portion 112 shifts the process to the step S54 in a case where the allocating control portion 112 determines that all of the medicine information, which do not correspond to the specified cassettes 21, are not allocated to the unspecified cassettes 22 (the case of determining "No" at the step S58). With this configuration, in a case where a plurality of medicine information which should be allocated to the unspecified cassettes 22 exist in the medicine information contained in the subsequent prescription data, the allocation of the medicine information to the unspecified cassette 22 is repeatedly carried out as long as the unspecified cassette 22, which has not yet been subjected to the allocation, exists. Further, in a case where a plurality of medicine information which should be allocated to the unspecified cassettes 22 exist and a plurality of unspecified cassettes which have not yet been subjected to the allocations exist, the allocation control portion 112 may allocate each of the medicine information to each of the unspecified cassettes 22 at the step S55.

Further, in a case where the medicine information which should be allocated to the unspecified cassette 22 is contained in the subsequent prescription data and the unspecified cassette 22 which has not yet been subjected to the allocation does not exist in the unspecified cassettes 22, the medicine dispensing apparatus 400 may has a manual automatically allocating function of automatically allocating the medicine information to the manual packaging unit 4.

Specifically, the allocating control portion 112 may determine whether the manual automatically allocating function should be activated or inactivated in a case where the unspecified cassette 22 which has not yet been subjected to the allocation does not exist (the case of determining "No" at the step S54). A setting for the activation and the inactivation of the manual automatically allocating function is carried out by the control portion 11 depending on a user operation performed on the operating portion 14 at the time of initially setting the medicine dispensing apparatus 400, issuing the subsequent prescription data or the like. Alternatively, the setting for the activation and the inactivation of the manual automatically allocating function may be set in advance for each of the medicine information. The allocating control portion 112 allocates one or more of the medicine information, which do not correspond to the specified cassettes 21 and are not allocated to the unspecified cassettes 22, to the manual packaging unit 4 in a case where the manual automatically allocating function is activated. At this time, the allocating control portion 112 allows the monitor 13 to display a result of allocating the medicine information to the manual packaging unit 4. On the other hand, the allocating control portion 112 returns the process to the step S54 in a case where the setting for allocating the medicine information to the manual packaging unit 4 is inactivated. Further, in a case where the manual packaging unit 4 is used for the current prescription data, the allocating control portion 112 also determines that the setting for allocating the medicine information to the manual packaging unit 4 is inactivated to return the process to the step S54.

With this configuration, the user can supply the tablets corresponding to the medicine information contained in the subsequent prescription data into the manual packaging unit 4, and thereby improving the work efficiency. Further, the allocating control portion 112 may allocate each of the medicine information contained in the subsequent prescription data to the unspecified cassettes 22 according to the decreasing order of the dispensed amount at the step S55 and then allocate remaining medicine information to the manual packaging unit 4 at the step S58. With this configuration, it is possible to reduce a medicine amount to be manually supplied into the manual packaging unit 4 by the user as much as possible.

In the medicine dispensing apparatus 400 according the fourth embodiment, at the step S1 (see FIG. 11) in the medicine dispensing process, in addition to the issuing timing of the prescription data, the dispensing control portion 111 also shifts the process to the step S2 in a case where the subsequent prescription data exists when the dispensation of the medicine corresponding to the current prescription data completes. At the steps S3 to S5, the processes are carried out with respect to the medicine information, which has not been allocated to the unspecified cassette 22 or the manual packaging unit 4 in the subsequent prescription allocating process, among the medicine contained in the subsequent prescription data. Then, at the step S6, the dispensing control portion 111 transmits the start request for the packaging operation to the control portion 61 based on the subsequent prescription data (step S7) in a case where the supplying complete operation for each of the unspecified cassettes 22 corresponding to the medicine information contained in the subsequent prescription data is carried out. At the step S6, the dispensing control portion 111 may determine, on the basis of the detection result of the mounting and removing detection sensor, that the supplying of the medicine into the unspecified cassette 22 completes when the unspecified cassette 22 is removed and mounted.

Hereinafter, other functions of the medicine dispensing apparatus 400 according to the fourth embodiment will be described.

[Continuous Use Function]

In the medicine dispensing process (see FIG. 11), the process is returned to the step S1 after the packaging operation for the prescription data completes. At this time, in the medicine dispensing process (FIG. 11), it is possible to take a configuration in which the unspecified cassette 22, which was used for the dispensation of the medicine specified in the previous prescription data, can be selected as the unspecified cassette 22 to be used for the dispensation of the medicine specified in the subsequent prescription data without removing and mounting of the unspecified cassette 22. Hereinafter, this function for permitting a continuous use in which the removing and mounting of the unspecified cassette 22 after the use thereof is unnecessary is referred to as "continuous use function."

On the other hand, in the medicine dispensing apparatus 400, the control portion 11 can activate and inactivate the continuous use function depending on a user operation performed on the operating portion 14 at the time of the initial setting of the medicine dispensing apparatus 400. Further, in the medicine dispensing apparatus 400, the control portion 11 can activate and inactivate the continuous use function for each unspecified cassette 22 or each prescription data depending on a user operation performed on the operating portion 14 at the time of issuing the prescription data.

In a case where the continuous use function is inactivated, the dispensing control portion 111 does not select the unspecified cassette 22, whose removing and mounting is not detected by the mounting and removing detection sensor, as the unspecified cassette 22 to be used for the dispensation of the medicine specified in the subsequent prescription data after the step S10 in the medicine dispensing process (see FIG. 11). Namely, in this case, after the dispensation of the medicine from the unspecified cassette 22 completes, the user once removes and mounts the unspecified cassette 22 before the allocation of the subsequent medicine information to the unspecified cassette 22. Subsequently, the subsequent medicine information is allocated to the unspecified cassette 22 and then the user removes and mounts the unspecified cassette 22 to supply the medicine into the unspecified cassette 22. With this configuration, it is necessary to remove and mount the unspecified cassette 22 after the use of the unspecified cassette 22, thereby prompting the user to check whether or not a remaining medicine exists in the unspecified cassette 22, a circumstance of the unspecified cassette 22 (for example, whether or not powder exists in the unspecified cassette 22) or the like.

The continuous use function of the medicine dispensing apparatus 400 contains a same type continuous use function and a different type continuous use function. The same type continuous use function is a function of permitting the continuous use of the unspecified cassette in a case where the medicine information allocated to the unspecified cassette 22 just before is identical to the medicine information to be subsequently allocated to the unspecified cassette 22. Even if the same type continuous use function is activated, in a case where the medicine information allocated to the unspecified cassette 22 just before is different from the medicine information to be subsequently allocated to the unspecified cassette 22, the process is carried out in the same manner as the case where the continuous use function is inactivated. On the other hand, the different type continuous use function is a function of permitting the continuous use of the unspecified cassette 22 in a case where the medicine information allocated to the unspecified cassette 22 just before is different from the medicine information to be subsequently allocated to the unspecified cassette 22.

Further, in the medicine dispensing apparatus 400, the control portion 11 can independently change the settings for activating or inactivating the same type continuous use function and the different type continuous use function depending on a user operation performed on the operating portion 14 at the time of the initial setting of the medicine dispensing apparatus 400. Alternatively, it is possible to take another configuration in which a combination setting of the setting for inactivating the same type continuous use function and the setting for activating the different type continuous use function cannot be selected. Hereinafter, in the medicine dispensing apparatus 400, the case where the continuous use function is activated means a case where at least one of the same type continuous use function and the different type continuous use function is activated.

In a case where the same type continuous use function is activated and the medicine information allocated to the unspecified cassette 22 just before is identical to the medicine information to be subsequently allocated to the unspecified cassette 22, the control portion 11 may not automatically carry out the remaining medicine collecting process. Namely, the dispensing control portion 111 does not transmit the request for the remaining medicine collecting process to the control portion 61 in the medicine dispensing process (see FIG. 11). Thus, since the remaining medicine collecting process is not carried out by the control portion 61 after the dispensation of the tablet from the unspecified cassette 22, it is possible to continuously use the tablets remaining in the unspecified cassette 22 at the time of the subsequent dispensation of the tablet specified in the subsequent prescription data. In this case, the dispensing control portion 111 omits the steps S4 to S6 in the medicine dispensing process (see FIG. 11). With this configuration, in a case where the same type of medicine information specified in the subsequent prescription data which is continuously issued is allocated to the same unspecified cassette 22, it is possible to start the packaging operation in the medicine dispensing process (see FIG. 11) without carrying out the supplying complete operation of the medicine for the unspecified cassette 22.

[Status Display Function]

Next, description will be given to the status display function of the medicine dispensing apparatus 400. As described above, by using the status display function, the user can easily recognize the working status of each of the unspecified cassettes 22 by visually inspecting and confirming the display portion 23 of each of the unspecified cassettes 22.

As shown in FIG. 16, in the medicine dispensing apparatus 400, each of the unspecified cassettes 22 has a status display lamp 27 in addition to the display portion 25. The display portion 25 is the electronic paper which can keep displaying the display contents even in the non-energizing state once the display contents are written in the energizing state. The status display lamp 27 is provided on, for example, a front surface of the unspecified cassette 22 together with the display portion 25. The medicine dispensing apparatus 400 may take another configuration in which each of the unspecified cassettes 22 does not have the status display lamp 27.

The status display lamp 27 is a light source such as an LED used for displaying the working status of the unspecified cassette 22 with an emission color or an emission mode.

The emission mode contains a light-off mode, a light-on mode, a light blinking mode or the like. The status display lamp 27 is connected to the connector on the side of the unspecified cassette 22 in the same manner as the display portion 25. The status display lamp 27 and the prescription control unit 1 are electrically connected with each other through the connector when the unspecified cassette 22 is mounted on the mounting portion 221. With this configuration, the prescription control unit 1 can change a display state of the status display lamp 27. Further, the status display lamp 27 may be provided at the mounting portion 221 on which the unspecified cassette 22 should be mounted.

In the medicine dispensing apparatus 400, the control portion 11 contains a display control portion 113 for controlling the display contents of the display portion 25 and the status display lamp 27. The control portion 11 carries out various processes with the CPU according to various programs preliminary stored in the storage means such as the ROM, the EEPROM and the storage portion 12 which serve as the display control portion 113. In this case, the display control portion 113 is one example of display control means. Further, the control portion 61 of the packaging control unit 6 may contain the display control portion 113.

The display control portion 113 carries out a display control process described below (see FIGS. 22 and 23) to allow the display portion 25 and the status display lamp 27 to display dispensing information related to the medicine information allocated to the unspecified cassette 22 and the status information related to the working status of the unspecified cassette 22. For example, the dispensing information includes at least one of a medicine name, a medicine code, a dispensed amount, a lot number, an expiration date, a remaining amount, a shortage amount of the medicine corresponding to the medicine information and a patient name of prescription object. Specifically, the display control portion 113 preferably allows the display portion 25 to display at least the medicine name, the dispensed amount of the medicine corresponding to the medicine information, the patient name of prescription object and the status information. With this configuration, the user can visually inspect and confirm the various information regardless of whether the unspecified cassette 22 is in the mounting state or the non-mounting state, thereby improving the work efficiency.

The display control portion 113 can obtain information on the dispensed amount and the patient name from the prescription data containing the medicine information. Further, the display control portion 113 can obtain information on the lot number, the expiration data or the like when a barcode labeled on a medicine container such as a medicine bottle in which the medicine in the unspecified cassette 22 was contained is read by the barcode reader 7. In the medicine dispensing apparatus 400 having the status display function, since the display portion 25 and the status display lamp 27 are controlled by the display control portion 113, the steps S5 and S9 are omitted from the medicine dispensing process (see FIG. 11).

Figure 22:
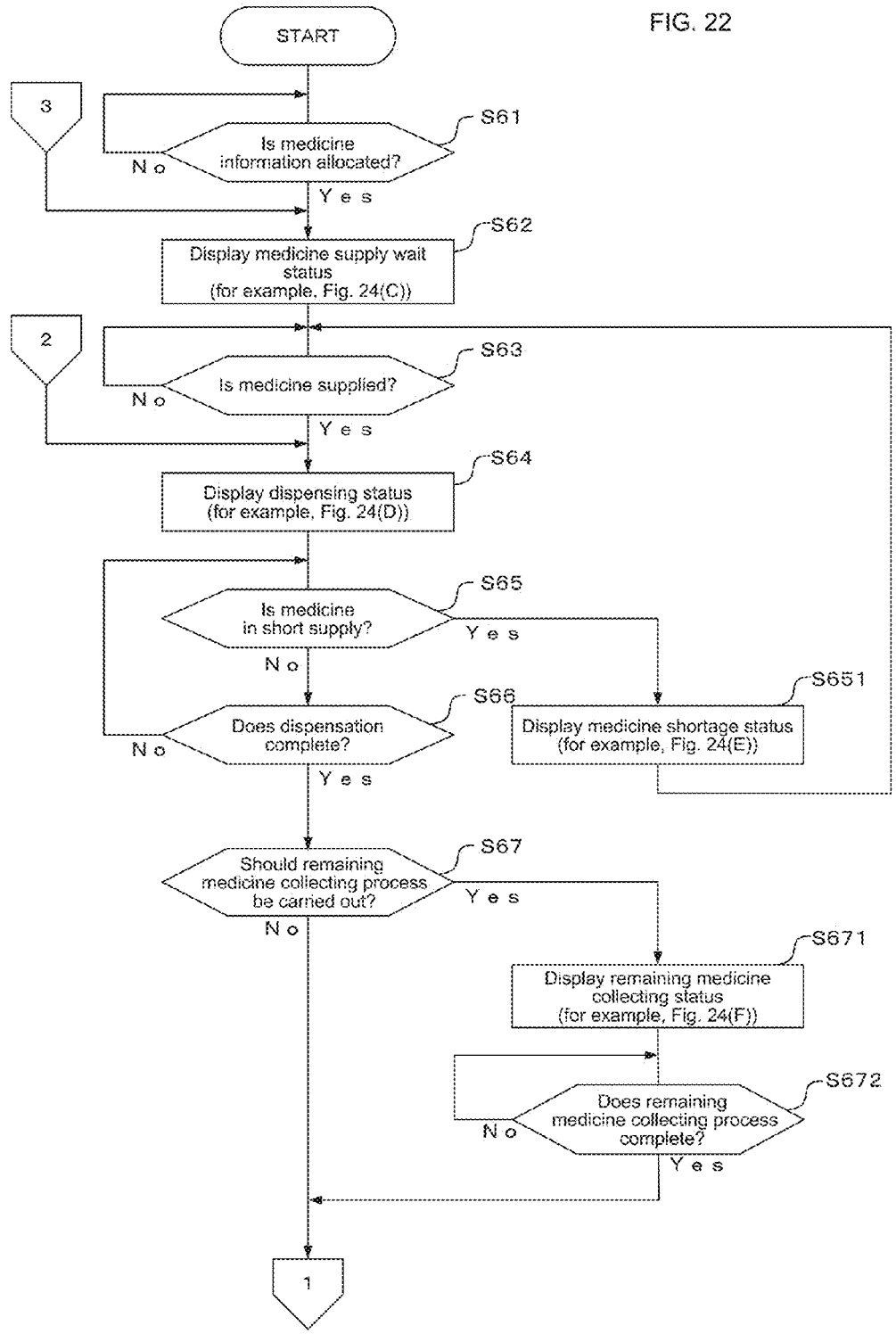
FIG. 22 is a flow chart for explaining one example of a procedure for a display control process.

Hereinafter, one example of the display control process carried out by the display control portion 113 will be described with reference to FIGS. 22 to 24. The display control process is carried out in substantially parallel with the medicine dispensing process (see FIG. 11) and the subsequent prescription allocating process (see FIG. 17). The display control portion 113 independently carries out the display control process for each of the unspecified cassettes 22. FIG. 24 is a view showing display examples of the display portion 25 and the status display lamp 27 of the unspecified cassette 22 in the display control process. Pattern differences between the status display lamps 27 shown in FIG. 24 means differences of the emission colors or the emission modes.

<Step S61>

First, at a step S61, the display control portion 113 waits for the allocation of the medicine information to the unspecified cassette 22 in the medicine dispensing process (see FIG. 11) and the subsequent prescription allocating process (see FIG. 17) (the case of determining "No" at the step S61). In the case where the display control portion 113 waits for the allocation of the medicine information, the display control portion 113 allows the display portion 25 of the unspecified cassette 22 to display an initial screen (described below, see FIG. 24(A) or 24(B)) indicating the non-allocated state that the medicine information is not allocated to the unspecified cassette 22. The display control portion 113 shifts the process to a step S62 in a case where the display control portion 113 determines that the medicine information is allocated to the unspecified cassette 22 (the case of determining "Yes" at the step S61).

<Step S62>

At the step S62, the display control portion 113 allows the display portion 25 and the status display lamp 27 of the unspecified cassette 22 to display the dispensing information and the status information indicating that the unspecified cassette 22 is in a medicine supply wait status (this is one example of the working statuses).

In FIG. 24(C), one display example of the medicine supply wait status is shown. As shown in FIG. 24(C), the display portion 25 contains display areas 252 to 255 for displaying the dispensing information and a display area 256 for displaying the status information. The display area 252 is an area for displaying the medicine name corresponding to the medicine information. In this example, the medicine name "Alinamin" is displayed on the display area 252. The display area 253 is an area for displaying the patient name indicated in the prescription data containing the medicine information. In this example, the patient name "Taro YUYAMA" is displayed on the display area 253. The display area 254 is an area for displaying the JAN code of the medicine corresponding to the medicine information. The JAN code is one example of the one-dimensional code indicating the identification information on the medicine. Instead of the JAN code, it is possible to use other types of the one-dimensional code such as an RSS code (GS1 data bar) or a two-dimensional code such as a QR code (registered trademark). The display area 255 is an area for displaying the dispensed amount (prescription amount) of the medicine corresponding to the medicine information indicated in the prescription data containing the medicine information. In this example, the dispensed amount "50 tablets" is displayed on the display area 255. The display control portion 133 retrieves various information to be displayed on the display areas 252 to 256 from the storage portion 12 or the RFID tag 26 to allow the display portion 25 to display the various information.

Further, the status information is displayed on the display area 256 using a numerical number, a character (Chinese character or alphabet), a mark, a diagram or a color pattern predetermined so as to correspond to each of the working statuses of the unspecified cassette 22. In the example shown in FIG. 24(C), characters "D1" indicating the medicine supply wait status are displayed on the display area 256. Further, the status information may be displayed using a character, by which the user can image the status of the unspecified cassette 22 at one view, such as a Chinese character string meaning "Supply" or one Chinese character suggesting the medicine supply wait status instead of using the characters "D1." Further, it is possible to display one working status (for example, the medicine supply wait status) by allowing the display area 256 to be a non-display state.

Further, the status display lamp 27 displays the medicine supply wait status using the emission color or the emission mode of the status display lamp 27. For example, the display state of the status display lamp 27 corresponding to the medicine supply wait status is a state that a green color is blinking. Here, description will be given to a case where partially similar statuses are allocated to the same emission color and the same emission mode of the status display lamp 27. On the other hand, the working statuses of the unspecified cassette 22 may be respectively allocated to the different emission colors and the different emission modes of the status display lamp 27.

<Step S63>

At a step S63, the display control portion 113 determines whether or not the medicine is supplied into the unspecified cassette 22. For example, the display control portion 113 determines that the medicine is supplied into the unspecified cassette 22 when the supplying complete operation is carried out to the operating portion 14 or when the removing and mounting detection sensor, which can detect the removing and mounting of the unspecified cassette 22, detects the removing and mounting of the unspecified cassette 22. At this time, the display control portion 113 shifts the process to a step S64 in a case where the display control portion 113 determines that the medicine is supplied (the case of determining "Yes" at the step S63). On the other hand, the display control portion 113 holds the process at the step S63 on standby until the medicine is supplied (the case of determining "No" at the step 63).

<Step S64>

At the step S64, the display control portion 113 allows the display portion 25 and the status display lamp 27 of the unspecified cassette 22 to display the status information indicating that the unspecified cassette 22 is in a dispensing status (one example of the working statuses).

In FIG. 24(D), one display example of the dispensing status is shown. In the example of FIG. 24(D), characters "D2" indicating the dispensing status are displayed on the display area 256. Further, the status information may be a Chinese character string meaning "Dispensing" or one Chinese character suggesting that the medicine is being dispensed instead of the characters "D2." Furthermore, the dispensing status is displayed by the status display lamp 27 using the emission color and the emission mode of the status display lamp 27. For example, the display state of the status display lamp 27 displaying the dispensing status may be a status that a green color is turned on (light-on). As shown in FIG. 24(D), even in the dispensing status, as the dispensing information, "Alinamin" is displayed on the display area 252, "Taro YUYAMA" is displayed on the display area 253, the JAN code is displayed on the display area 254 and "50 tablets" is displayed on the display area 255.

<Step S65>

At a step S65, the display control portion 113 determines whether or not the medicine in the unspecified cassette 22 is insufficient (in short supply) with respect to the dispensed amount of the medicine corresponding to the medicine information indicated in the prescription data containing the medicine information allocated to the unspecified cassette 22. For example, the display control portion 113 determines that the medicine is in short supply in a case where the medicine is not dispensed from the unspecified cassette 22 anymore when the unspecified cassette 22 is driven for a predetermined time period in a state where an amount of the medicine dispensed from the unspecified cassette 22 does not reach the dispensed amount. At this time, the display control portion 113 shifts the process to a step S651 in a case where the display control portion 113 determines that the medicine is in short supply (the case of determining "Yes" at the step 65). On the other hand, the display control portion 113 shifts the process to a step S66 in a case where the medicine is not in short supply (the case of determining "No" at the step S65).

<Step S651>

At the step S651, the display control portion 113 allows the display portion 25 and the status display lamp 27 of the unspecified cassette 22 to display the status information indicating a medicine shortage status (one example of the working statuses) indicating that the medicine in the unspecified cassette 22 is in short supply and a shortage amount of the medicine. Then, the display control portion 113 shifts the process to the step S63 to wait for the supplying of the medicine into the unspecified cassette 22 (the case of determining "No" at the step S63).

In FIG. 24(E), one display example of the medicine shortage status is shown. In the example shown in FIG. 24(E), characters "D3" indicating the medicine shortage status are displayed on the display area 256. Further, the status information may be a Chinese character string meaning "Out of stock" or one Chinese character suggesting that the medicine is out of stock (in short supply) instead of the characters "D3." Furthermore, the medicine shortage status is displayed by the status display lamp 27 using the emission color or the emission mode of the status display lamp 27. For example, the display state of the status display lamp 27 indicating the medicine shortage status is a state that a green color is blinking which is the same as the medicine supply wait status. As shown in FIG. 24(E), even in the medicine shortage status, as the dispensing information, "Alinamin" is displayed on the display area 252, "Taro YUYAMA" is displayed on the display area 253 and the JAN code is displayed on the display area 254.

On the other hand, the display control portion 113 allows the display area 255 to display a required amount of the medicine to be supplied into the unspecified cassette 22, that is, the shortage amount of the medicine instead of the dispensed amount. In the example shown in FIG. 24(E), the shortage amount "15 tablets" is displayed. Specifically, a difference between the amount to be dispensed (prescription amount) indicated in the prescription data containing the medicine information allocated to the unspecified cassette 22 and an amount of the medicine already dispensed from the unspecified cassette 22 is calculated to obtain the shortage amount.

In a case where the dispensing status at the step S64 is displayed, the display control portion 113 may reduce the dispensed amount displayed on the display area 255 every time the counter detects the dispensation of the medicine. With this configuration, the shortage amount with respect to the amount to be dispensed is displayed on the display area 255 when the unspecified cassette 22 becomes the medicine shortage status. The display control portion 113 may allow the display portion 25 and the status display lamp 27 of the unspecified cassette 22 to display that the medicine is in short supply and not to display the shortage amount of the medicine. Further, the display control portion 113 may allow the display portion 25 and the status display lamp 27 of the unspecified cassette 22 not to display that the medicine is in short supply and to display the shortage amount of the medicine. In the case where the display control portion 113 allows the display portion 25 and the status display lamp 27 of the unspecified cassette 22 not to display that the medicine is in short supply and to display the shortage amount of the medicine, the display control portion 113 may allow the display portion 25 to display that the medicine is in short supply by blinking the display of the shortage amount or the like.

<Step S66>

At the step S66, the display control portion 113 determines whether or not the dispensation of the medicine from the unspecified cassette 22 completes. For example, the display control portion 113 determines whether or not the dispensation completes depending on whether or not a control signal, which indicates that the medicine has been dispensed from the unspecified cassette 22 in the dispensed amount indicated in the prescription data, is received from the control portion 61. At this time, the display control portion 113 shifts the process to a step S67 in a case where the display control portion 113 determines that the dispensation completes (the case of determining "Yes" at the step S66). On the other hand, the display control portion 113 returns the process to the step S65 in a case where the dispensation does not complete.

<Step S67>

At the step S67, the display control portion 113 branches the process depending on whether or not the remaining medicine collecting process for automatically collecting the medicine remaining in the unspecified cassette 22 should be carried out. A setting for determining whether or not the remaining medicine collecting process should be carried out is set by the control portion 11 depending on a user operation performed on the operating portion 14 at the time of the initial setting of the medicine dispensing apparatus 400. At this time, if the display control portion 113 determines that the same type continuous use function is activated and the medicine information, which was allocated to the unspecific cassette 22 by the previous prescription data before, is identical to the medicine information allocated by the subsequent prescription data, the display control portion 113 may determine that the remaining medicine collecting process should not be carried out. The display control portion 113 shifts the process to a step S671 in a case where the display control portion 113 determines that the setting is set so that the remaining medicine collecting process should be carried out (the case of determining "Yes" at the step S67). On the other hand, the display control portion 113 shifts the process to a step S68 in a case where the display control portion 113 determines that the setting is set so that the remaining medicine collecting process should not be carried out (the case of determining "No" at the step S67).

<Step S671>

At the steps S671, the display control portion 113 allows the display portion 25 and the status display lamp 27 of the unspecified cassette 22 to display the status information indicating a remaining medicine collecting status (one example of the working statuses) indicating that the medicine remaining in the unspecified cassette 22 is being collected.

In FIG. 24(F), one display example of the remaining medicine collecting status is shown. In the example shown in FIG. 24(F), characters "D4" indicating the remaining medicine collecting status are displayed on the display area 256. The status information may be a Chinese character string meaning "Collection" or one Chinese character suggesting that the remaining medicine is being collected instead of the characters "D4." Further, the status information corresponding to the remaining medicine collecting status may be identical to the status information corresponding to the dispensing status. Furthermore, the remaining medicine collecting status is displayed by the status display lamp 27 using the emission color and the emission mode of the status display lamp 27. For example, the display state of the status display lamp 27 indicating the remaining medicine collecting status is a state that a green color is turned on which is the same as the dispensing status. As shown in FIG. 24(F), even in the remaining medicine collecting status, as the dispensing information, "Alinamin" is displayed on the display area 252, "Taro YUYAMA" is displayed on the display area 253, the JAN code is displayed on the display area 254 and "50 tablets" is displayed on the display area 255.

<Step S672>

As a step S672, the display control portion 113 waits for the completion of the collecting process (the case of determining "No" at the step S672). On the other hand, the display control portion 113 shifts the process to the step S68 in a case where the display control portion 113 determines that the remaining medicine collecting process completes (the case of determining "Yes" at the step S68).

For example, the display control portion 113 determines the completion of the remaining medicine collecting process on the basis of a control signal transmitted from the control portion 61 at the time of the completion of the remaining medicine collecting process. The control portion 61 drives the first rotating body 223 and the second rotating body 224 of the unspecified cassette 22 for a predetermined collecting time period in the remaining medicine collecting process. With this configuration, in a case where the tablets remain in the unspecified cassette 22, the tablets are dispensed from the unspecified cassette 22. At this time, the control portion 61 may terminate the remaining medicine collecting process when the tablets are dispensed from the unspecified cassette 22 in a predetermined amount. With this configuration, in a case where a lot of tablets remain in the unspecified cassette 22, it is possible to terminate the remaining medicine collecting process in mid-flow. Then, the control portion 61 transmits information indicating whether or not the remaining medicine collecting process should be terminated in mid-flow to the control portion 11 together with the control signal at the time of the completion of the remaining medicine collecting process. With this configuration, the display control portion 113 of the control portion 11 can determine whether or not the remaining medicine collecting process should be terminated in mid-flow, that is, it is possible to determine that there is possibility that the tablets remain in the unspecified cassette 22.

<Allocating Timing for the Medicine Information>

In the medicine dispensing apparatus 400, allocating timing for the subsequent medicine information to one of the unspecified cassettes 22 after the dispensation of the medicine or the completion of the remaining medicine collecting process is changed depending on whether a change unit of the allocation state of the unspecified cassette 22 is a medicine unit or a prescription unit. A setting related to the change unit of the allocation state is carried out by the control portion 11 depending on a user operation performed on the operating portion 14 at the time of the initial setting of the medicine dispensing apparatus 400 or the like.

First, in a case where the change unit of the allocation state of the unspecified cassette 22 is the medicine unit, the dispensing control portion 111 changes the allocation state of the unspecified cassette 22 to the non-allocated state when the dispensation of the medicine from one unspecified cassette 22 among the plurality of unspecified cassettes 22 used in the prescription data completes. In this case, in the medicine dispensing apparatus 400, the control portion 61 independently reports the control portion 11 whether or not the dispensation of the medicine from each of the unspecified cassettes 22 completes. Thus, even in a case where the plurality of unspecified cassettes 22 are used for one prescription data, the allocating control portion 112 can allocate the medicine information of the subsequent prescription data to one of the plurality of unspecified cassettes 22 in order from the unspecified cassette 22 from which the dispensation of the medicine completes. In a case where the continuous use function is inactivated, the dispensing control portion 11 may change the allocation state of the unspecified cassette 22 to the non-allocated state on condition that the removing and mounting operation of the unspecified cassette 22 is carried out.

On the other hand, the change unit of the allocation state is the prescription unit, the dispensing control portion 111 changes the allocation state of each of the unspecified cassettes 22 to the non-allocated state when all of the dispensations of the medicines from all of the unspecified cassettes 22 used for the prescription data complete. In this case, the allocating control portion 112 allocates the medicine information of the subsequent prescription data to each of the unspecified cassettes 22 when all of the dispensations of the medicines from all of the unspecified cassettes 22 used for one previous prescription data complete. In a case where the continuous use function is inactivated, the dispensing control portion 111 may independently change the allocation states of the unspecified cassettes 22 to the non-allocated states on condition that the removing and mounting operation of each of the unspecified cassettes 22 is carried out after all of the dispensations of the medicines from all of the unspecified cassettes 22 used for the prescription data complete.

<Step S68>

Figure 23:
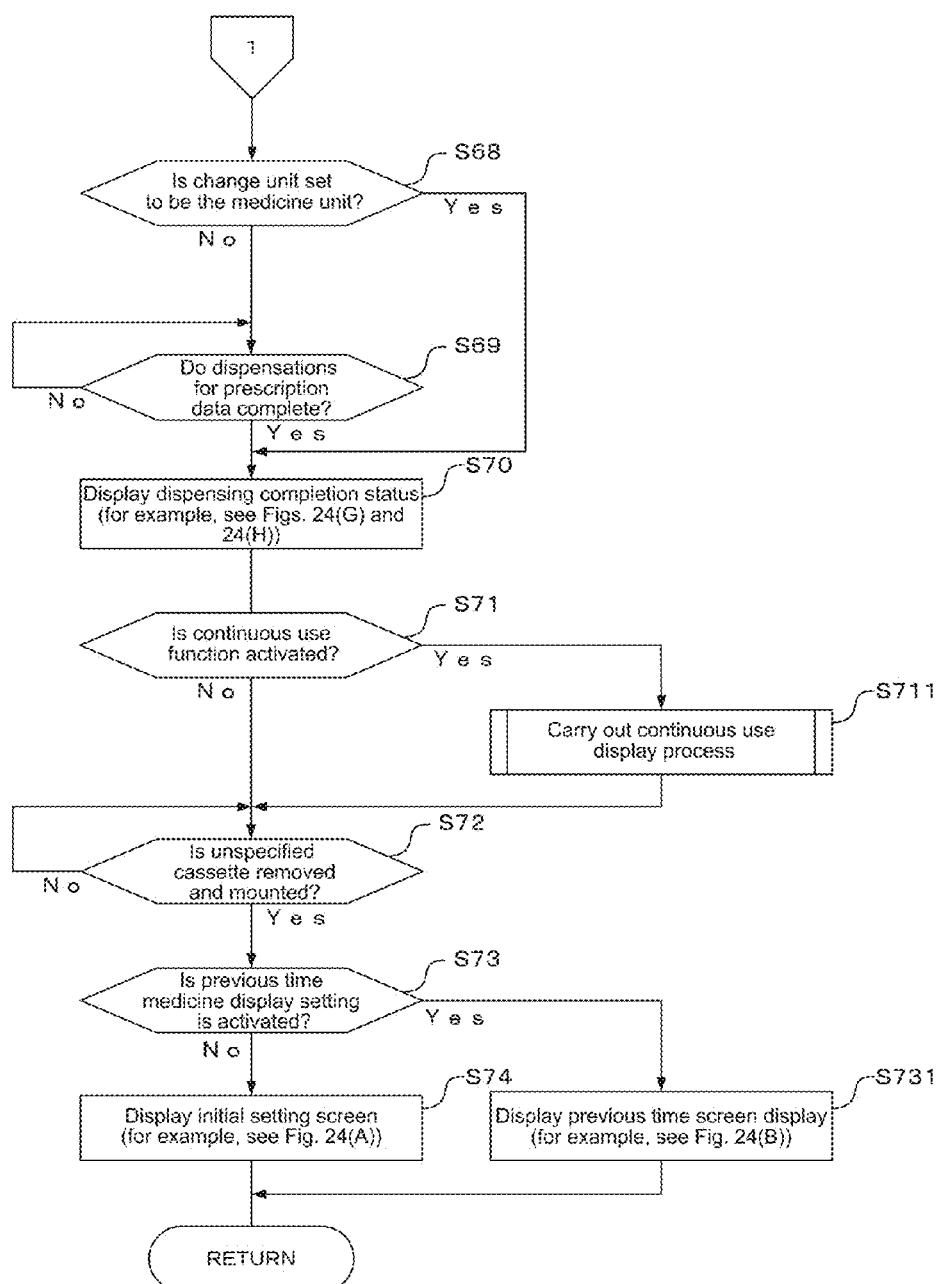
FIG. 23 is another flow chart for explaining the one example of the procedure for the display control process.
Figure 24:
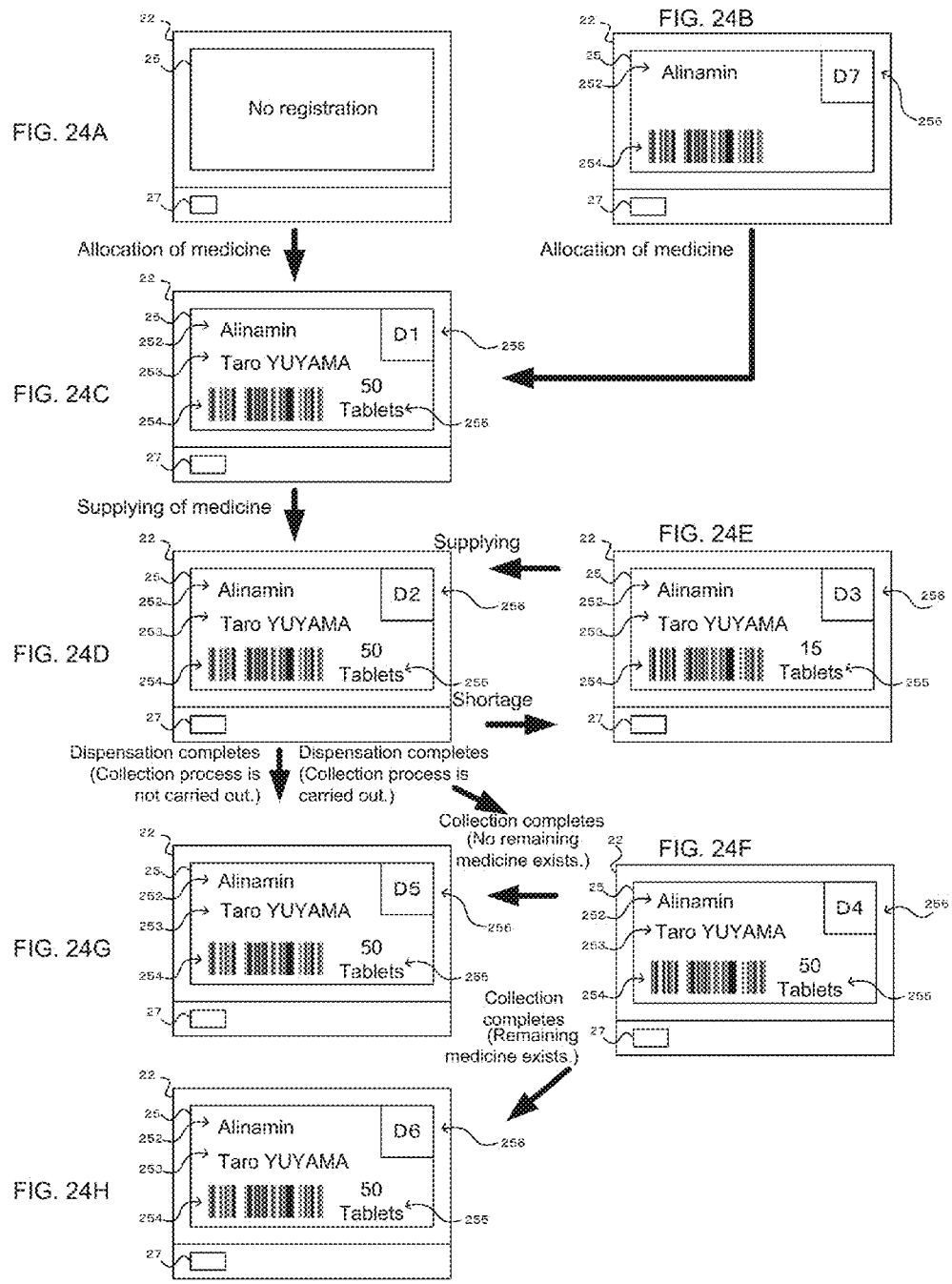
FIG. 24 is a view showing a display example at the time of carrying out the display control process.

As shown in FIG. 23, in the display control process at the steps S68 to S70, the display state of the display portion 25 is changed depending on the allocating timing of the subsequent medicine information to the unspecified cassette 22. Specifically, the display control portion 113 branches the process depending on whether the change unit of the allocation state of the medicine information to each of the unspecified cassettes 22 is the medicine unit or the prescription unit. At this time, the display control portion 113 shifts the process to a step S69 in the case where the change unit of the allocation state of the unspecified cassette 22 is the prescription unit (the case of determining "No" at the step S68). On the other hand, the display control portion 113 shifts the process to a step S70 in the case where the change unit of the allocation state of the unspecified cassette 22 is the medicine unit (the case of determining "Yes" at the step 68).

<Step S69>

At the step S69, the display control portion 113 waits for the completion of all of the dispensations of the medicines corresponding to all of the medicine information in the prescription data (the case of determining "No" at the step S69). For example, the display control portion 113 determines that all of the dispensations of the medicines for the prescription data complete when the display control portion 113 receives the packaging completion reports from the control portion 61. At this time, the display control portion 113 shifts the process to a step S70 in a case where the display control portion 113 determines that all of the dispensations of the medicines for the prescription data complete (the case of determining "Yes" at the step S69).

<Step S70>

At the step S70, the display control portion 113 allows the display portion 25 and the status display lamp 27 of the unspecified cassette 27 to display the status information indicating that the unspecified cassette 22 is in a dispensing completion status (one example of the working statuses). Namely, in the display control process, in the case where the allocation state of the unspecified cassette 22 is changed in the medicine unit, the dispensing completion status is displayed on the display portion 25 of the unspecified cassette 22 when the dispensation of the medicine completes. On the other hand, in the case where the allocation state of the unspecified cassette 22 is changed in the prescription unit, the dispensation completion status is displayed on the display portion 25 of each of the unspecified cassettes 22 when all of the dispensations of the medicines from all of the unspecified cassettes 22 used for one prescription data complete.

Figure 25:
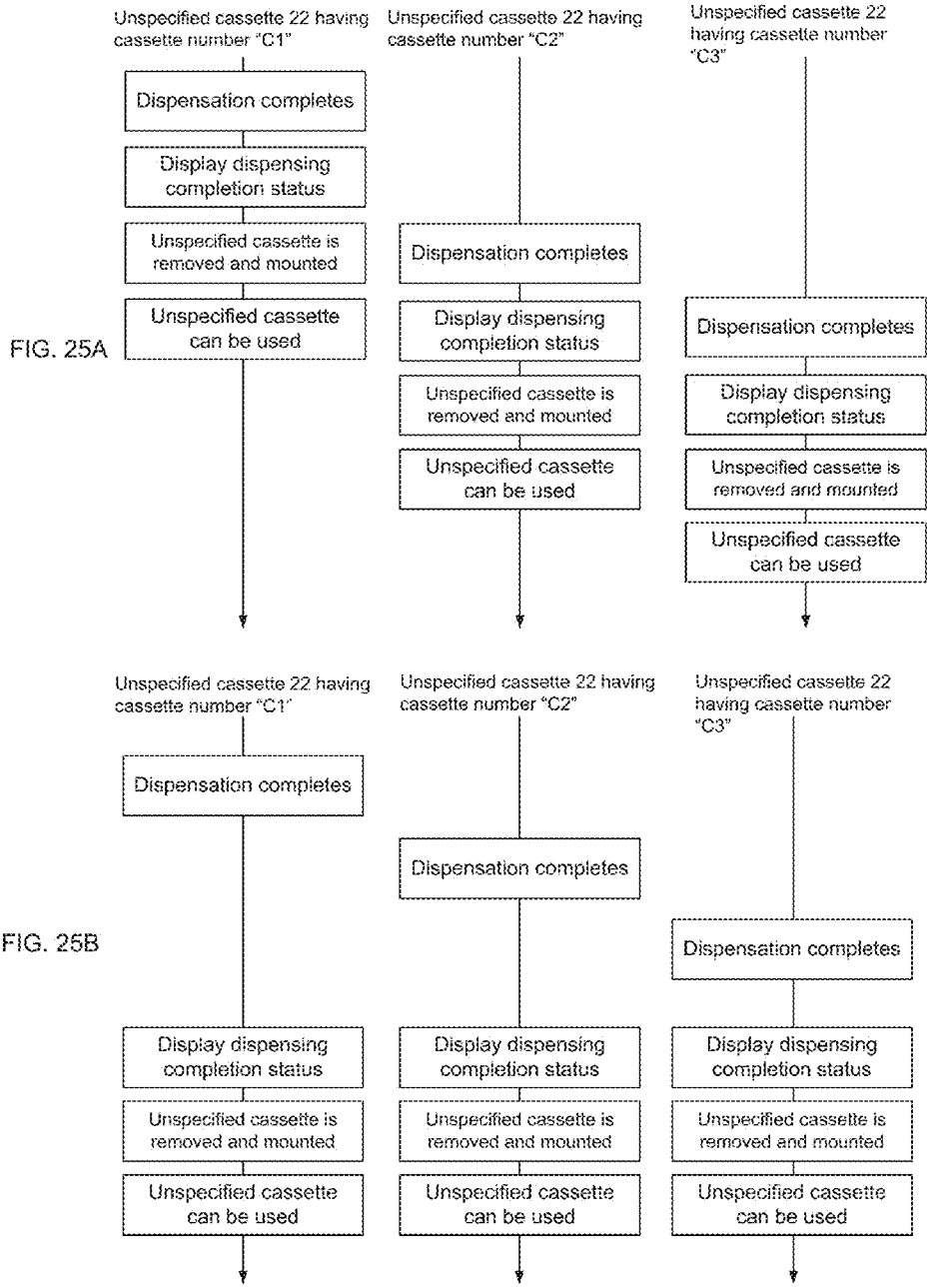
FIG. 25 is a view showing one example of changing timing of an allocation state of the unspecified cassette.

FIG. 25(A) is a conceptual view showing changing timing of the allocation state in the case where the change unit of the allocation state of the unspecified cassette 22 is the medicine unit. FIG. 25(B) is a conceptual view showing changing timing of the allocation state in the case where the change unit of the allocation state of the unspecified cassette 22 is the prescription unit. In FIGS. 25(A) and 25(B), examples of the changing timings of the allocation states in a case where the unspecified cassettes 22 having the cassette numbers "C1," "C2" and "C3" are used in the prescription data are shown.

As shown in FIG. 25(A), in the case where the change unit of the allocation state of the unspecified cassette 22 is the medicine unit, the dispensation completion status is displayed on the display portion 25 of the unspecified cassette 22 having the cassette number "C1" when the dispensation of the medicine from the unspecified cassette 22 having the cassette number "C1" completes. Then, when the unspecified cassette 22 having the cassette number "C1" is removed and mounted, the allocation state of the unspecified cassette 22 having the cassette number "C1" is changed to the non-allocated state to make the unspecified cassette 22 available. Regarding each of the unspecified cassettes 22 having the cassette numbers "C2" and "C3," the displaying of the dispensation completion status and the changing of the allocation state of the unspecified cassette 22 are carried out in the same manner as the unspecified cassette 22 having the cassette number "C1" independently from the other unspecified cassettes 22.

On the other hand, as shown in FIG. 25(B), in the case where the change unit of the allocation state of the unspecified cassette 22 is the prescription unit, the dispensation completion status is not displayed on the display portion 25 of the unspecified cassette 22 having the cassette number "C1" even after the dispensation of the medicine from the unspecified cassette 22 having the cassette number "C1" completes. Then, when the dispensations of the medicines from the unspecified cassettes 22 having the cassette numbers "C2" and "C3" complete, the dispensation completion status is displayed on the display portion 25 of each of the unspecified cassettes 22 having the cassette numbers "C1" to "C3." Then, when each of the unspecified cassettes 22 having the cassette numbers "C1" to "C3" is removed and mounted, the allocation state of each of the unspecified cassettes 22 is changed to the non-allocation state to make each of the unspecified cassettes 22 available.

At the step S70, the display control portion 113 switches the display contents of the display portion 25 corresponding to the dispensation completion status depending on whether or not the remaining medicine collecting process for the unspecified cassette 22 is terminated in mid-flow. In FIGS. 24(G) and 24(H), display examples of the dispensation completion status are shown.

Specifically, the display control portion 113 allows the display area 256 to display characters "D5" indicating dispensation completion status corresponding to a case where the remaining medicine collecting process is normally terminated as shown in FIG. 24(G) when the display control portion 113 receives a report indicating that the remaining medicine collecting process is normally terminated from the control portion 61. For example, the characters "D5" may be replaced with a Chinese character string meaning "Finished Dispensation" or one Chinese character suggesting the dispensation completion status.

On the other hand, the display control portion 113 allows the display area 256 to display characters "D6" indicating the dispensation completion status corresponding to the case where the remaining medicine collecting process is terminated in mid-flow as shown in FIG. 24(H) when the display control portion 113 receives a report indicating the remaining medicine collecting process is terminated in mid-flow from the control portion 61. For example, the characters "D6" may be replaced with a Chinese character string meaning "Remaining" or one Chinese character suggesting that there is possibility that the medicine remains in the unspecified cassette 22.

As shown in FIGS. 24(G) and 24(H), the status display lamp 27 displays the dispensation completion status using the emission color or the emission mode of the status display lamp 27. For example, the display state of the status display lamp 27 indicating the dispensation completion status may be a state that a green color is turned on. Further, as shown in FIGS. 24(G) and 24(H), even in the dispensation completion status, as the dispensing information, "Alinamin" is displayed on the display area 252, "Taro YUYAMA" is displayed on the display area 253, the JAN code is displayed on the display area 254 and "50 tablets" is displayed on the display area 255.

<Step S71>

At a step S71, the display control portion 113 branches the process depending on whether or not the continuous use function is activated. The display control portion 113 determines that the continuous use function is activated in a case where at least one of the same type continuous use function and the different type continuous use function is activated. The display control portion 113 shifts the process to a step S711 to carry out a continuous use display process described below (see FIG. 26) in a case where the continuous use function is activated (the case of determining "Yes" at the step 71). On the other hand, the display control portion 113 shifts the process to a step S72 in a case where the continuous use function is inactivated (the case of determining "No" at the step S71).

<Step S72>

At the step S72, the display control portion 113 waits for the removing and mounting of the unspecified cassette 22 (the case of determining "No" at the step S72). The step S72 is a process for concluding that the user confirms that the medicine does not remain in the unspecified cassette 22. The dispensing control portion 111 determines, on the basis of the detection result of the removing and mounting detection sensor provided at the mounting portion 221 for detecting the removing and mounting of the unspecified cassette 22, whether or not the removing and mounting operation of the unspecified cassette 22 is carried out. The display control portion 113 shifts the process to a step S73 in a case where the display control process 113 determines that the removing and mounting operation of the unspecified cassette 22 has been carried out (the case of determining "Yes" at the step 72).

<Step S73>

At the step S73, the display control portion 113 branches the process depending on whether or not there is a previous time medicine display setting for allowing the display portion 25 to display the medicine information, which was allocated to the unspecified cassette 22 for the previous prescription data, as the previous medicine information. The setting related to activation and inactivation of the previous time medicine display setting is set by the control portion 11 depending on a user operation performed on the operating portion 14 at the time of the initial setting of the medicine dispensing apparatus 400. At this time, the display control portion 113 shifts the process to a step S74 in a case where the display control portion 113 determines that the previous time medicine display setting is inactivated (the case of determining "No" at the step S73). On the other hand, the display control portion 113 shifts the process to a step S731 in a case where the display control portion 113 determines that the previous medicine display is activated (the case of determining "Yes" at the step 73).

<Step S74>

At the step S74, the display control portion 113 allows the display portion 25 and the status display lamp 27 of the unspecified cassette 22 to display the status information indicating that the unspecified cassette is in the non-allocated state (one example of the working statuses).

FIG. 24(A) is a view showing an initial screen corresponding to a case where the previous time medicine display setting is inactivated and the unspecified cassette is in the non-allocated state. In the initial screen shown in FIG. 24(A), there is no display content on the display areas 252 to 256 and only a character string "No registration" is displayed. The display control portion 113 may allow the display portion 25 to be the non-display state (turned-off state). The status display lamp 27 displays the non-allocated state using the emission color or the emission mode of the status display lamp 27. For example, the display state of the status display lamp 27 corresponding to the non-allocated state is a state that the status display lamp 27 is turned off.

<Step S731>

On the other hand, at the step S731, the display control portion 113 allows the display portion 25 and the status display lamp 27 of the unspecified cassette to display the status information indicating that the unspecified cassette 22 is in the non-allocated state (one example of the working statuses).

FIG. 24(B) is one display example corresponding to the case where the previous time medicine display setting is activated, which indicates the non-allocated state. In the example shown in the FIG. 24(B), the medicine name "Alinamin" corresponding to the medicine information allocated to the unspecified cassette 22 just before is displayed on the display area 252 and the JAN code corresponding to the medicine information is displayed on the display area 254. Further, in the example shown in FIG. 24(B), characters "D7" which indicate the non-allocated state in the case where the previous time medicine display setting is activated are displayed on the display area 256. For example, the characters "D7" may be replaced with a Chinese character string meaning "Previous time" or one character suggesting that the display portion 25 displays the previous medicine. The status display lamp displays the non-allocated state using the emission color or the emission mode of the status display lamp 27. For example, the display state of the status display lamp 27 corresponding to the non-allocated state is a state that the status display lamp 27 is turned off.

As described above, in the case where the medicine dispensing apparatus 400 has the function of using the unspecified cassette 22 as a cassette to which specified medicine information is allocated, it is possible to take a configuration in which the control portion 11 allows the display portion 25 to display the medicine name and the JAN code of the medicine specified by the medicine information. In contrast, at the step S731, characters "D7" indicating that information on the medicine used in the previous time are displayed on the display area 256 of the display portion 25 of the unspecified cassette 22. With this configuration, it is possible to clarify that the medicine information displayed on the display portion 25 of the unspecified cassette 22 is the medicine information on either the medicine specifically allocated to the unspecified cassette 22 by means of the function of using the unspecified cassette 22 for the specified medicine or the medicine used in the previous time. In the case where the medicine information is specifically allocated to the unspecified cassette 22 by means of the function of using the unspecified cassette 22 for the specified medicine, the display control portion 113 may allow the display area 256 to display the status information indicating the medicine information is specifically allocated to the unspecified cassette 22 by means of the function of using the unspecified cassette 22 for the specified medicine.

As described above, in the medicine dispensing apparatus 400, by using the status display function, it is possible to change the display contents of the display portion 25 and the status display lamp 27 of each of the unspecified cassettes 22 as required. Thus, the user can visually inspect and confirm the dispensing information and the status information of each of the unspecified cassettes displayed on the display portion 25 and the status display lamp 27 of the unspecified cassette 22 to easily recognize the status of the unspecified cassette 22.

[Continuous Use Display Process]

Figure 26:
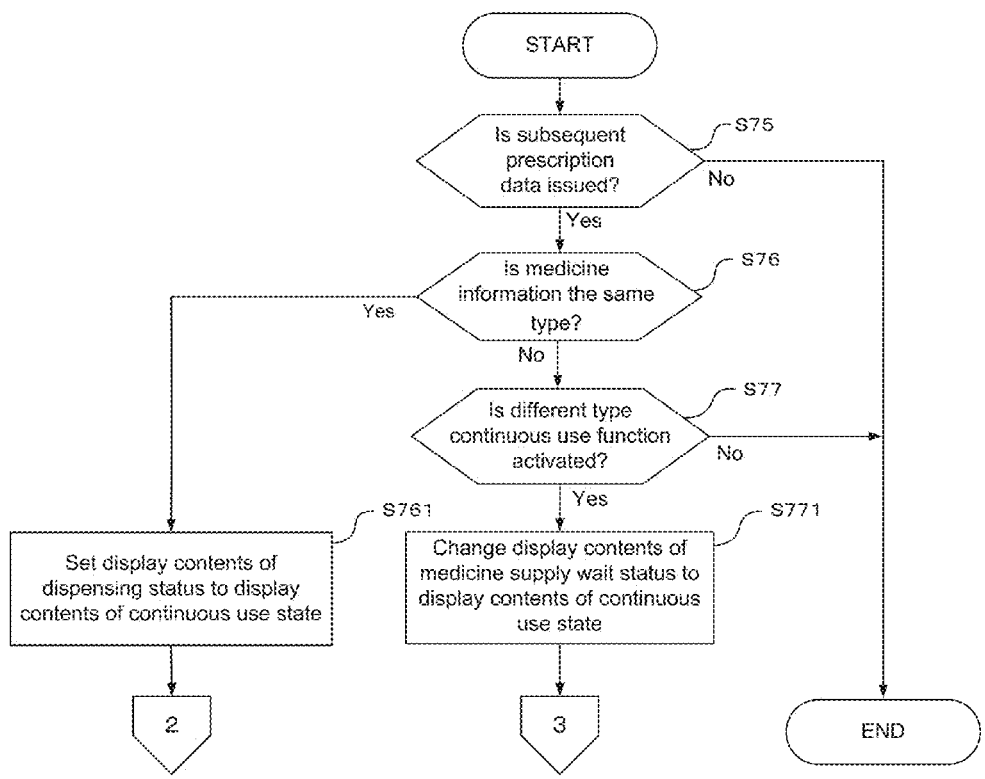
FIG. 26 is a flow chart for explaining one example of a procedure for a continuous use display process.

Next, the continuous use display process carried out at the step S711 will be described with reference to FIGS. 26 and 27. FIG. 26 is a flow chart explaining one example of a procedure of the continuous use display process. FIG. 27 is a view showing display examples of the display portion 25 and the status display lamp 27 of the unspecified cassette 22 in the continuous use display function.

<Step S75>

At a step S75, the display control portion 113 determines whether or not the subsequent prescription data is issued. The display control portion 113 shifts the process to a step S76 in a case where the display control portion 113 determines that the subsequent prescription data is issued (the case of determining "Yes" at the step S75). On the other hand, the display control portion 113 terminates the continuous use display process to shift the process to the step S72 in a case where the subsequent prescription data is not issued (the case of determining "No" at the step S75).

<Step S76>

At the step S76, for the subsequent prescription data, the display control portion 113 determines whether or not the same type of medicine information as the medicine information, which was allocated to the unspecified cassette 22 for the previous prescription data, should be allocated to the unspecified cassette 22. At this time, in the medicine dispensing apparatus 400, in a case where the subsequent prescription data contains the medicine information, which was allocated to the unspecified cassette 22 for the previous prescription data, the dispensing control portion 111 designates the medicine information in the subsequent prescription data to be allocated to the same unspecified cassette 22. Namely, in the medicine dispensing apparatus 400, the same type of medicine information contained in a sequence of the prescription data is allocated to the same unspecified cassette 22 every allocation. The dispensing control portion 111 obtains the medicine information, which was allocated to the unspecified cassette 22 for the previous prescription data, from the allocation information 121 stored in the RFID tag 26 of the unspecified cassette 22 or the storage portion 12.

The display control portion 113 shifts the process to a step S761 in a case where the display control portion 113 determines that the same type of prescription data should be allocated to the unspecified cassette 22 (the case of determining "Yes" at the step S76). On the other hand, the display control portion 113 shifts the process to a step S77 in a case where the display control portion 113 determines that a different type of medicine information should be allocated to the unspecified cassette (the case of determining "No" at the step S76).

<Step S761>

At the step S761, the display control portion 113 updates the display contents in the dispensing status at the step S64 to indicate that the unspecified cassette 22 is in a dispensing status in the continuous use of the unspecified cassette 22 (one example of the working statuses). Then, the display control portion 113 shifts the process to the step S64. With this configuration, the display contents displayed on the display portion 25 by means of the display control portion 113 at the step S64 are changed to the display contents corresponding to the dispensing status in the continuous use of the unspecified cassette 22.

In FIG. 27(A), one display example of the dispensing status in the continuous use of the unspecified cassette 22 is shown. In FIG. 27(A), characters "D8" indicating the dispensing status in the continuous use of the unspecified cassette 22 are displayed on the display area 256. The status information may be replaced with a Chinese character string meaning "Continuous use" or one Chinese character suggesting the continuous use instead of the characters "D8." The status display lamp 27 displays the dispensing status in the continuous use of the unspecified cassette 22 using the emission color or the emission mode of the status display lamp 27. For example, the display state of the status display lamp 27 indicating the dispensing status in the continuous use of the unspecified cassette 22 may be a state that a green light is turned on. Further, in the example shown in FIG. 27(A), as the dispensing information, "Alinamin" is displayed on the display area 252, "Taro YUYAMA" is displayed on the display area 253, the JAN code is displayed on the display area 254 and "50 tablets" is displayed on the display area 255.

In a case where the medicine in the unspecified cassette 22 becomes in short supply after the dispensing status is displayed at the step S64 carried out next to the step S761, the medicine shortage status is displayed at the step S651 as shown in FIG. 27(B). On the other hand, when the medicines are supplied into the unspecified cassette 22 after the medicine shortage status is displayed, the display control portion 113 allows the display portion 25 to display the display contents indicating the dispensing status in the continuous use of the unspecified cassette 22 which is set at the step S761.

<Step S77>

On the other hand, at the step S77, the display control portion 113 determines whether or not the same type continuous use function is activated in a case where the medicine information which should be allocated to the unspecified cassette 22 is not the same type of medicine information (the case of determining "No" at the step S76). At this time, the display control portion 113 shifts the process to a step S771 in a case where the display control portion 113 determines that the different type continuous use function is activated (the case of determining "Yes" at the step S77). On the other hand, the display control portion 113 terminates the continuous use display process to shift the process to the step S72 in a case where the display control portion 113 determines that different type continuous use function is inactivated (the case of determining "No" at the step S77).

<Step S771>

At the step S771, the display control portion 113 changes the display contents of the medicine supply wait status at the step S62 to display contents indicating a medicine supply wait status in the continuous use of the unspecified cassette 22 (one example of the working statuses). Then, the display control portion 113 shifts the process to the step S62. With this configuration, the display contents displayed at the step S62 are changed to the display contents corresponding to the medicine supply wait status in the continuous use of the unspecified cassette 22.

In FIG. 27(C), one display example of the medicine supply wait status in the continuous use of the unspecified cassette 22 is shown. In FIG. 27(C), characters "D9" indicating the medicine supply wait status in the continuous use of the unspecified cassette 22 are displayed on the display area 256. The status information may be a Chinese character string meaning "Visual confirmation" or one Chinese character suggesting that it is necessary to visually inspect and confirm the status of the unspecified cassette 22 at the time of supplying the medicines instead of the characters "D9." The status display lamp 27 displays the medicine supply wait status in the continuous use of the unspecified cassette 22 using the emission color or the emission mode of the status display lamp 27. For example, the display state of the status display lamp 27 indicating the medicine supply wait status in the continuous use of the unspecified cassette 22 may be a state that a green light is turned on. Further, in the example shown in FIG. 27(C), as the dispensing information, "Alinamin" is displayed on the display area 252, "Taro YUYAMA" is displayed on the display area 253, the JAN code is displayed on the display area 254 and "50 tablets" is displayed on the display area 255.

In a case where the medicines are supplied into the unspecified cassette 22 when the medicine supply wait status is displayed at the step S62 carried out next to the step S771, the display control portion 113 initializes the display contents corresponding to the medicine supply wait status which have been changed at the step S771. With this configuration, in a case where the medicine supply wait status is displayed after this initialization, the characters "D9" corresponding to the medicine supply wait status in the continuous use of the unspecified cassette 22 is not displayed, but the characters "D2" corresponding to the medicine supply wait status under a normal state are displayed.

[Exceptional Display Function]

Meanwhile, there is a case where, while the dispensation of the medicine from the unspecified cassette is carried out, an abnormality such as an unexpected restart of the medicine dispensing apparatus 400 occurs, or an operation for deleting the prescription data is carried out. In the case where the operation for deleting the prescription data is carried out, the prescription data which is an object of the operation is deleted by the control portion 11 and then the dispensation of the medicine specified in the prescription data is stopped.

In order to deal with the above case, the display control portion 113 may have an exceptional display function of allowing the display portion 25 and the status display lamp 27 of each of the unspecified cassettes 22 to display a message indicating an exceptional state. Here, one example of a procedure of an exceptional display process carried out by the display control portion 113 to display the exceptional state will be described with reference to FIGS. 28 and 29. The exceptional display process is carried out in parallel with other processes such as the medicine dispensing process, the subsequent prescription allocating process and the display control process carried out by the control portion 11. FIG. 28 is a flow chart for explaining one example of the procedure of the exceptional display process. FIG. 29 is a view showing display examples of the display portion 25 and the status display lamp 27 of the unspecified cassette 22 in the exceptional display process.

<Step S81>

First, at a step S81, the display control portion 113 determines whether or not the abnormality such as the unexpected restart of the medicine dispensing apparatus 400 occurs. The abnormality is not limited to the restart of the medicine dispensing apparatus 400. The abnormality may contain various abnormal events which are predetermined in the medicine dispensing apparatus 400. The display control portion 113 shifts the process to a step S82 in a case where the display control portion 113 determines that the abnormality occurs (the case of determining "Yes" at the step 81). On the other hand, the display control portion 113 shifts the process to a step S811 in a case where the abnormality does not occur (the case of determining "No" at the step S81).

<Step S811>

At the step S811, the display control portion 113 determines whether or not the operation for deleting the prescription data containing the medicine information allocated to the unspecified cassette 22 has been carried out during the dispensation of the medicine in the medicine dispensing apparatus 400. The operation for deleting the prescription data is a user operation performed on the operating portion 14 which is carried out, for example, when a selection screen for the prescription data is displayed on the monitor 13. The display control portion 113 shifts the process to a step S812 in a case where the display control portion 113 determines that the operation for deleting the prescription data is carried out (the case of determining "Yes" at the step 811). On the other hand, the display control portion 113 returns the process to the step S81 in a case where the operation for deleting the prescription data is not carried out (the case of determining "No" at the step S811). The described operation for deleting the prescription data does not contain an operation carried out before the issuing of the prescription data (before the allocation to the unspecified cassette 22) or before the dispensation of the medicine for the prescription data starts.

As described above, the display control portion 113 carries out the display control process (see FIGS. 22 and 23) with monitoring the occurrence of the abnormality and the operation for deleting the prescription data as an interrupt event. Thus, the display control portion 113 interrupts the display control process depending on the occurrence of the interrupt event to carry out the processes after the step S82 or the step S812.

<Step S82>

At the step S82, the display control portion 113 allows the display portion 25 and the status display lamp 27 of the unspecified cassette 22 to display the status information indicating an abnormality occurrence status (one example of the working statuses).

Figure 29A:
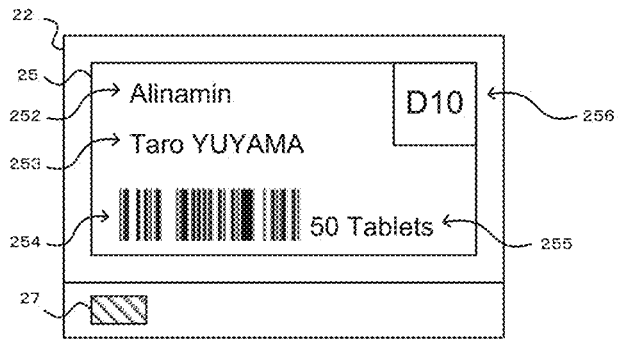
FIG. 29 is a view showing a display example at the time of carrying out the exceptional display process.

In FIG. 29(A), one display example of the abnormality occurrence status is shown. In FIG. 29(A), characters "D10" indicating the abnormality occurrence status are displayed on the display area 256. The status information may be replaced with a Chinese character string meaning "Manual collection" or one Chinese character suggesting a status where a manual collecting of the medicine in the unspecified cassette 22 is required because of the occurrence of the abnormality. The status display lamp 27 displays the abnormality occurrence status using the emission color or the emission mode of the status display lamp 27. For example, the display state of the status display lamp 27 indicating the abnormality occurrence status may be a state that an orange light (or a red light) is turned on. In the example shown in FIG. 29(A), as the dispensing information, "Alinamin" is displayed on the display area 252, "Taro YUYAMA" is displayed on the display area 253, the JAN code is displayed on the display area 254 and "50 tablets" is displayed on the display area 255.

Figure 29B:
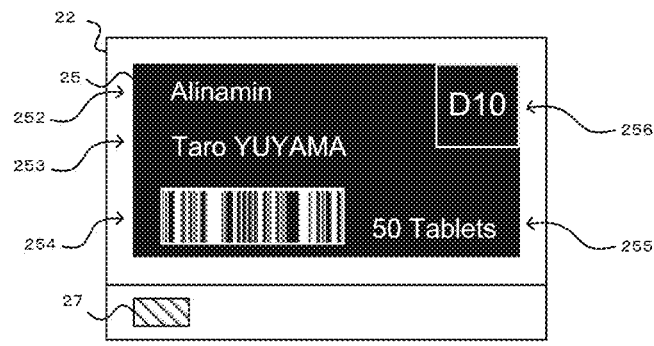
Figure 29C:
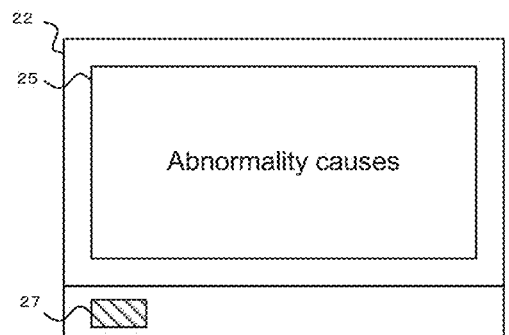

In FIGS. 29(B) and 29(C), display examples of the abnormality occurrence status are shown. In the example shown in FIG. 29(B), the display contents of the display portion 25 are the same as the display contents shown in FIG. 29(A), but a character color and a background color in the display areas 252 to 256 of the display portion 25 are inversed to emphatically display the abnormality occurrence status. As such a method for emphatically displaying the abnormality occurrence status, a method of blinking whole of the display contents of the display portion 225 or the like may be used. Further, in the example shown in FIG. 29(C), the display areas 252 to 256 of the display portion 25 are in the non-display state and only a character string "Abnormality occurs" is emphatically displayed. By displaying the display contents which are apparently different from the display contents in the normal status on the display portion 25, it is possible to easily make the user recognize the abnormality occurrence status.

<Step S812>

At the step S812, the display control portion 113 allows the display portion 25 and the status display lamp 27 of the unspecified cassette 22 to display the status information indicating a prescription data deleting status (one example of the working statuses).

Figure 29D:
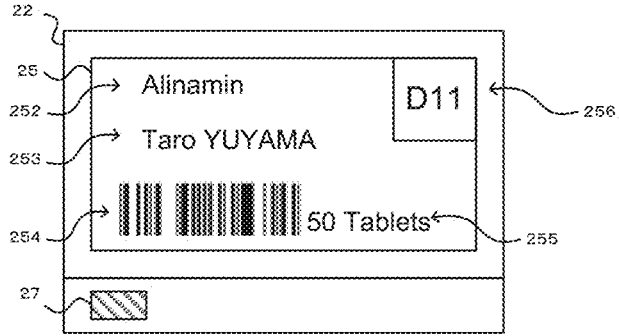
Figure 31A:
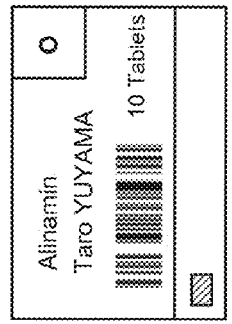
FIG. 31 is a view showing another display example of the display portion of the unspecified cassette.
Figure 31B:
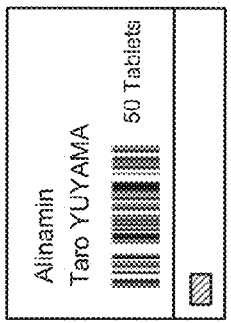
Figure 31D:
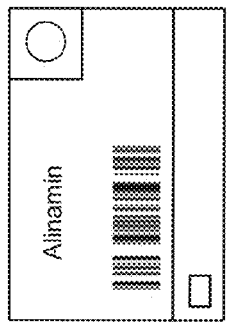
Figure 31C:
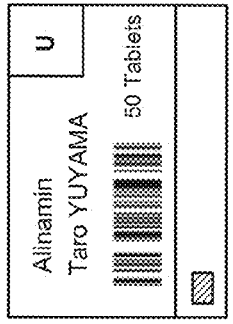
Figure 31E:
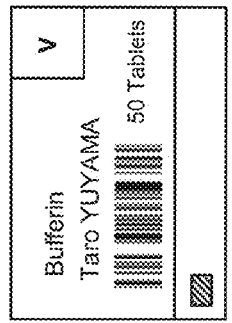
Figure 31G:
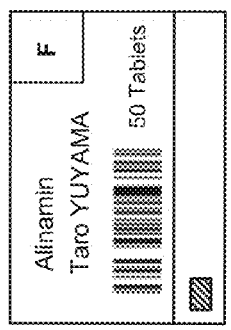
Figure 31F:
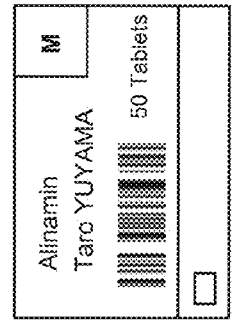
Figure 31H:
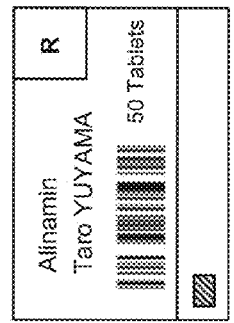
Figure 31I:

In FIG. 29(D), one display example of the prescription data deleting status is shown. In the example shown in FIG. 29(D), characters "D11" indicating the prescription data deleting status are displayed on the display area 256. The status information may be replaced with a Chinese character string meaning "Deleting" or one Chinese character suggesting the prescription data deleting status instead of the characters "D11." The status display lamp 27 displays the prescription data deleting status using the emission color or the emission mode of the status display lamp 27. For example, the display state of the status display lamp 27 may be a state that an orange light (or a red light) is turned on. In the example shown in FIG. 29(D), as the dispensing information, "Alinamin" is displayed on the display area 252, "Taro YUYAMA" is displayed on the display area 253, the JAN code is displayed on the display area 254 and "50 tablets" is displayed on the display area 255.

<Step S83>

Then, at a step S83, the display control portion 113 waits for the removing and mounting operating of the unspecified cassette 22 in the same manner as the step S72 (the case of determining "No" at the step S83). The step S83 is a process for concluding that the user confirms the status of the unspecified cassette 22 after the occurrence of the abnormality or the deleting of the prescription data. At this time, the display control portion 113 shifts the process to a step S84 in a case where the display control portion 113 determines that the removing and mounting operation is carried out (the case of determining "Yes" at the step S83). In the medicine dispensing apparatus 400, the dispensing control portion 111 does not carry out the dispensation of the medicine for the subsequent prescription data until each of the unspecified cassettes 22 is removed and mounted after the occurrence of the abnormality or the deleting of the prescription data. With this configuration, it is possible to prevent the dispensation of the medicine for the subsequent prescription data from starting under a state that the status of each of the unspecified cassettes 22 has not yet been fixed.

<Step S84>

At the step S84, the display control portion 113 branches the process depending on whether or not the previous time medicine display setting is activated in the same manner as the step S73. At this time, the display control portion 113 shifts the process to a step S841 in a case where the previous time medicine display setting is activated (the case of determining "Yes" at the step S84). On the other hand, the display control portion 113 shifts the process to a step S85 in a case where the previous time medicine display setting is inactivated (the case of determining "No" at the step S84).

<Step S841>

At the step S841, the display control portion 113 allows the display portion 25 and the status display lamp 27 of the unspecified cassette 22 to display a message indicating the non-allocated state in the same manner as the step S731 (see FIG. 24(B)). Then, the display control portion 113 returns the process to the step S81 and restarts the display control process from the step S61.

<Step S85>

On the other hand, at the step S85, the display control portion 113 allows the display portion 25 and the status display lamp 27 of the unspecified cassette 22 to display a message indicating the non-allocated state in the same manner as the step S74 (see FIG. 24(A)). Then, the display control portion 113 returns the process to the step S81 and restarts the display control process from the step S61.

As described above, in the case where the exceptional event such as the occurrence of the abnormality and the deleting of the prescription data occurs, the medicine dispensing apparatus 400 can allow the display portion 25 and the status display lamp 27 to display a message indicating that the exceptional event occurs by means of the exceptional display function. Thus, it is possible to prompt the user to carry out a confirming action for the unspecified cassettes 22 in the case where the exceptional event occurs.

[Transition Example of the Display State]

Figure 30:
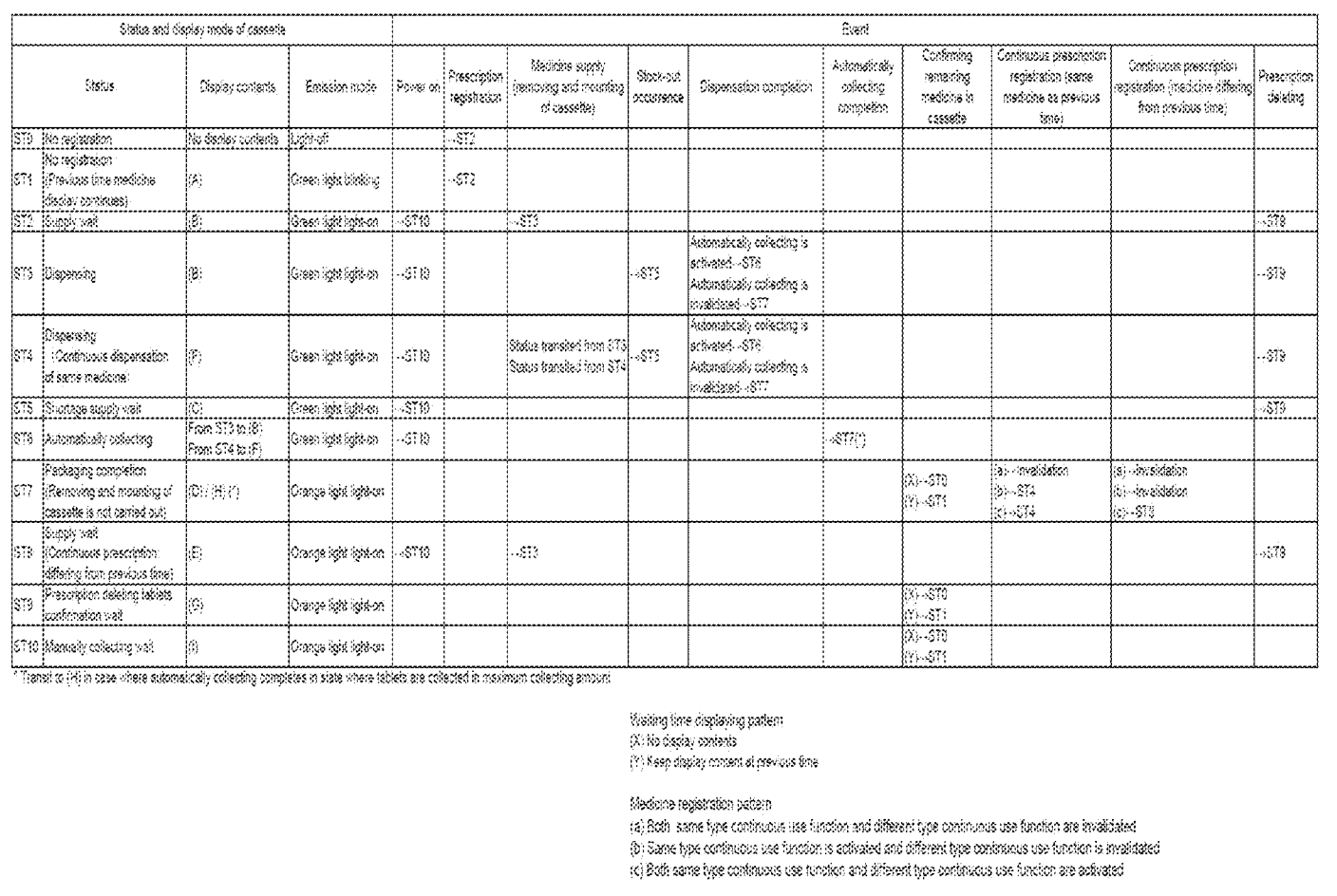

Here, a concrete example of a relationship between the status of the unspecified cassette 22 and the display contents of the display portion 25 in the medicine dispensing apparatus 400 will be described with reference to FIGS. 30 and 31. FIG. 30 is a transition table showing the transitions of the status of the unspecified cassette and the display contents of the display portion 25. FIG. 31 is a view showing concrete display examples of the display portion 25 in each status in the transition table.

As shown in the transition table in FIG. 30, the statuses of the unspecified cassette 22 can be roughly categorized into eleven groups "status ST0" to "status ST10" and the display contents of the display portion 25 and the status display lamp 27 are allocated to each of the statuses ST0 to ST10.

Specifically, the status ST0 corresponds to the status "No registration" in which no medicine information is allocated to the unspecified cassette 22. The display contents of the display portion 25 corresponding to the status ST0 are "No display" and the emission mode of the status display lamp 27 corresponding to the status ST0 is "Light-off mode." In the transition table shown in FIG. 30, it is described that the status ST0 transits to the status ST1 in a case where an event "prescription registration," in which the medicine information corresponding to the prescription data is allocated to the unspecified cassette 22, occurs under the status ST0.

Next, the status ST1 corresponds to a status in which the unspecified cassette 22 is removed and mounted under the status ST7, the status ST9 or the status ST10 and it is confirmed that the remaining medicine does not exist in the unspecified cassette 22. Further, the status ST1 corresponds to the status "No registration" in which the medicine information is not allocated to the unspecified cassette 22. The display contents of the display portion 25 corresponding to the status ST1 are "(A)" corresponding to the display example shown in FIG. 31(A) and the emission mode of the status display lamp 27 corresponding to the status ST1 is "Light-off mode." In the transition table, it is described that the status ST1 transits to the status ST2 in a case where the event "Prescription registration," in which the medicine information corresponding to the prescription data is allocated to the unspecified cassette 22, occurs under the status ST1.

The status ST2 corresponds to a status "Supply wait" which continues until the medicine is supplied into the unspecified cassette 22. The display contents of the display portion 25 corresponding to the status ST2 are "(B)" corresponding to the display example shown in FIG. 31(B) and the emission mode of the status display lamp 27 corresponding to the status ST2 is "Green light blinking mode." The status ST2 transits to the status ST10 in a case where an event "Power on," in which power of the medicine dispensing apparatus 400 is reset, occurs under the status ST2. This procedure for the event "Power on" can be also carried out under the other statuses ST3 to ST6 and ST8. The status ST2 transits to the status ST3 in a case where it is determined that the unspecified cassette 22 is removed and mounted to supply the medicine into the unspecified cassette 22. Further, the status ST2 transits to the status ST9 when an event "prescription deleting," in which the prescription data containing the medicine information on the medicine allocated to the unspecified cassette 22 is deleted, occurs under the status S2. The procedure for the event "Prescription deleting" can be also carried out under the statuses ST3 to ST5 and ST8.

The status ST3 corresponds to a status "dispensing" in which the packaging operation is being carried out with the unspecified cassette 22. The display contents of the display portion 25 corresponding to the status ST3 are "(B)" and the emission mode of the status display lamp 27 corresponding to the status ST3 is "Green light light-on mode." The status ST3 transits to the status ST5 in a case where an event "Stock-out occurrence," in which the medicine in the unspecified cassette 22 becomes in short supply, occurs under the status ST3. On the other hand, the status ST3 transits to the status ST6 in a case where an event "dispensation completion," in which the dispensation of the medicine from the unspecified cassette 22 completes, occurs under the ST3. Alternatively, the status ST3 transits to the status ST7 in a case where the remaining medicine collecting process is not carried out under the status ST3.

The status ST4 corresponds to a situation in which at least one of the same type continuous use function and the different type continuous use function is activated and an event "Continuous prescription registration," in which the same type of medicine as the previous time is allocated to the unspecified cassette 22, occurs under the status ST7. The status ST4 also corresponds to the status "dispensing" in which the packaging operation is being carried out with the unspecified cassette 22. The display contents of the display portion 25 corresponding to the status ST4 are "(F)" corresponding to the display example shown in FIG. 31(F) and the emission mode of the status display lamp 27 corresponding to the status ST7 is "Green light light-on mode." The status ST4 transits in the same manner as the status ST3.

The status ST5 corresponds to a status "Stock-out supply wait" which continues until the medicine is supplied into the unspecified cassette 22 after the medicine in the unspecified cassette 22 becomes in short supply. The display contents of the display portion 25 corresponding to the status ST5 are "(C)" corresponding to the display example shown in FIG. 31(C) and the emission mode of the status display lamp 27 corresponding to the status ST5 is "Green light blinking mode." The status ST5 returns to the status ST3 in a case where an event "Medicine supply" occurs under the status ST5 and a previous status just before the status ST5 is the status ST3. On the other hand, the status ST5 returns to the status ST4 in a case where the event "Medicine supply" occurs under the status ST5 and the previous status just before the status ST5 is the status ST4.

The status ST6 corresponds to a status "Automatically collecting" in which the remaining medicine collecting process is being carried out for the unspecified cassette 22. The display contents of the display portion 25 corresponding to the status ST6 are "(B)" corresponding to the display example shown in FIG. 31(B) in a case where a previous status just before the status ST6 is the status ST3. On the other hand, the display contents of the display portion 25 corresponding to the status ST6 are "(F)" corresponding to the display example shown in FIG. 31(F) in a case where the previous status just before the status ST6 is the status ST4. In both above cases, the emission mode of the status display lamp 27 is "Orange light light-on mode." The status ST6 transits to the status ST7 in a case where an event "Automatically collecting completion," in which the remaining medicine collecting process completes, occurs under the status ST6.

The status ST7 corresponds to a status "Packaging completion" in which the packaging operation using the unspecified cassette 22 completes. Under the status ST7, the removing and mounting operation of the unspecified cassette 22 has not yet been carried out. The display contents of the display portion 25 corresponding to the status ST7 are "(D)" corresponding to the display example shown in FIG. 31(D) in a case where the remaining medicine collecting process normally completes. On the other hand, the display contents of the display portion 25 corresponding to the status ST7 are "(H)" corresponding to the display example shown in FIG. 31(H) in a case where the remaining medicine collecting process is terminated because the tablets are collected in a maximum collecting amount. In the both cases, the emission mode of the status display lamp 27 is "Orange light light-on mode."

In a case where the unspecified cassette 22 is removed and mounted and an event "Confirming remaining medicine in cassette" in which it is determined that the remaining medicine does not exist in the unspecified cassette 22, the status ST7 transits to the status ST0 or the status ST1 depending on the inactivated ("X" in the transition table) and the activation ("Y" in the transition table) of the previous medicine display setting which corresponds to a display pattern while the display portion 25 is ready and waiting.

The status ST7 transits depending on whether or not each of the same type continuous use function and the different type continuous use function is activated in a case where an event "Continuous prescription registration (the same medicine as the previous time)," in which the prescription data is issued to allocate the same type of medicine as the medicine which was allocated to the unspecified cassette 22 before to the unspecified cassette 22, occurs under the status ST7. Specifically, the status ST7 transits to the status ST4 in cases "(b), (C)" where at least one of the same type continuous use function and the different type continuous use function is activated. On the other hand, the status ST7 continues in a case "(a)" where both the same type continuous use function and the different type continuous use function are inactivated.

On the other hand, the status ST7 transits depending on whether or not each of the same type continuous use function and the different type continuous use function is activated in a case where an event "Continuous prescription registration (the medicine differing from the previous time)," in which the prescription data is issued to allocate the different type of medicine differing from the medicine which was allocated to the unspecified cassette 22 before to the unspecified cassette 22, occurs under the status ST7. Specifically, the status ST7 transits to the status ST8 in the case "(c)" where the different type continuous use function is activated. On the other hand, the status ST7 continues in the cases "(a), (b)" where the different type continuous use function is inactivated.

The status ST8 corresponds to a status "Supply wait" which continues until the medicine allocated at the status ST8 is supplied into the unspecified cassette 22. The display contents of the display portion 25 corresponding to the status ST8 are "(E)" corresponding to the display example shown in FIG. 31(E) and the emission mode of the status display lamp 27 corresponding to the status ST8 is "Orange light light-on mode." The status ST8 transits to the status ST3 in a case where the event "Medicine supply" occurs under the status ST8.

The status ST9 corresponds to a status "prescription deleting tablet confirmation wait" which continues until the unspecified cassette 22 is removed and mounted to confirm the remaining medicine in the unspecified cassette 22 after the event "Prescription deleting" occurs. The display contents of the display portion 25 corresponding to the status ST9 are "(G)" corresponding to the display example shown in FIG. 31(G) and the emission mode of the status display lamp 27 corresponding to the status ST9 is "Orange light light-on mode." The status ST9 transits to the status ST0 or the status ST1 depending on the inactivation ("X" in the transition table) and the activation ("Y" in the transition table) of the previous medicine display setting in a case where the event "Confirming remaining medicine in cassette" occurs under the status ST9.

The status ST10 corresponds to a status "manual collecting wait" which continues until the unspecified cassette 22 is removed and mounted to confirm the remaining medicine in the unspecified cassette 22 after the event "Power on" occurs. The display contents of the display portion 25 corresponding to the status ST10 are "(I)" corresponding to the display example shown in FIG. 31(I) and the emission mode of the status display lamp 27 corresponding to the status ST10 is "Orange light light-on mode." The status ST10 transits to the status ST0 or the status ST1 depending on the inactivation ("X" in the transition table) and the activation ("Y" in the transition table) of the previous medicine display setting in a case where the event "Confirming remaining medicine in cassette" occurs under the status ST10.

<Specified Cassette Display Function>

As shown in FIG. 16, it is possible to take a configuration in which a display portion 291 and a status display lamp 292 are provided at each of the specified cassettes 21 and the display control portion 133 has a specified cassette display function of controlling display states of the display portion 291 and the status display lamp 292 of the specified cassette 21. In this regard, the display portion 291 and the status display lamp 292 may be provided at each of the mounting portions 211 which correspond to each of the specified cassettes 21 and on which each of the specified cassette 21 should be mounted. In this case, the display portion 291 is one example of specified medicine display means.

The display portion 291 is an electronic paper provided on a front surface of the specified cassette 21 like the display portion 25. The display portion 291 may be a liquid crystal display panel or the like. The status display lamp 291 is a light source such as an LED used for indicating a working status of the specified cassette 21 using an emission color or an emission mode and provided on the front surface of the specified cassette 21 together with the display portion 25. For example, the emission mode contains a light-off mode, a light-on mode, a light blinking mode or the like. The display control portion 113 changes the display state of the status display lamp 292 according to the working status of the specified cassette 21.

In the medicine dispensing apparatus 400 having such a configuration, the display control portion 113 allows the display portion 291 to display predetermined various information as required. In this case, the display control portion 113 carrying out this display process is one example of specified display control means. Examples of the various information include information related to the medicine which should be contained in the specified cassette 21, such as medicine identification information, a remaining amount, a lot number and an expiration date and the like. The medicine identification information is a medicine name, a medicine code, a JAN code (barcode), an RSS code (GS1 data bar), a QR code (registered trademark) or the like. Further, the JAN code (barcode), the RSS code (GS1 data bar) or the QR code (registered trademark) may contain more information such as the lot number and the expiration date of the medicine. With this configuration, the user can easily recognize the information on the medicine contained in the specified cassette 21, such as the medicine identification information, the remaining amount, the lot number and the expiration date.

Especially, it is preferred that the display control portion 113 allows the display portion 291 to display the remaining amount of the medicine contained in the specified cassette 21. For example, the display control portion 113 receives an input of a supplied mount of the medicine by means of a user operation performed on the operating portion 14 or the like at the time of supplying the medicine into the specified cassette 21. Alternatively, at the time of reading the barcode, which is written on a medicine container such as an original medicine bottle for the medicine which should be supplied into the specified cassette 21, by means of the barcode reader 7, the display control portion 113 may receive a medicine amount contained in the information of the barcode as the supplied amount. In this case, the display control portion 133 receiving the input of the supplied amount is one example of the supplied amount receiving means.

Then, the display control portion 113 increases the remaining amount of the medicine displayed on the display portion 291 according to the supplied amount. For example, in a case where the current remaining amount of the medicine in the specified cassette 21 is "0," the supplied amount is displayed on the display portion 291 as the remaining amount of the medicine. In a case where the current remaining amount of the medicine in the specified cassette 21 is not "0," the display control portion 133 allows the display portion 291 to display an added value of the remaining amount of the medicine and the supplied amount as the current remaining amount of the medicine.

On the other hand, the display control portion 113 obtains a dispensed amount of the medicine from a counter (one example of specific medicine counting means) for counting the tablets dispensed from the specified cassette 21 with an optical sensor or the like. The display control portion 113 may obtain the dispensed amount of the medicine dispensed from the specified cassette 21 on the basis of the prescription data issued by the medicine dispensing apparatus 400. Then, the display control portion 113 reduces the remaining amount of the medicine displayed on the display portion 113 according to the dispensed amount. As a result, the current remaining amount of the medicine is displayed on the display portion 291 of the specified cassette 21.

[Powdered Medicine Cassette Display Function]

As shown in FIG. 16, in the medicine dispensing apparatus 400, the powdered medicine supplying unit 3 may include a plurality of powdered medicine cassettes 33 for respectively dispensing powdered medicine contained in the powdered medicine cassettes 33 in advance. Since the medicine dispensing apparatus 400 having such a configuration can automatically dispense the powdered medicine from each of the powdered medicine cassettes 33, it is possible to reduce a user work for measuring the powdered medicine, supplying the powdered medicine or the like.

Specifically, the powdered medicine supplying unit 3 may further include a cassette placing portion, a cassette moving mechanism and a powdered medicine dispensing mechanism. The plurality of the powdered medicine cassettes 33 are placed on the cassette placing portion. The cassette moving mechanism moves the powdered medicine cassette 33, which is selected by the dispensing control portion 111 depending on the input of the prescription data among the powdered medicine cassettes 33, from the cassette placing portion toward the supplying portion 32 or the supplying portion 33 of the powdered medicine supplying unit 3. For example, the cassette moving mechanism is a robot arm for holding the powdered medicine cassette 33 to move the powdered medicine cassette 33. The powdered medicine dispensing mechanism dispenses the powdered medicine with measuring the amount of the powdered medicine to be dispensed from each of the powdered medicine cassettes 33. The powdered medicine dispensing mechanism includes a vibrating feeder for vibrating the powdered medicine cassette 33 to dispense the powdered medicine from the powdered medicine cassette 33 by a predetermined amount and a measuring portion for measuring an amount of the powdered medicine to be conveyed by the vibrating feeder.

As shown in FIG. 16, it is possible to take a configuration in which a display portion 331 and a status display lamp 332 are provided at each of the powdered medicine cassettes 33 and the display control portion 113 has a powdered medicine display function of controlling display states of the display portion 331 and the status display lamp 27. In this regard, the display portion 331 and the status display lamp 27 may be provided at mounting portions which respectively correspond to the powdered medicine cassettes 33 and on which the powdered medicine cassettes 33 should be mounted.

The display portion 331 is an electronic paper provided on a front surface of the powdered medicine cassette 33 like the display portion 25. The display portion 331 may be a liquid crystal display panel or the like. The status display lamp 332 is a light source such as an LED used for indicating a work status of the powdered medicine cassette 33 using an emission color or an emission mode and provided on the front surface of the powdered medicine cassette 33 together with the display portion 331. For example, the emission mode contains a light-off mode, a light-on mode, a light blinking mode or the like. The display control portion 113 changes the display state of the status display lamp 332 according to the working status of the powdered medicine cassette 33.

In the medicine dispensing apparatus 400 having such a configuration, the display control portion 113 allows the display portion 331 to display predetermined various information as required. In this case, the display control portion 113 carrying out this display process is one example of display control means. Examples of the various information include information related to the medicine which should be contained in the powdered medicine cassette 33, such as medicine identification information, a remaining amount, a lot number and an expiration date. The medicine identification information is a medicine name, a medicine code, a JAN code (barcode), an RSS code (GS1 data bar), a QR code (registered trademark) or the like. The JAN code (barcode), the RSS code (GS1 data bar) or the QRR code (registered trademark) may contain more information such as the lot number and the expiration date of the medicine.

Especially, it is preferred that the display control portion 113 allows the display portion 331 to display the remaining amount of the medicine contained in the powdered medicine cassette 33. For example, the display control portion 113 receives an input of a supplied amount of the medicine by means of a user operation performed on the operating portion 13 or the like at the time of supplying the medicine into the powdered medicine cassette 33. Alternatively, at the time of reading a barcode which is written on a medicine container such as an original medicine bottle for the medicine which should be supplied into the powdered medicine cassette 33 by means of the barcode reader 7, the display control portion 113 may receive an amount of the medicine contained in information of the barcode as the supplied amount. In this case, the display control portion 113 receiving the input of the supplied amount is one example of supplied amount receiving means.

The display control portion 113 increases the remaining amount of the medicine displayed on the display portion 331 according to the supplied amount. For example, in a case where the current remaining amount of the medicine in the powdered medicine cassette 33 is "0," the supplied amount is displayed on the display portion 331 as the remaining amount of the medicine. In a case where the remaining amount of the medicine in the powdered medicine cassette 33 is not "0," the display control portion 113 allows the display portion 331 to display an added value of the remaining amount of the medicine and the supplied amount as the current remaining amount of the medicine.

On the other hand, the display control portion 113 obtains a dispensed amount of the medicine dispensed from the powdered medicine cassette 33 from the powdered medicine dispensing mechanism. The display control portion 113 may obtain the dispensed amount of the medicine dispensed from the powdered medicine cassette 33 on the basis of the prescription data issued by the medicine dispensing apparatus 400. Then, the display control portion 113 reduces the remaining amount of the medicines displayed on the display portion 331 according to the supplied amount.

[Remaining Medicine Reuse Function]

In the medicine dispensing apparatus 400, in a case where the medicine remains in the unspecified cassette after the medicine is dispensed from the unspecified cassette 22 in a required amount, it is possible to collect the remaining medicine by carrying out the remaining medicine collecting process. Especially, in the medicine dispensing apparatus 400, the control portion 61 allows the packaging unit 5 to separately package the medicines respectively contained in the unspecified cassettes 22 into different sheets of packaging paper 52 in correspondence with the types of medicines. Specifically, one type of medicine contained in the unspecified cassette 22 is contained into one sheet of the packaging paper 52 to collect the one type of medicine. Thus, in the remaining medicine collecting process, the sheets of the packaging paper 52 are outputted in the same number as the number of the unspecified cassettes 22 used for dispensing the medicines specified in the prescription data. Hereinafter, the sheet of the packaging paper 52 into which the remaining medicine collected from the unspecified cassette 22 should be contained will be referred to as "collecting package 521." The user puts the collecting packages 521 into a container provided in the vicinity of the medicine dispensing apparatus 400 or the like.

As described below, the medicine dispensing apparatus 400 has a remaining medicine reuse function of supporting reuse of the remaining medicines collected into the collecting packages 521 in the remaining medicine collecting process. Specifically, in the medicine dispensing apparatus 400, as shown in FIG. 16, the control portion 11 includes a remaining medicine control portion 114 for carrying out a process of supporting the reuse of the medicine collected into the packaging paper 52 in the remaining medicine collecting process. The control portion 11 carries out various processes with the CPU depending on various programs preliminary stored in storage means such as the ROM, the EEPROM and the storage portion 12 which serve as the remaining medicine control portion 114. In this case, the remaining control portion 114 is one example of remaining medicine control means.

As shown in FIG. 16, the medicine dispensing apparatus 400 includes a printer 53 (one example of printing means) which can print information such as a character or an image on the packaging paper 52 used in the packaging unit 5 on the basis of a control instruction from the control portion 11 or the control portion 61. In the medicine dispensing apparatus 400, it is possible to print the information on the packaging paper 52 in which the medicine should be contained by the time when the medicine is contained in the packaging paper 52 after the dispensation of the medicine from the tablet supplying unit 5. In this regard, such a configuration is disclosed in JP 2008-62945A.

Specifically, the tablet supplying unit 2 includes one or a plurality of buffer portions for temporarily storing the medicine dispensed from the specified cassette 21 or the unspecified cassette 22 which are provided at a front stage of the packaging unit 5. The control portion 61 allows the printer 53 to print information such as the dispensed amount of the medicine dispensed from the specified cassette 21 or the unspecified cassette 22 on the packaging paper 52 after the medicine is dispensed from the specified cassette 21 or the unspecified cassette 22. Then, the control portion 61 controls the packaging unit 5 to package the medicine waiting in the buffer portion into the packaging paper 52 when the packaging paper 52 is conveyed to the supplying portion for the medicine in the packaging unit 5.

At this time, the control portion 61 allows the printer 53 to print on the collecting package 521 information such as the medicine name, the medicine code, the JAN code (barcode), a collected amount and a collecting number (No.) of the medicine supplied or dispensed from the unspecified cassette 22 into the collecting package 521 in the remaining medicine collecting process. With this configuration, the user can easily recognize the collected amount of the medicine contained in the collecting package 521. Each of the medicine name, the medicine code and the JAN code is one example of identification information for identifying the medicine. In this regard, the JAN code is one example of a one-dimensional code indicating the identification information for the medicines. It is possible to use other types of one-dimensional code such as an RSS code (GS1 data bar) or a two-dimensional code such as a QR code (registered trademark) instead of the JAN code. The control portion 61 obtains the collected amount of the medicine from the counter for counting the medicine dispensed from the unspecified cassette 22 in the remaining medicine collecting process. The collecting number is a numerical number allocated to the collecting package 521 consecutively in serial numbers by the control portion 61. The control portion 61 carrying out this printing process for printing the information on the collecting package 521 with the printer 53 is one example of print control means.

FIG. 32(A) is a view showing one example of a print result of the charta sheet 51 for one prescription data outputted from the medicine dispensing apparatus 400. As shown in FIG. 32(A), the patient name, the administration time, the medicine name and the number of the medicine are printed on each sheet of the packaging paper 52 of the charta sheet 51 in which the medicines are separately packaged according to the prescription data. Further, on the first sheet of the packaging paper 52 in the charta sheet 51, inspecting medicine typing information 522 used for inspecting the medicine selectively packaged into the sheets of the packaging paper 52 of the charta sheet 51 on the basis of the prescription data is printed.

The same number of the collecting packages 521 as the number of the unspecified cassettes 22 used at the time of dispensing the medicines specified in the prescription data are provided at the end of the charta sheet 51. On each of the collecting packages 521, the collecting number for identifying the collecting package 521 and a character string "collecting package" indicating that the remaining medicine collected from the unspecified cassette 22 is contained are printed. Further, on the collecting package 521, the medicine name corresponding to the remaining medicine contained in the collecting package 521, the barcode indicating the JAN code corresponding to the remaining medicine and the collected amount of the remaining medicine contained in the collecting package 521 are printed. For example, as shown in FIG. 32(A), on the collecting package 521 having the collecting number "1," a medicine name "Medicine M1" is printed as the medicine name of the remaining medicine and an amount "4 tablets" is printed as the collected amount. In the same manner, on the collecting package 521 having the collecting number "2," a medicine name "Medicine M2" is printed as the medicine name of the remaining medicine and "3 tablets" is printed as the collected amount.

Figure 33:
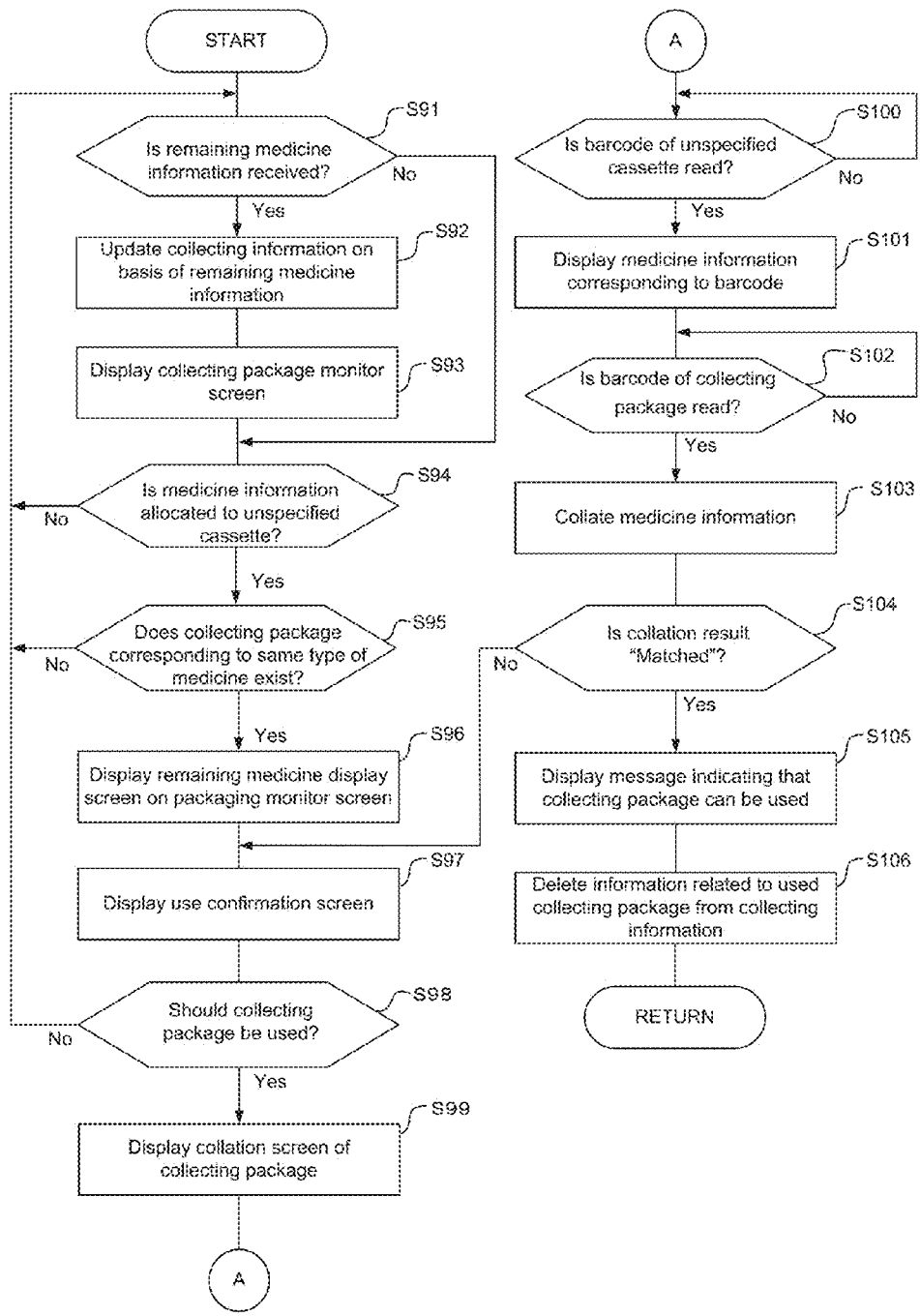
FIG. 33 is a flow chart for explaining one example of a procedure for a remaining medicine reuse process.

Hereinafter, one example of a procedure of a remaining medicine control process carried out by the remaining medicine control portion 114 will be described with reference to FIG. 33. The remaining medicine control process is carried out in parallel with the other processes such as the medicine dispensing process, the subsequent prescription allocating process, the display control process and the exceptional display process carried out by the control portion 11.

In the medicine dispensing apparatus 400 having the remaining medicine reuse function, the steps S10, S16 and S17 for the medicine dispensing process and the package control process (see FIG. 11) are omitted. Further, in the medicine dispensing apparatus 400, the dispensing control portion 111 reports whether or not the remaining medicine collecting process should be carried out at the time of issuing the starting request for the packaging operation at the step S7. In a case where the control portion 61 receives a report indicating that the remaining medicine collecting process should be carried out from the dispensing control portion 111, the control portion 61 carries out the remaining medicine collecting process following to the packaging operation at the step S14. Then, the control portion 61 transmits the medicine name, the medicine code and the number of the collecting packages 521 of the remaining medicines dispensed from each of the unspecified cassettes 22 in the remaining medicine collecting process to the control portion 11 as remaining medicine information. In a case where the remaining medicine is not dispensed from each of the unspecified cassettes 22 in the remaining medicine collecting process, the control portion 61 may not transmit the remaining medicine information to the control portion 11.

<Step S91>

First, at a step S91, the remaining medicine control portion 114 waits for a reception of the remaining medicine information from the control portion 61 (the case of determining "No" at the step S91). Then, the remaining medicine control portion 114 shifts the process to a step S92 in a case where the remaining medicine control portion 114 receives the remaining medicine information (the case of determining "Yes" at the step S91).

<Step S92>

At the step S92, the remaining medicine control portion 114 stores the remaining medicine information as collecting information 123 related to the medicines collected in the remaining medicine collecting process. In this case, the remaining medicine control portion 114 carrying out this storing process is one example of storage control means. The collecting information 123 contains information on the collecting package 521 which has not yet been used after the collecting package 521 is collected in the remaining medicine collecting process in the medicine dispensing apparatus 400. In FIG. 34(A), one example of the collecting information 123 is shown. In the collecting information 123 shown in FIG. 34(A), the collecting number of the collecting packages 521 which have not yet been used and the medicine code of the remaining medicine contained in the collecting package 521 which has not been used are contained. With this configuration, the remaining medicine control portion 114 can determine, on the basis of the collecting information 123, whether or not the collecting packages 521 corresponding to each type of medicines exist and the number of the collecting packages 521. Specifically, from the example shown in FIG. 34(A), it is possible to determine that two collecting packages 521 having the medicine name "Medicine M1" and one collecting package 521 having the medicine name "Medicine M2" remain unused.

<Step S93>

At a step S93, the remaining medicine control portion 114 allows the monitor 13 to display the collecting information 123. In this case, the remaining medicine control portion 114 carrying out this display process for displaying information related to the collecting information 123 is one example of collecting information display means. Specifically, the remaining control portion 114 allows the monitor 13 to display a collecting package monitor screen 131 indicating the information on the collecting package 521 which has not yet been used on the basis of the collecting information 123. The collecting package monitor screen 131 may be displayed as a pop-up screen so as to overlap a packaging monitor screen 132 described below (see FIG. 36). The remaining control portion 114 allows the monitor 13 to display the collecting package monitor screen 131 indicating the collecting information 123 depending on an operation performed on an operating key provided for displaying the collecting information 123 on the packaging monitor screen 132 (see FIG. 36). With this configuration, the user can refer to the collecting information 123 to determine whether or not the medicine in the collecting package 521 can be used at the time of supplying the medicine into the unspecified cassette 22.

Figure 35A:
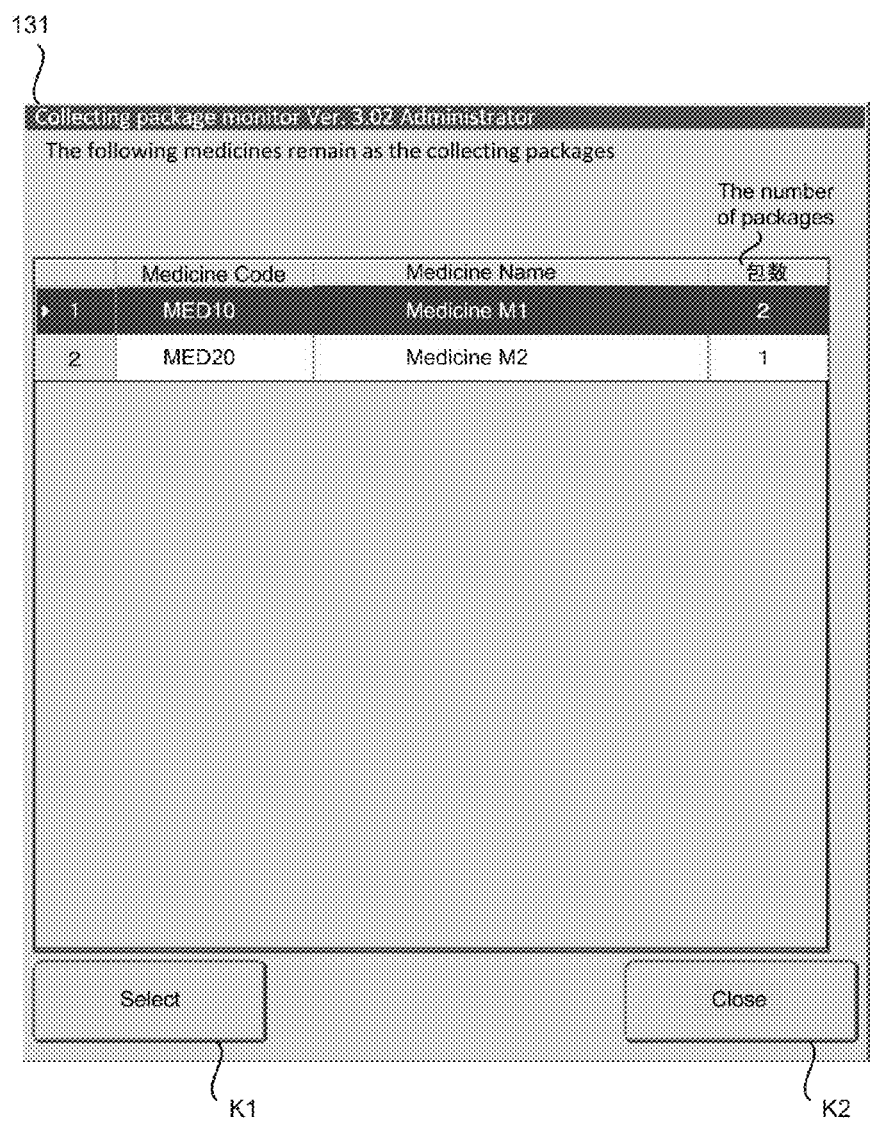
FIG. 35 is a view showing one example of collecting information.
Figure 35B:
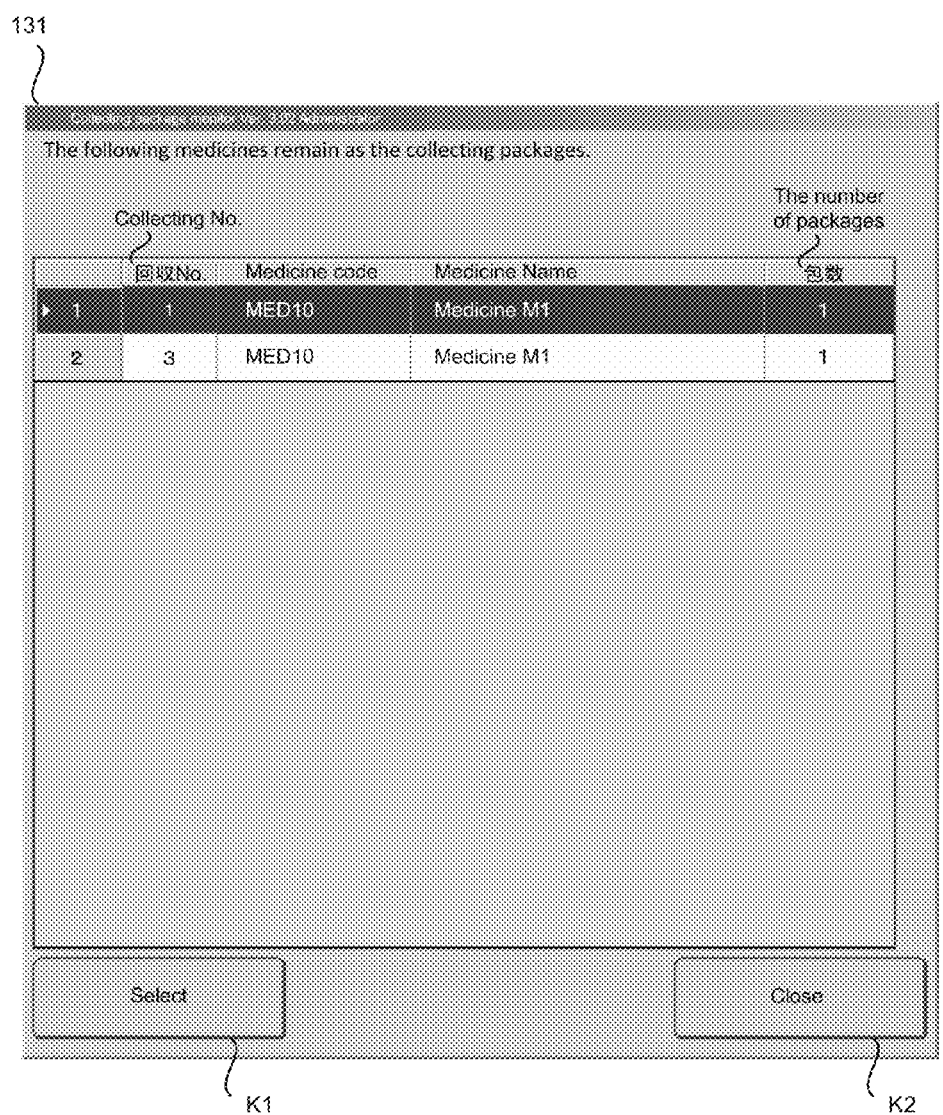

Each of FIGS. 35(A) and 35(B) is a view showing one example of the collecting package monitor screen 131. Specifically, in the collecting package monitor screen 131 shown in FIG. 35(A), the medicine code, the medicine name of the remaining medicine and the number of the collecting packages 521 in which the remaining medicines are contained are displayed for every type of remaining medicines. On this screen, when one of the types of remaining medicines is selected and an operating key K1 is operated, the remaining medicine control portion 114 allows the monitor to display the collecting package monitor screen 131 shown in FIG. 35(B). In the collecting package monitor screen 131 shown in FIG. 35(B), the collecting number of the collecting package 521, the medicine code, the medicine name of the remaining medicine and the number of the collecting packages 521 in which the remaining medicines are contained are displayed for every collecting package 521 in which the same type of remaining medicines are contained.

The remaining medicine control portion 114 closes the collecting package monitor screen 131 in a case where an operating key K2 displayed on the collecting package monitor screen 131 shown in FIGS. 35(A) and 35(B) is operated. In a case where the operating key K1 is operated after one of the collecting packages 521 displayed on the collecting package monitor screen 131 shown in FIG. 35(B) is selected, the remaining medicine control portion 114 allows the monitor 13 to display detailed information related to the selected collecting package 521. For example, the detailed information related to the collecting package 521 contains identification information specified in the prescription data (prescription ID or the like) at the time of collecting the remaining medicines, the patient name of the prescription data, a collecting time of the remaining medicine, the lot number of the remaining medicine and the expiration date of the remaining medicine or the like.

<Step S94>

At a step S94, the remaining medicine control portion 114 determines whether or not the medicine information is allocated to the unspecified cassette 22 in the medicine dispensing process (see FIG. 11). At this time, the remaining medicine control portion 114 shifts the process to a step S95 in a case where the remaining medicine control portion 114 determines that the medicine information is allocated to the unspecified cassette 22 (the case of determining "Yes" at the step S94). On the other hand, the remaining medicine control portion 114 returns the process to the step S91 until the medicine information is allocated to the unspecified cassette 22 (the case of determining "No" at the step S94).

<Step S95>

At the step S95, the remaining medicine control portion 114 determines, on the basis of the collecting information 123 stored in the storage portion 12, whether or not there exists the collecting package 521 in which the same type of medicine as the medicine corresponding to the medicine information allocated to the unspecified cassette 22. In this case, the remaining medicine control portion 114 carrying out this determining process is one example of determining means. The remaining medicine control portion 114 shifts the process to a step S96 in a case where the remaining medicine control portion 114 determines that there exists the collecting package 521 in which the same type of medicine as the medicine corresponding to the medicine information is contained (the case of determining "Yes" at the step S95). On the other hand, the remaining medicine control portion 114 returns the process to the step S91 in a case where the remaining medicine control portion 114 determines that there does not exist the collecting package 521 in which the same type of medicine as the medicine corresponding to the medicine information is contained (the case of determining "No" at the step S95).

<Step S96>

At the step S96, the remaining medicine control portion 114 allows a packaging monitor screen 132, which contains a prescription display portion 1321 on which information specified in the prescription data is displayed, to display a remaining medicine display portion 1322 indicating existence of the collecting package 521 in which the same type of medicine as the medicine corresponding to the medicine information is contained. With this configuration, the user can easily recognize whether or not the medicine in the collecting package 521 can be used at the time of supplying the medicine into the unspecified cassette 22. Namely, in the medicine dispensing apparatus 400, reuse of the medicine in the collecting package 521 at the time of supplying the medicine into the unspecified cassette 22 is assisted. In this regard, the remaining medicine control portion 114 carrying out this display process for displaying the remaining medicine display portion 1322 is also one example of collecting information display means.

Figure 36:
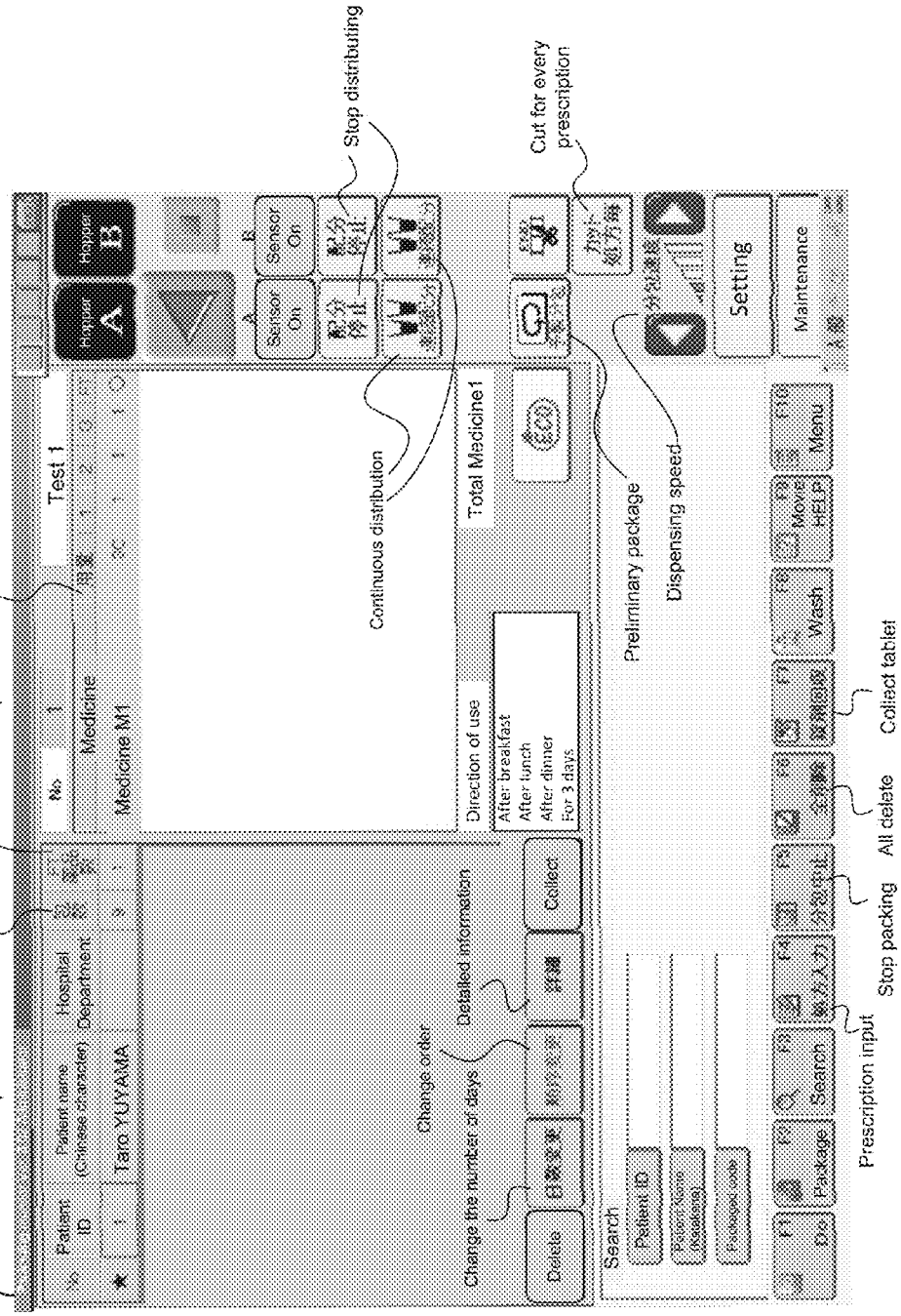
FIG. 36 is a view showing a display example of the collecting information.

FIG. 36 is a view showing one example of the packaging monitor screen 132. In the prescription display portion 1321, information such as a patient ID, a patient name, a hospital department, the number of packages and the number of medicines to be contained in the unspecified cassettes 22 (FT medicine number) is displayed as contents of the issued prescription data of the medicine to be packaged. Further, on the remaining medicine display portion 1322, the medicine information corresponding to the same type of medicine as the collecting package 521, which has not yet been used, among the medicine information contained in the prescription data is displayed. In a case where a plurality of medicine information corresponding to the same type of medicine as the collecting package 521, which has not yet been used, are contained in the prescription data, the plurality of medicine information are displayed on the remaining medicine display portion 1322.

<Step S97>

At a step S97, the remaining medicine control portion 114 allows the monitor 13 to display a use confirmation screen 133 for allowing the user to select whether or not the collecting package 521, which has not yet been used, should be used for the medicine information corresponding to the same type of collecting package 521 which has not yet been used among the medicine information allocated to the unspecified cassette 22. For example, the use confirmation screen 133 is displayed as a pop-up screen while the packaging monitor screen 132 is displayed. In this regard, it is possible to take another embodiment in which the use confirmation screen 133 is displayed in a case where a selecting operation for the medicine information displayed on the remaining medicine display portion 133 is carried out. Further, in a case where a plurality of collecting packages 521 exist, the remaining medicine control portion 114 may allow the monitor 13 to display the same collecting package selecting screen as the collecting package monitor screen 131 (see FIG. 35(B)) to allow the user to select one of the collecting packages 521.

Figure 37A:
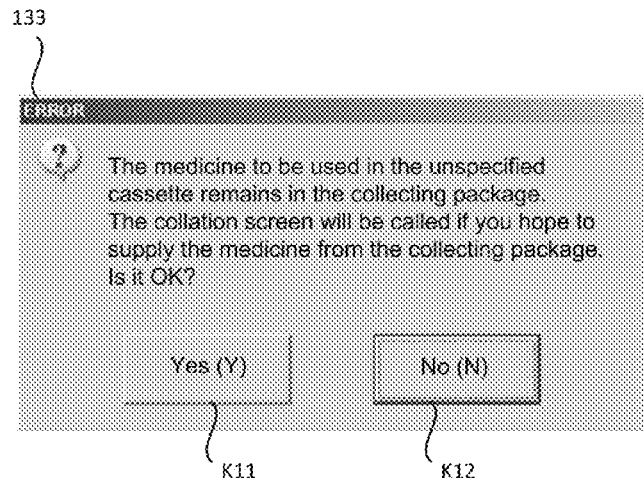
FIG. 37 is a view showing display examples of a use confirmation screen and a collation screen.

FIG. 37(A) is a view showing one example of the use confirmation screen 133. On the use confirmation screen 133 shown in FIG. 37(A), a message indicating that the medicine which should be used for the unspecified cassette 22 remains in the collecting package 521 and a message indicating for requiring an answer for determining whether or not the collecting package 521 should be used are displayed. Further, on the use confirmation screen 133, an operating key K11 and an operating key K12 for selecting whether or not the collecting package 521 should be used are displayed.

<Step S98>

At a step S98, the remaining medicine control portion 114 branches the process depending on an answering operation which is carried out by the user for determining whether or not the collecting package 521 should be used. Specifically, the remaining medicine control portion 114 shifts the process to a step S99 in a case where the remaining medicine control portion 114 determines that it is selected by operating the operating key K11 that the collecting package 521 should be used (the case of determining "Yes" at the step S98). On the other hand, the remaining medicine control portion 114 returns the process to the step S91 in a case where the remaining medicine control portion 114 determines that it is selected by operating the operating key K12 that the collecting package 521 should not be used (the case of determining "No" at the step S98).

Figure 37B:
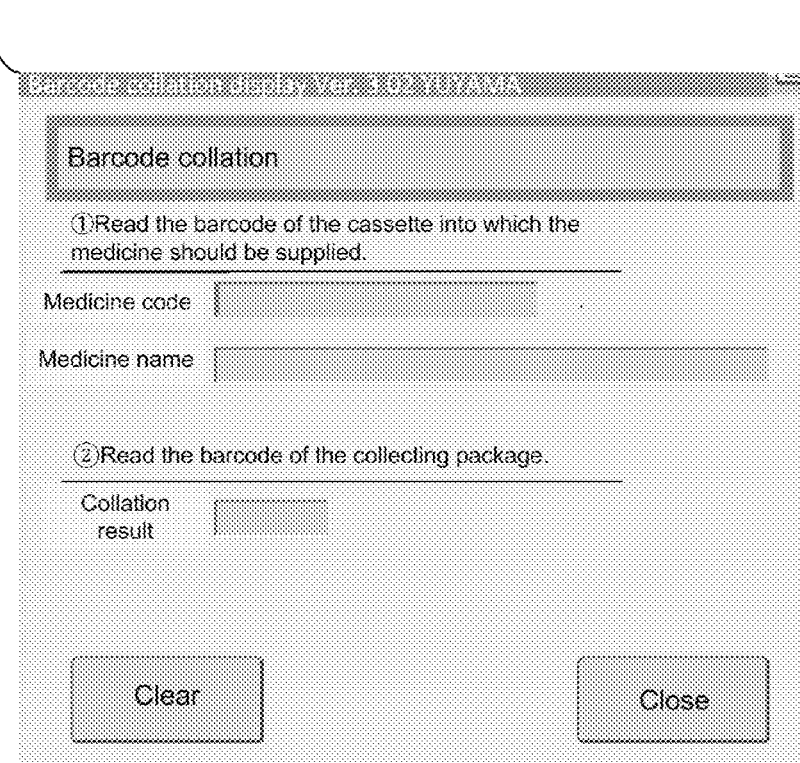

At the step S99, the remaining medicine control portion 114 allows the monitor 13 to display a collation screen 134 for assisting a collation work of the collecting package 521. FIG. 37(B) is a view showing one example of the collation screen 134. On the collation screen shown in FIG. 37(B), a procedure for collating the collecting package 521 is displayed. Specifically, on the collation screen 134, a message indicating that it is necessary to first read the barcode displayed on the display portion 25 of the unspecified cassette 22 and then read the barcode printed on the collecting package 521. With this configuration, the user allows the barcode reader 7 to read the barcode displayed on the display portion 25 and the barcode printed on the collecting package 521 in turn.

<Step S100>

At a step S100, the remaining medicine control portion 114 waits for reading of information from the barcode of the unspecified cassette 22 by means of the barcode reader 7 (the case of determining "No" at the step S100). On the other hand, the remaining medicine control portion 114 shifts the process to a step S101 in a case where the remaining medicine control portion 114 determines that the information from the barcode is read by the barcode reader 7 (the case of determining "Yes" at the step S100).

<Step S101>

At the step S101, the remaining medicine control portion 114 allows display columns for a medicine code and a medicine name in the collation screen 134 to display a medicine code and a medicine name specified based on the information obtained from the barcode of the unspecified cassette 22.

<Step S102>

At a step S102, the remaining medicine control portion 114 waits for the reading of the information from the barcode of the collecting package 521 by means of the barcode reader 7 (the case of determining "No" at the step S102). On the other hand, the remaining medicine control portion 114 shifts the process to a step S103 in a case where the remaining medicine control portion 114 determines that the information from the barcode of the collecting package 521 is read by the barcode reader 7 (the case of determining "Yes" at the step S102).

<Step S103>

At the step S103, the remaining medicine control portion 114 collates whether or not the medicine information indicated by the barcode read at the step S100 matches the medicine information indicated by the barcode read at the step S102. In this case, the remaining medicine control portion 114 carrying out this collating process is one example of collating means. The remaining medicine control portion 114 may determine whether or not the two medicine information obtained from the two barcodes read by the barcode reader 7 in no particular order match with each other.

The information indicated by the barcode displayed on the display portion 25 and the information indicated by the barcode printed on the collecting package 521 may contain information for identifying each of the information. In this case, the remaining medicine control portion 114 can determine that the barcode read by the barcode reader 7 is obtained from the display portion 25 or the collecting package 521. For example, the remaining medicine control portion 114 may allow the monitor 13 to display an error message in a case where the barcode printed on the collecting package 521 is first read by the barcode reader 7.

Further, at the step S103, the remaining medicine control portion 114 may confirm that the collecting number contained in the barcode read at the step S102 is stored in the collecting information 123, that is, may confirm that the collecting package 521 corresponding to the collecting number has not yet been used. Furthermore, the remaining medicine control portion 114 may confirm that the collecting package 521 can be used at present on the basis of information such as the lot number and the expiration date of the medicine contained in the collecting package 521 corresponding to the collecting number. Furthermore, in a case where the collecting package 521 has been already used, the remaining medicine control portion 114 may allow the monitor 13 to display a message indicating that the collecting package 521 has been already used to report the user it.

<Step S104>

At a step S104, the remaining medicine control portion 114 branches the process depending on the collation result at the step S103. Specifically, the remaining medicine control portion 114 shifts the process to a step S105 in a case where the collation result is "Matched" (the case of determining "Yes" at the step S104). On the other hand, the remaining medicine control portion 114 returns the process to the step S97 after the remaining medicine control portion 114 allows the display column for the collation result in the collation screen 134 to display a message "NG" in a case where the collation result is "Not matched" (the case of determining "No" at the step S104).

<Step S105>

At the step S105, the remaining medicine control portion 114 allows the display column for the collation result in the collation screen 134 to display a message "OK" or the like to report the user that the collecting package 521 can be used. Then, the user supplies the medicine contained in the collecting package 521 into the unspecified cassette 22. Thus, it is possible to prevent an incorrect medicine from being supplied into the unspecified cassette 22.

<Step S106>

At a step S106, the remaining medicine control portion 114 deletes the information on the collecting package 521 corresponding to the barcode read at the step S102 from the collecting information 123 in the storage portion 12. As a result, only the information on the collecting package 521, which has not yet been used, remains in the collecting information 123.

For example, in a case where the collecting information 123 and the barcode on the collecting package 521 do not contain the information such as the collecting number for identifying each of the collecting packages 521, the remaining medicine control portion 114 may reduce the number of the collecting packages 521, in which the medicines corresponding to the barcodes read at the step S102 are respectively contained, by one. Further, at the step S92, the remaining medicine control portion 114 adds the value stored in the collecting information 123 as the number of the collecting packages 521 corresponding to the same type of medicine on the basis of the remaining medicine information. By using such a simple management method, it is also possible to achieve the remaining medicine reuse function.

In a case where the barcode on the collecting package 521 contains the identification information such as the collecting number of the collecting package 521 for identifying the collecting package 521, the remaining medicine control portion 114 can delete the information on the collecting package 521 identified based on the identification information from the collecting information 123 at the step S106. Further, the remaining medicine control portion 114 may store the information on the collecting package 521 as a log record together with a use time, the prescription data of a use object or the like after the collecting package 521 is used.

As described above, in the medicine dispensing apparatus 400, by using the remaining medicine reuse function, it is possible to assist the reuse of the medicine of the collecting package 521 which is collected in the remaining medicine collecting process at the time of the dispensation of the medicine of the prescription data which was issued in the past. Thus, for example, it is possible to prevent waste of the medicine of the collecting package 521 and reduce a user work for putting the medicine of the collecting package 521 back to the medicine container (such as the medicine box and the medicine bottle) placed on the medicine shelf.

The application of the remaining medicine reuse function is not limited to the case of carrying out the medicine dispensing process (see FIG. 11) for allocating the medicine information to one of the unspecified cassettes 22 due to the issuing of the prescription data (this process is described in the description for the first embodiment). For example, the remaining medicine reuse function can be applied to the case where the medicine information is allocated to one of the unspecified cassettes 22 before the issuing of the prescription data as the second embodiment and the third embodiment.

Further, the medicine dispensing apparatus 400 may output the collecting package 521 for the unspecified cassette 22 from which the remaining medicine is not dispensed in the remaining medicine collecting process among the unspecified cassettes 22 to which the medicine information specified in the prescription data is allocated. However, the medicine dispensing apparatus 400 can print the information on the collecting package 521 by means of the printer 53 before the medicine is contained into the collecting package 521 after the medicine is dispensed from the unspecified cassette 22. Thus, the control portion 61 may omit the output of the collecting package 521 corresponding to the unspecified cassette 22 from which the remaining medicine is not dispensed in the remaining medicine collecting process. With this configuration, it is possible to prevent waste of the collecting package 521.

On the other hand, the medicine dispensing apparatus 400 may take a configuration in which it is prohibited to print the information on the collecting package 521 by means of the printer 53 before the medicine is contained into the collecting package 521 after the medicine is dispensed from the unspecified cassette 22. In this case, since the number of the medicine to be dispensed from the unspecified cassette 22 is unknown at the time of printing the information by means of the printer 53, the control portion 61 omits the printing of the information, on the collecting package 521, related to the collected amount. In such a configuration, since it is unknown that whether or not the remaining medicine is dispensed form the unspecified cassette 22 at the time of printing the information by means of the printer 53, the same number of the collecting packages 521 as the number of the unspecified cassettes 22 to which the medicine information specified in the prescription data is respectively allocated to are always added to the charta sheet 51. Namely, in a case where the medicine does not remain in the unspecified cassette 22, the collecting package 521 corresponding to the unspecified cassette 22 is outputted as an empty package.

Further, in the medicine dispensing apparatus 400, the control portion 61 allows the packaging unit 5 to collectively package the medicines respectively contained in the unspecified cassettes 22 into one sheet of the packaging paper 52 in the remaining medicine collecting process. A setting related to contents of the remaining medicine collecting process is set by the control portion 11 depending on a user operation performed on the operating portion 14. For example, the control portion 11 can select a method for separately packaging the medicines respectively contained in the unspecified cassettes 22 into different sheets of the packaging paper 52 and a method for collectively packaging the medicines contained in the unspecified cassettes 22 into one sheet of the packaging paper 52 as the contents of the remaining medicine collecting process depending on the user operation performed on the operating portion 14.

FIG. 32(B) is a view showing one example of the charta sheet 51 in the case where the remaining medicines collected from one or more of the unspecified cassettes 22 used for one prescription data are collectively contained into one sheet of the collecting package 523. As shown in FIG. 32(B), on the collecting package 521, only a character string "Collecting package" indicating that the remaining medicines collected from the unspecified cassettes 22 are contained in one collecting package 521 is printed. Namely, on the collecting package 253, the other information such as the medicine name of each of the medicines, the JAN code and the collected amount is not printed. In such a configuration in which the remaining medicines collected from the unspecified cassettes 22 used for one prescription data are always collected into one collecting package 253, a usage amount of the collecting packages 253 is suppressed.

[Another Example of the Remaining Medicine Control Process]

In the remaining medicine control process (see FIG. 33), the remaining medicine control portion 114 may manage the number of the remaining medicines respectively contained in the collecting packages 521. In this case, the control portion 61 transmits the number of the medicines respectively contained in the collecting packages 521 to the control portion 11 as the remaining medicine information in addition to the medicine names, the medicine codes of the medicines respectively dispensed from the unspecified cassettes 22 and the number of the collecting packages 521. Further, the control portion 61 obtains the information on the number of the remaining medicines from the counter for counting the tablets dispensed from each of the unspecified cassettes 22. Hereinafter, description will be given to another example of the remaining medicine control process in which the remaining medicines respectively contained in the collecting packages 521 are managed in units of tablets. In the description for the other example of the remaining medicine control process, the same processes in the remaining medicine control process as the processes used for the case where the remaining medicine respectively contained in the collecting packages 521 are managed in the units of packages are omitted.

<Step S92>

At the step S92, the remaining medicine control portion 114 stores the remaining medicine information in the storage portion 12 as the collecting information 123 related to the medicine collected in the remaining medicine collecting process. At this time, the medicine names, the medicine codes of the medicines dispensed from the unspecified cassettes 22, the number of the collecting packages 521 and the information on the number of the remaining medicines respectively contained in the collecting packages 521 are contained in the collecting information 123. FIG. 34(B) is a view showing another example of the collecting information 123. In the collecting information 123 shown in FIG. 34(B), the collecting number of each of the collecting packages 521 which has not yet been used, the medicine names and the medicine codes of the remaining medicines respectively contained in the collecting packages 521 as well as the number of the remaining medicines respectively contained in the collecting packages 521 are contained. With this configuration, the remaining medicine control portion 114 determines, on the basis of the collecting information 123, the total numbers of the remaining medicines contained in each of the collecting packages 521, the number of the collecting packages 521 and whether or not the collecting packages 521 exist for every types of medicines respectively contained in the collecting packages 521.

<Step S93>

Figure 38A:
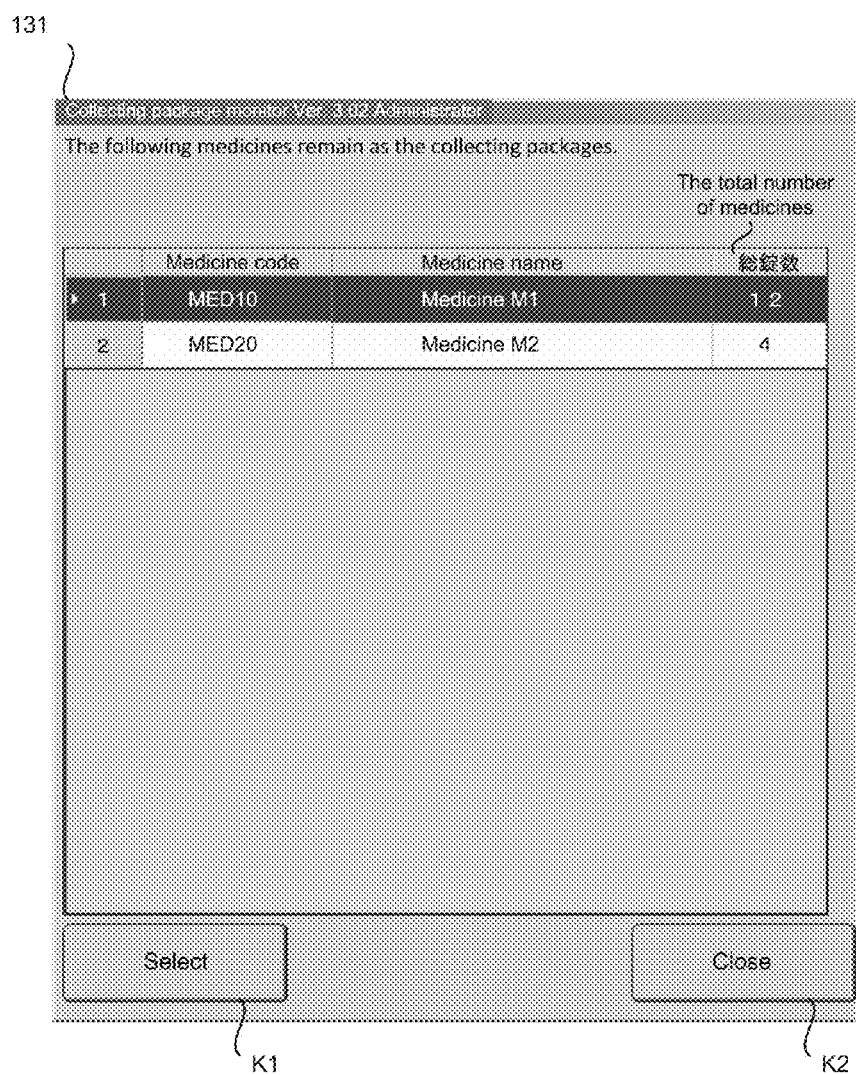
FIG. 38 is a view showing a display example of the collecting information.
Figure 38B:
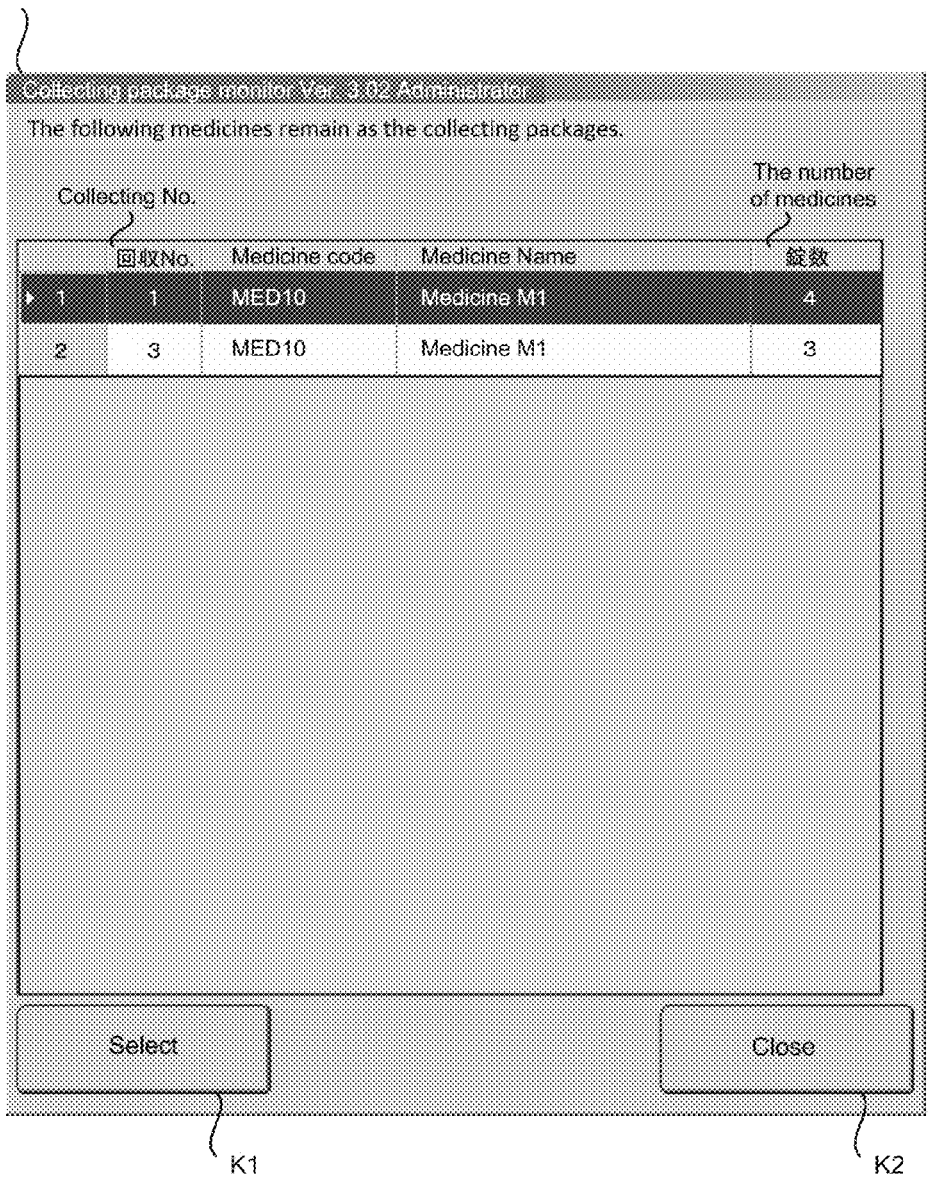

Next, at the step S93, the remaining medicine control portion 114 allows the collecting package monitor screen 131 to display the medicine codes, the medicine names of the remaining medicines and the total numbers of the remaining medicines contained in each of the collecting packages 521 as information on the collecting packages 521 which have not yet been used on the basis of the collecting information 123. Each of FIGS. 38(A) and 38(B) is a view showing other examples of the collecting package monitor screen 131. Specifically, in the collecting package monitor screen 131 shown in FIG. 38(A), for every same types of medicines, the medicine codes, the medicine names of the remaining medicines and the total number of the remaining medicines contained in each of the collecting packages 521 are displayed. At this time, when the operating key K1 is operated after one of the remaining medicines is selected, the remaining medicine control portion 114 allows the collecting package monitor screen 131 shown in FIG. 38(B) to be displayed. In the collecting package monitor screen 131 shown in FIG. 38(B), for every collecting packages 521 in which the same type of remaining medicine is contained, the collecting numbers of the collecting packages 521, the medicine codes, the medicine names of the remaining medicines and the numbers of the remaining medicines contained in the collecting packages 521 are displayed.

<Step S95>

At the step S95, the remaining medicine control portion 114 may determine, on the basis of a predetermined use condition of the collecting package 521, whether or not the collecting package 521 can be used. For example, in the medicine dispensing apparatus 400, the following first use condition, the second use condition and the third use condition may be selected as the use condition. The remaining medicine control portion 114 selects the use condition depending on a user operation performed on the operating portion 14 at the time of the initial setting of the medicine dispensing apparatus 400 or the operation setting for every issuing of the prescription data.

<First Use Condition>

First, as the first use condition, it is possible to determine whether or not there exists at least one collecting package 521 in which the same type of medicine as the medicine corresponding to the medicine information allocated to the unspecified cassette 22 is contained.

For example, at the step S95, the remaining medicine control portion 114 determines that the collecting package 521 cannot be used in a case where there does not exist the collecting package 521 in which a tablet having a medicine name "Medicine M2" allocated to the unspecified cassette 22 is contained. On the other hand, at the step S95, the remaining medicine control portion 114 determines that the collecting package 521 can be used (the case of determining "Yes" at the step S95) to allow the monitor 13 to display the use confirmation screen 133 in a case where there exists at least one collecting package 521, in which the tablet having the medicine name "Medicine M2" allocated to the unspecified cassette 22 is contained. Namely, in a case where there exists at least one collecting package 521 in which the medicine corresponding to the medicine information allocated to the unspecified cassette 22 is contained. The remaining medicine control portion 114 determines that the collecting package 521 can be used regardless of whether or not the numbers of the medicines contained in the collecting package 521 reaches a required amount to be dispensed.

Figure 39A:
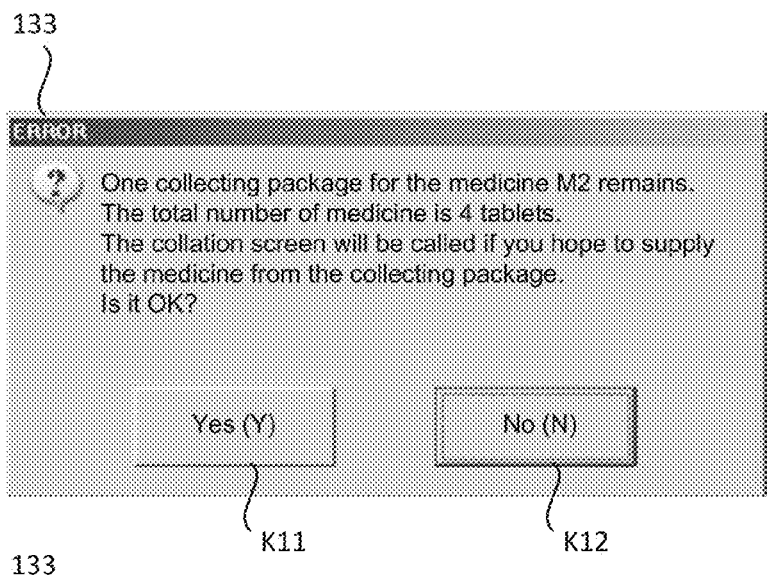
FIG. 39 is a view showing other display examples of the use confirmation screen and the collation screen.

FIG. 39(A) is a view showing one example of the use confirmation screen 133 displayed in the case of using the first use condition. In FIG. 39(A), a message indicating that the medicine used for the unspecified cassette 22 remains as the collecting package 521 and a message requiring an answer for determining whether or not the collecting package 521 should be used are displayed on the use confirmation screen 133. The messages contain the number of the collecting packages 521 (1 package) which can be used for the unspecified cassette 22 and the total number of the medicines (4 tablets) contained in each of the collecting packages 521. As described above, in the case of using the first use condition, it is possible to urge the user to use the collecting package 521 as much as possible, and thereby preventing the collecting package 521 from being preserved in the long term.

<Second Use Condition>

As the second use condition, in addition to the first use condition, it is possible to determine whether or not the total number of the medicines contained in each of the collecting packages 521, in which the same type of medicine as the medicine corresponding to the medicine information allocated to the unspecified cassette 22 is contained, reaches the dispensed amount (prescription amount) of the medicine indicated in the prescription data.

For example, at the step S95, the remaining medicine control portion 114 determines that the collecting package 521 cannot be used in a case where the dispensed amount corresponding to the medicine information having the medicine name "Medicine M1" and allocated to the unspecified cassette 22 among the medicine information contained in the prescription data is "9 tablets" and the total number of the medicines having the medicine name "Medicine M1" and contained in each of the collecting packages 521 is "8 tablets."

On the other hand, the remaining medicine control portion 114 determines that the collecting package 521 can be used at the step S95 and allows the monitor 13 to display the use confirmation screen 133 at the step S96 in a case where the dispensed amount corresponding to the medicine information having the medicine name "Medicine M1" and allocated to the unspecified cassette 22 among the medicine information contained in the prescription data is "9 tablets" and the total number of the medicines contained in each of the collecting packages 521 is "12 tablets." Namely, on condition that the collecting package 521 in which the medicine corresponding to the medicine information allocated to the unspecified cassette 22 exists and the number of the medicines contained in the collecting package 521 reaches a required dispensed amount, the remaining medicine control portion 114 determines that the collecting package 521 can be used.

Figure 39B:
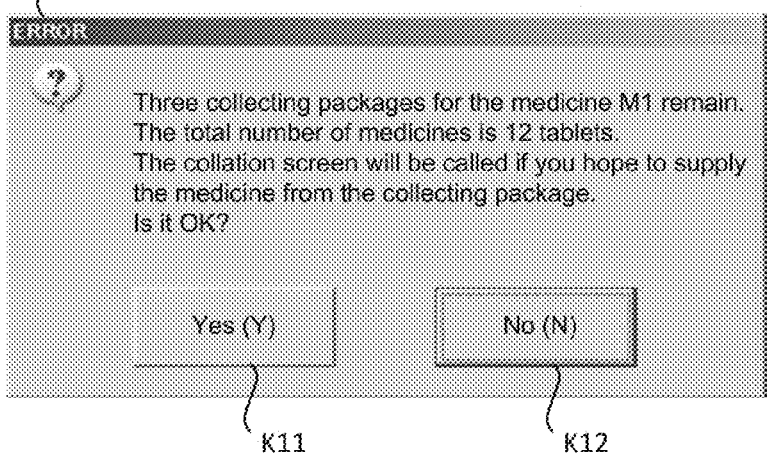

FIG. 39(B) is a view showing one example of the use confirmation screen 133 displayed in the case of using the second use condition. In FIG. 39(B), a message indicating that the medicine used for the unspecified cassette 22 remains in the collecting package 521 and a message requiring an answer for determining whether or not the collecting package 521 should be used are displayed on the use confirmation screen 133. The messages contain the number of the collecting packages 521 (3 packages) which can be used for the unspecified cassette 22 and the total number of the medicines (12 tablets) contained in each of the collecting packages 521.

As described above, in the case of using the second use condition, only in a case where the total number of the medicines reaches the dispensed amount to be supplied into the unspecified cassette 22 by using one or more of the collecting packages 521, a message indicating that the collecting package 521 can be used is displayed. Thus, even if the collecting package 521 is used, in a case where it is necessary to take the medicine to be supplied into the unspecified cassette 22 from the medicine shelf or the like, the use of the collecting package 521 is not urged. Only in a case where it is unnecessary to take the medicine to be supplied into the unspecified cassette 22 from the medicine shelf or the like as an additional procedure, the use of the collecting package 521 is urged.

<Third Use Condition>

As the third use condition, in addition to the first condition, it is possible to determine whether or not the total amount of the medicines contained in each of the collecting packages 521, in which the same type of medicine as the medicine corresponding the medicine information allocated to the unspecified cassette 22 is contained, matches the dispensed amount (prescription amount) of the medicine indicated in the prescription data.

For example, the remaining medicine control portion 114 determines that the collecting package 521 cannot be used at the step S95 in a case where the dispensed amount corresponding to the medicine information having the medicine name "Medicine M1" and allocated to the unspecified cassette 22 among the medicine information contained in the prescription data is "9 tablets" and the total amount of the medicines at the time of combining one or more of the collecting packages 521 among one or more of the collecting packages 521 in which the same type of medicine is contained is not "9 tablets" (less than 9 tablets or equal to or more than 10 tablets).

On the other hand, the remaining medicine control portion 114 determines that the collecting package 521 can be used at the step S95 and allows the monitor 13 to display the use confirmation screen 133 at the step S96 in a case where the dispensed amount corresponding to the medicine information having the medicine name "Medicine M1" and allocated to the unspecified cassette 22 among the medicine information contained in the prescription data is "9 tablets" and the total amount of the medicines at the time of combining one or more of the collecting packages 521 among one or more of the collecting packages 521 in which the same type of medicine is contained is "9 tablets." Namely, on condition that the collecting package 521 in which the medicine corresponding to the medicine information allocated to the unspecified cassette 22 is contained exists and the total amount of the medicines contained in one or more of the collecting packages 521 matches a required dispensed amount, the remaining medicine control portion 114 determines that the collecting package 521 can be used.

Figure 39C:
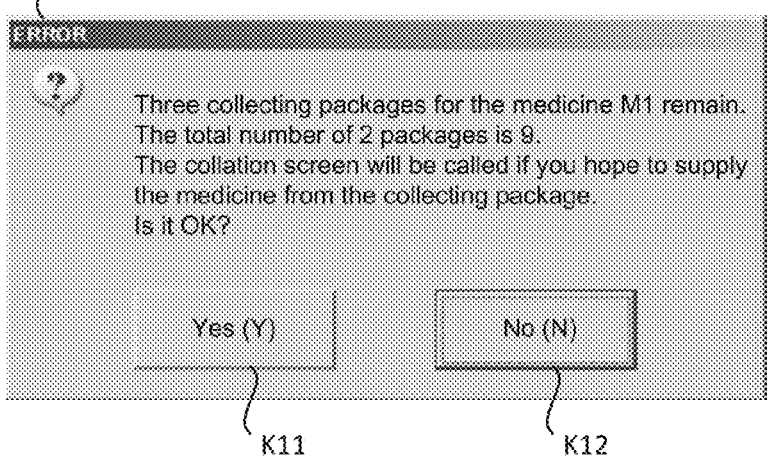
Figure 39D:
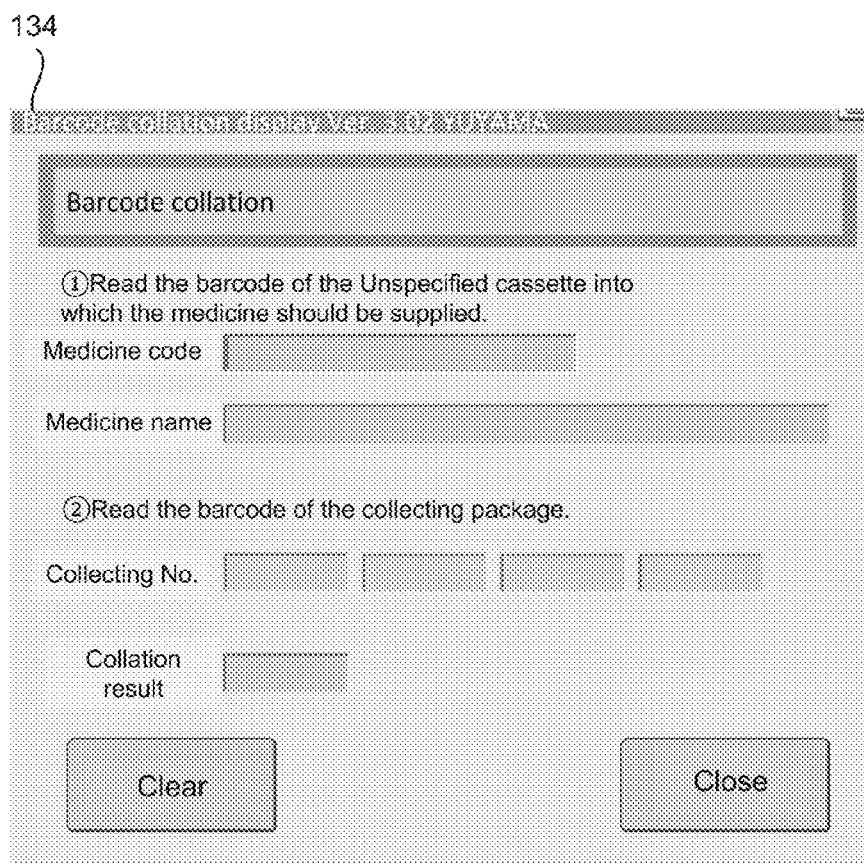

FIG. 39(C) is a view showing one example of the use confirmation screen 133 displayed in the case of using the third use condition. In FIG. 39(C), a message indicating that the medicine used for the unspecified cassette 22 remains as the collecting package 521 and a message requiring an answer for determining whether or not the collecting package 521 should be used are displayed on the use confirmation screen 133. The messages contain the number of the collecting packages 521 (3 packages), a combination number of the collecting packages 521 (2 packages) and the total number of the medicines (9 tablets).

As described above, in the case of using the third use condition, only in a case where the number of the medicines contained in one collecting package 521 or the total number of the medicines contained in the plurality of collecting packages 521 matches the dispensed amount to be supplied into the unspecified cassette 22, a message indicating that the collecting package 521 can be used is reported. With this configuration, in a case where remaining medicines exist after one or more of the collecting packages 521 are used, the use of the collecting package 521 is not urged. Only in a case where the medicines (tablets) contained in one or more of the collecting packages 521 can be used completely, the use of the collecting package 521 is urged.

Fifth Embodiment

The description has been already given to the configuration in which it is possible to automatically package the remaining medicines in the unspecified cassette 22 into the packaging paper by means of the packaging unit and collect the remaining medicines in the remaining medicine collecting process. It is thought that a setting for determining whether or not such a remaining medicine collecting process should be carried out is set as an initial setting in advance. However, since a lot of sheets of the packaging paper are required in a case where the number of the medicines (tablets) remaining in the unspecified cassette 22 is large, there is a case where it is not preferable to automatically package the tablets into the sheets of the packaging paper. Hereinafter, a configuration in which it is possible to arbitrarily switch ON/OFF of the remaining medicine collecting process for packaging the tablets in the unspecified cassette 22 into the sheet of the packaging paper to collect the tablets will be described as the fifth embodiment.

The tablets to be supplied into the unspecified cassette 22 are taken by the user from a separate packaging case such as a PTP sheet in which a plurality of tablets are separately packaged or a multiplex packaging case such as a medicine bottle in which a plurality of tablets are not separately contained but collectively contained. In a case where the tablets to be supplied into the unspecified cassette 22 are contained in the separate packaging cases, there is high possibility that the tablets only in an amount required for the dispensation in this time are taken from the separate packaging cases and supplied into the unspecified cassette 22. Thus, even if the user supplies the tablets into the unspecified cassette 22 more than a necessary amount by mistake, the number of extra tablets remaining in the unspecified cassette 22 would be small (for example, 1 tablet or 2 tablets). In this case, it is possible to package the remaining medicine in the unspecified cassette 22 into one sheet of the packaging paper to collect the remaining medicine.

On the other hand, in a case where the tablet to be supplied into the unspecified cassette 22 is contained in the multiplex packaging case, it is possible to reduce a use work by collectively supplying the plurality of tablets from the multiplex packaging case into the unspecified cassette 22 without counting the number of the tablets required for the dispensation. However, in this case, there is high possibility that the number of the tablets remaining in the unspecified cassette 22 is large after the tablets are dispensed from the unspecified cassette in a required amount. Thus, a lot of sheets of the packaging paper are required for packaging the tablets remaining in the unspecified cassette 22 into the packaging paper to collect the tablets. Further, in a case where an upper limit of the number of the sheets of the packaging paper which can be used for one remaining medicine collecting process is determined, the sheets of the packaging paper cannot be consumed over the upper limit. However, since both a collecting work using the packaging paper and a collecting work for manually collecting the tablets from the unspecified cassette 22 by the user are carried out together, work efficiency deteriorates.

Thus, in the medicine master stored in the storage portion 12, information related to whether each medicine is a tablet contained in the separate packaging case or the multiplex packaging case may be stored. In this regards, the tablet contained in the multiplex packaging case is referred to as "unstuck tablet." The control portion 11 determines, on the basis of the medicine information allocated to the unspecified cassette 22 and the medicine master, whether the tablet to be supplied into the unspecified cassette 22 is the medicine supplied from the separate packaging case or the multiplex packaging case.

The control portion 11 allows the remaining medicine collecting process for the unspecified cassette 22 to be carried out in a case where the control portion 11 determines that the tablets allocated to the unspecified cassette 22 are the medicine supplied from the separate packaging case. Specifically, the control portion 11 transmits the carrying out request for the remaining medicine collecting process to the control portion 61 at the step S10 (see FIG. 11). With this configuration, the tablet contained in the unspecified cassette 22 is collected by using the packaging paper. At this time, since there is high possibility that the number of the tablets remaining in the unspecified cassette 22 is small, it is possible to collect the remaining tablets (medicines) by one sheet of the packaging paper.

On the other hand, the control portion 11 does not allow the remaining medicine collecting process for the unspecified cassette 22 to be carried out in a case where the tablet allocated to the unspecified cassette 22 is the medicine supplied from the multiplex packaging case. Specifically, the control portion 11 does not transmit the carrying out request for the remaining medicine collecting process to the control portion 61 at the step S10 (see FIG. 11). Since the tablets in the unspecified cassette 22 are not collected by the packaging paper in such a case where there is high possibility that the number of the tablets remaining in the unspecified cassette 22 is large, it is possible to suppress waste of the packaging paper or waste of runtime of the remaining medicine collecting process. In this case, the user manually collects the tablets from the unspecified cassette 22.

As described above, the control portion 11 switches ON/OFF of the remaining medicine collecting process depending on whether the tablet allocated to the unspecified cassette 22 is the tablet supplied from the separate packaging case or the multiplex packaging case. In this case, the control portion 11 carrying out such a process is one example of collection switching means. In a case where the remaining medicine collecting process for the unspecified cassette 22 is not carried out, the control portion 11 may allow the display portion 25 provided at the unspecified cassette 22 to display information indicating that it is necessary to confirm and collect the remaining medicine in the unspecified cassette 22.

Further, a method for determining whether the tablet to be supplied into the unspecified cassette 22 is contained in the separate packaging case or the multiplex packaging case is not limited to the method based on the medicine master. For example, as described above, there is a case where the identification information such as the JAN code written on the medicine container (case) or the PTP sheet in which the tablets are separately contained is read by means of the barcode reader 7 at the time of supplying the tablet into the unspecified cassette 22. In this case, the identification information may contain information indicating whether the case in which the tablet is contained is the separate packaging case or the multiplex packaging case. Thus, the control portion 11 determines, on the basis of the identification information, whether the tablet to be supplied into the unspecified cassette 22 is contained in the separate packaging case or the multiplex packaging case to determine whether or not the remaining medicine collecting process should be carried out.

In this regards, the control portion 61 of the packaging control unit 6 may determine whether or not the remaining medicine collecting process should be carried out. In this case, the control portion 61 is one example of collection switching means. For example, the control portion 61 may switch ON/OFF of the remaining medicine collecting process depending on whether the tablet allocated to the unspecified cassette 22 is the tablet contained in the separate packaging case or the multiplex packaging case in a case where the control portion 61 receives the carrying out request for the remaining medicine collecting process at the step S16.

Summary of Embodiments

A medicine dispensing apparatus according to the present invention includes a plurality of medicine cassettes, allocating means and driving control means. The medicine cassettes can respectively dispense desired types of medicines. The allocating means allocates medicine information to one of the medicine cassettes when the medicine information is given. The driving control means drives the medicine cassette according to a predetermined driving condition corresponding to the medicine information allocated to the medicine cassette by the allocating means to dispense the medicine from the medicine cassette. For example, the medicine is a tablet.

According to the present invention, since it is sufficient for the user only has to supply a desired type of tablet to be dispensed into the medicine cassette for dispensing the tablet, it is possible to reduce a user work compared with a conventional art in which the tablet is supplied into each of boxes of the manual packaging unit. Further, prescription errors caused due to human errors are prevented because it is unnecessary to supply the tablet into each of the boxes.

For example, the medicine dispensing apparatus may include driving means for supplying driving force to a driving mechanism provided at the medicine cassette and the driving control means may control the driving means according to the driving condition to drive the medicine cassette.

The allocating means may allocate the medicine information to one of the medicine cassettes when the medicine information on the medicine to be dispensed is specified in prescription data. Further, the medicine dispensing apparatus may further include code reading means for reading the medicine information from a one-dimensional code or a two-dimensional code and the allocating means may allocate the medicine information to one of the medicine cassettes when the medicine information on the medicine to be dispensed is given through the code reading means.

Further, it is possible to take another configuration in which the medicine dispensing apparatus further includes a plurality of specified medicine cassettes for respectively dispensing predetermined specified types of medicines. In this case, the allocating means allocates the medicine information to one of the medicine cassettes when the medicine dispensing apparatus does not have any specified medicine cassette corresponding to the medicine information on the medicine to be dispensed. With this configuration, it is possible to prevent a waste work of the user for supplying the medicine into the medicine cassette in a case where the medicine indicated in the medicine information on the medicine to be dispensed is contained in the specified medicine cassette.

Further, it is possible to take a configuration in which the medicine dispensing apparatus further includes a manual distributing portion on which there are provided a plurality of boxes into which medicines to be packaged are to be respectively supplied in units of packages; and a manual dispensing portion for selectively dispensing the medicine contained in each of the boxes. In this case, the allocating means may display a message indicating that the manual distributing portion should be used without carrying out the allocation of the medicine information to one of the medicine cassettes when the medicine information on the medicine to be dispensed matches predetermined allocation exclusion medicine information. Further, the allocating means may display a message indicating that the manual distributing portion should be used without carrying out the allocation of the medicine information to one of the medicine cassettes when the medicine information on the medicine to be dispensed matches predetermined allocation exclusion medicine information regardless of whether or not the medicine dispensing apparatus has any specified medicine cassette corresponding to the medicine information on the medicine to be dispensed.

The medicine dispensing apparatus may further include driving correspondence information storage means for storing driving correspondence information indicating a correspondence relationship between the medicine information and the driving condition and the driving control means may identify, on the basis of the driving correspondence information, the driving condition corresponding to the medicine information on the medicine to be dispensed.

Further, the medicine dispensing apparatus may include allocation information storage means for storing allocation information indicating an allocation state associated with the medicine cassette and the medicine information and the allocating means may allocate, on the basis of the allocation information, the medicine information on the medicine to be dispensed to one of the medicine cassettes which has not yet been subjected to the allocation.

For example, the driving condition includes at least one of a prior driving condition related to adjustment of the medicine cassette before a start of a dispensation of the medicine from the medicine cassette, an under-driving condition related to driving control during the dispensation of the medicine from the medicine cassette and a driving stop condition related to driving control to be performed when the dispensation of the medicine from the medicine cassette is stopped.

The medicine cassette may have dispensing means for dispensing the medicine from a medicine containing portion in which the medicine is contained and the under-driving condition may include a dispensing speed of the medicine to be dispensed by the dispensing means. With this configuration, it is possible to dispense the tablet with a dispensing speed suitable for each tablet.

Further, the medicine cassette may have path adjusting means for changing one or both of a height and a width of a dispensing path through which the medicine is dispensed from a medicine containing portion in which the medicine is contained and the prior driving condition may include one or both of the height and the width of the dispensing path. With this configuration, it is possible to change the dispensing path to a size for dispensing the tablet one by one to dispense the tablet from the medicine cassette one by one by.

Further, in a configuration in which the medicine cassette has dispensing means for dispensing the medicine by driving a conveying member which conveys the medicine from a medicine containing portion in which the medicine is contained toward a dispensing port, the driving stop condition may include a condition for determining whether or not a reverse rotation operation is carried out at the time of stopping the dispensation of the medicine from the medicine cassette. The reverse rotation operation can switch a conveying direction of the medicine by the dispensing means to a reverse direction. With this configuration, it is possible to carry out the reverse rotation operation in a case where the tablet has a shape which is likely to be rolled and prevent the tablet from being extra dispensed at the time of stopping the dispensation of the tablet.

Further, the medicine dispensing apparatus may include a plurality of medicine displaying means respectively provided at the medicine cassettes or mounting portions of the medicine cassettes so as to respectively correspond to the medicine cassettes; and display control means for allowing the medicine displaying means corresponding to one of the medicine cassettes to display one or both of the medicine information allocated to the medicine cassette and status information indicating a working status of the medicine cassette. With this configuration, in the medicine dispensing apparatus, by using the medicine displaying means, the user can easily recognize one or both of the medicine information allocated to the medicine cassette and the status information indicating the working status of the medicine cassette.

Further, each of the medicine cassettes may be detachably provided at the medicine dispensing apparatus and each of the medicine displaying means may be an electronic paper provided at each of the medicine cassettes. Furthermore, the display control means may allow the electronic paper to display at least the medicine information. With this configuration, since the user can confirm the information on the tablet allocated to the medicine cassette by visually inspecting and confirming the electronic paper even after the medicine cassette is removed from the medicine dispensing apparatus, it is possible to prevent a supplying error of the tablet. Especially, the display control means may allow the electronic paper to display a dispensed amount of the medicine corresponding to the medicine information.

Further, the display control means may allow the electronic paper to display a patient name indicated in prescription data including the medicine information. Furthermore, the display control means may allow the electronic paper to display a message indicating one or both of a shortage of the medicine and a shortage amount of the medicine when the medicine of the medicine cassette is insufficient with respect to an amount of the medicine corresponding to the medicine information indicated in prescription data including the medicine information. Furthermore, the display control means may allow the electronic paper to display at least one of information: a remaining amount; a lot number; and an expiration date of the medicine corresponding to the medicine information. By displaying various information on the electronic paper in this manner, the user can refer to various information regardless of whether the medicine cassette is in a mounting state or a non-mounting state, and thereby improving work efficiency.

Further, the medicine dispensing apparatus may further include remaining medicine collecting means for dispensing the medicine by driving the medicine cassette after the dispensation of the medicine from the medicine cassette by means of the driving control means. With this configuration, it is possible to prevent the medicine from remaining in the medicine cassette.

It is possible to take a configuration in which the medicine dispensing apparatus includes packaging means for packaging the medicine supplied from the medicine cassette into packaging paper in units of predetermined packages. In this case, the remaining medicine collecting means may allow the packaging means to separately package medicines remaining in the medicine cassettes into different sheets of packaging paper in correspondence with the types of the medicines. With this configuration, since the same type of medicine is contained in one sheet of the packaging paper in correspondence with the types of the medicines, the user can easily carry out a work for returning the medicine to a medicine container such as a medicine shelf, for example.

Further, the medicine dispensing apparatus may include printing means for printing information on the packaging paper; and print control means for allowing the printing means to print, on the packaging paper, identification information of the medicines to be packaged into the packaging paper by the remaining medicine collecting means. With this configuration, the use can easily recognize the medicine contained in the packaging paper.

Further, the medicine dispensing apparatus may include counting means for counting the number of the medicine dispensed from the medicine cassette. In this case, the print control means may allow the printing means to print, on the packaging paper, the identification information of the medicines and collected amounts of the medicines counted by the counting means when the remaining medicine collecting means packages the medicines into the packaging paper. With this configuration, the use can easily recognize the collected amounts of the medicines contained in the packaging paper.

Further, the medicine dispensing apparatus may include storage control means for allowing storage means to store collecting information related to the medicines collected by the remaining medicine collecting means, and collecting information displaying means for displaying the collecting information. With this configuration, the use can refer to the collection information to determine whether or not the medicine collected by the remaining medicine collecting means should be used at the time of supplying the medicine into the medicine cassette.

Further, the medicine dispensing apparatus may include determining means for determining on the basis of the collecting information whether or not there is the packaging paper in which the same type of medicine as the medicine corresponding to the medicine information allocated to one of the medicine cassettes is packaged. In this case, the collecting information displaying means may display a message indicating that the packaging paper exists when the determining means determines that there is the packaging paper in which the same type of medicine as the medicine corresponding to the medicine information allocated to one of the medicine cassettes is packaged. With this configuration, the user can easily determine whether or not the medicine collected by the remaining medicine collecting means can be used at the time of supplying the medicine into the medicine cassette. Namely, in the medicine dispensing apparatus, a reuse of the medicine in the packaging paper at the time of supplying the medicine into the medicine cassette is assisted.

Further, the medicine dispensing apparatus may include a plurality of medicine displaying means respectively provided at the medicine cassettes or mounting portions of the medicine cassettes so as to respectively correspond to the medicine cassettes; display control means for allowing the medicine displaying means corresponding to one of the medicine cassettes to display identification information of the medicine corresponding to the medicine information allocated to the medicine cassette; printing means for printing information on the packaging paper; print control means for allowing the printing means to print, on the packaging paper, identification information of the medicines to be packaged into the packaging paper by the remaining medicine collecting means; and collating means for collating the identification information read from both the medicine displaying means and the packaging paper. The identification information of the medicine displayed on the medicine displaying means and the identification information of the medicine printed on the packaging paper may be a one-dimensional code or a two-dimensional code. With this configuration, since the medicine to be supplied into the medicine cassette and the medicine contained in the packaging paper are collated, it is possible to prevent an incorrect medicine from being supplied into the medicine cassette.

In a configuration in which the medicine dispensing apparatus includes packaging means for packaging the medicine supplied from the medicine cassette into a packaging paper in units of predetermined packages, the remaining medicine collecting means may allow the packaging means to collectively package medicines remaining in the medicine cassettes into the packaging paper. With this configuration, it is possible to collectively package some types of medicines into one sheet of the packaging paper to collect the medicines, and thereby suppressing a usage amount of the packaging paper.

Further, the medicine dispensing apparatus may further include collection switching means for switching ON/OFF of an operation for collecting the medicine remaining in one of the medicine cassettes by means of the remaining medicine collecting means depending on from which of a separate packaging case and a collective packaging case the medicine corresponding to the medicine information allocated to the medicine cassette is supplied, wherein the separate packaging case contains each medicine separately, and the collectively packaging case contains medicines collectively. With this configuration, it is possible to arbitrarily suppress a consumption of the packaging paper used at the time of collecting the medicine by means of the remaining medicine collecting means.

The medicine dispensing apparatus may include a plurality of specified medicine cassettes for respectively dispensing predetermined specified types of medicines; a plurality of specified medicine displaying means respectively provided at the specified medicine cassettes or mounting portions of the specified medicine cassettes so as to respectively correspond to the specified medicine cassettes; and specified display control means for allowing the specified medicine displaying means to display at least one of information: identification information; a remaining amount; a lot number; and an expiration date of the specified medicine corresponding to one of the specified medicine cassettes. In this case, the specified medicine displaying means may be an electronic paper. With this configuration, the use can easily confirm the identification information, the remaining amount, the lot number and the expiration date of the specified medicine contained in the specified medicine cassette.

Specifically, in a configuration in which the medicine dispensing apparatus further includes supplied amount receiving means for receiving a supplied amount of the medicine with respect to the specified medicine cassette, the specified display control means may increase the remaining amount of the medicine displayed on the specified medicine displaying means depending on the supplied amount received by the supplied amount receiving means. On the other hand, in a configuration in which the medicine dispensing apparatus further includes specified counting means for counting a dispensed number, which is the number of medicines dispensed from each specified medicine cassette, the specified display control means may reduce the remaining amount of the medicine displayed on the specified medicine displaying means depending on the dispensed number counted by the specified counting means. With this configuration, the remaining amount of the medicine at present is displayed on the specified medicine displaying means.

The present invention can be interpreted as a method of dispensing medicines with a medicine dispensing apparatus including a plurality of medicine cassettes for respectively dispensing desired types of medicines. The method includes allocating medicine information on a medicine to be dispensed to one of the medicine cassettes when the medicine information is given; and driving the medicine cassette according to a driving condition predetermined so as to correspond to the medicine information allocated in the allocating step, to dispense the medicine from the medicine cassette.

Further, the present invention can be interpreted as a medicine dispensing program for allowing a computer to execute a method of dispensing a medicine. The method includes allocating medicine information on a medicine to be dispensed to one of a plurality of medicine cassettes for respectively dispensing desired types of medicines when the medicine information is given; and driving the medicine cassette according to a driving condition predetermined so as to correspond to the medicine information allocated in the allocating step, to dispense the medicine from the medicine cassette.

Further, the present invention can be interpreted as a computer-readable storage medium storing the medicine dispensing program.

According to the present invention, since it is sufficient for the user only has to supply tablets to be dispensed into the medicine cassettes for dispensing desired types of tablets, it is possible to reduce a user work compared with a conventional art in which the tablet is supplied into each of boxes of the manual packaging unit. Further, a prescription error caused by a human error is prevented because it is unnecessary to supply the tablet into each of the boxes.

Further, in a configuration in which the medicine information allocated to the medicine cassette is displayed on the electronic paper provided at the medicine cassette, it is possible to confirm the medicine information even if the medicine cassette is removed from the medicine dispensing apparatus, and thereby preventing a supplying error of the tablet.

DESCRIPTION OF REFERENCE SIGNS

1: Control unit
11: Control portion
111: Packaging control portion
112: Allocating control portion
113: Display control portion
114: Remaining medicine control portion
12: Storage portion
121: Allocation information
122: Driving correspondence information
123: Collecting information
13: Monitor
14: Operating portion
15: Communication IF
2: Tablet supplying unit
21: Specified cassette
211: Mounting portion
22: Unspecified cassette
221: Mounting portion
222: Tablet containing portion
223: First rotating body
224: Second rotating body
225: Dispensing port
226: Height restriction member
226A: Adjusting portion
227: Width restriction member
227A: Adjusting portion
23: Specified driving portion
231: Driving motor
232: RFID reader writer
24: Unspecified driving portion
241: Driving motor
242: Driving motor
243: Driving motor
244: Driving motor
245: RFID reader writer
25: Display portion (electronic paper)
26: RFID tag
27: Status display lamp
291: Display portion
292: Status display lamp
3: Powdered medicine supplying unit
33: Powdered medicine cassette
331: Display portion
332: Status display lamp
4: Manual packaging unit
5: Packaging unit
53: Printer
6: Packaging control unit
61: Control portion
62: Storage portion
100: Medicine dispensing apparatus
200: Prescription input terminal
400: Medicine dispensing apparatus
S1, S2 . . . : Procedure (step) number
S11, S12 . . . : Procedure (step) number
S21, S22 . . . : Procedure (step) number
S31, S32 . . . : Procedure (step) number
S41, S42 . . . : Procedure (step) number

What is claimed is:

1. A medicine dispensing apparatus, comprising:
a plurality of medicine cassettes comprising a plurality of specified medicine cassettes for dispensing specified types of medicines and a plurality of unspecified medicine cassettes for dispensing desired types of medicines;
an allocating portion that selects one medicine cassette from the plurality of specified medicine cassettes or from the plurality of unspecified medicine cassettes and allocates medicine information to the one medicine cassette based upon medicine information pertaining to a medicine to be dispensed from the one medicine cassette, wherein the allocating portion allocates medicine information to an unspecified medicine cassette of the plurality of unspecified medicine cassettes if no specified medicine cassette of the plurality of specified medicine cassettes contains medicine corresponding to the medicine to be dispensed from the one medicine cassette; and
a driving control portion configured to drive the one medicine cassette to adjust a driving condition of the one medicine cassette according to a physical characteristic of the medicine corresponding to the medicine information allocated to the one medicine cassette by the allocating portion.

2. The medicine dispensing apparatus according to claim 1, further comprising a driving portion configured to supply driving force to a driving mechanism provided to the one medicine cassette,
wherein the driving control portion controls the driving portion according to a predetermined driving condition.

3. The medicine dispensing apparatus according to claim 1, wherein the allocating portion allocates the medicine information to the one medicine cassette when the medicine information on the medicine to be dispensed is specified in prescription data received by the dispensing apparatus.

4. The medicine dispensing apparatus according to claim 1, further comprising a code reading portion configured to read the medicine information from a one-dimensional code or a two-dimensional code,
wherein the allocating portion allocates the medicine information to the one medicine cassette when the medicine information on the medicine to be dispensed is given through the code reading portion.

5. The medicine dispensing apparatus according to claim 1, further comprising:
a manual distributing portion having a plurality of boxes into which medicines to be packaged are to be respectively supplied in units of packages; and
a manual dispensing portion for selectively dispensing the medicine contained in each of the boxes,
wherein the allocating portion displays a message indicating that the manual distributing portion should be used without carrying out the allocation of the medicine information to the one medicine cassette when the medicine information on the medicine to be dispensed matches predetermined allocation exclusion medicine information.

6. The medicine dispensing apparatus according to claim 1, further comprising:
a manual distributing portion having a plurality of boxes into which medicines to be packaged are respectively supplied; and
a manual dispensing portion for selectively dispensing the medicine contained in each of the boxes,
wherein the allocating portion displays a message indicating that the manual distributing portion should be used without allocation of the medicine information to the one medicine cassette of the plurality of unspecified medicine cassettes if no specified medicine cassette of the plurality of specified medicine cassettes contains medicine corresponding to the medicine information and if the medicine information on the medicine received by the dispensing apparatus matches predetermined allocation exclusion medicine information.

7. The medicine dispensing apparatus according to claim 1, further comprising a driving correspondence information storage portion configured to store driving correspondence information indicating a correspondence relationship between the medicine information and the driving condition,
wherein the driving control portion identifies, on the basis of the driving correspondence information, the driving condition corresponding to the medicine information on the medicine to be dispensed from the one medicine cassette.

8. The medicine dispensing apparatus according to claim 1, further comprising an allocation information storage portion configured to store allocation information indicating an allocation state associated with each medicine cassette of the plurality of medicine cassettes and the medicine information,
wherein, based upon the allocation information, the allocating portion allocates the medicine information on the medicine to be dispensed from a medicine cassette of the plurality of medicine cassettes which has not yet been subjected to the allocation.

9. The medicine dispensing apparatus according to claim 1, further comprising a predetermined driving condition that includes at least one of a prior driving condition related to adjustment of the one medicine cassette before a start of a dispensation of the medicine from the one medicine cassette, an under-driving condition related to driving control during the dispensation of the medicine from one medicine cassette, and a driving stop condition related to a driving control to be performed when the dispensation of the medicine from the one medicine cassette is stopped.

10. The medicine dispensing apparatus according to claim 9, wherein the one medicine cassette has a dispensing portion configured to dispense the medicine from a medicine containing portion in which the medicine is contained, and
wherein the under-driving condition includes a dispensing speed of the medicine to be dispensed by the dispensing portion.

11. The medicine dispensing apparatus according to claim 9, wherein the one medicine cassette has a path adjusting portion configured to change one or both of a height and a width of a discharging path through which the medicine is dispensed from a medicine containing portion in which the medicine is contained, and
wherein the prior driving condition includes one or both of the height and the width of the discharging path.

12. A method of dispensing medicines with a medicine dispensing apparatus including a plurality of medicine cassettes for respectively dispensing desired types of medicines, the method comprising:
allocating medicine information to one medicine cassette of the plurality of medicine cassettes pertaining to medicine to be dispensed from the one medicine cassette when the medicine information is received by the medicine dispensing apparatus, wherein the plurality of medicine cassettes comprises a plurality of specified medicine cassettes and a plurality of unspecified medicine cassettes, and wherein the allocating portion allocates medicine information to an unspecified medicine cassette of the plurality of unspecified medicine cassettes if no specified medicine cassette of the plurality of specified medicine cassettes contains medicine corresponding to the medicine to be dispensed from the one medicine cassette; and
driving the one medicine cassette of the plurality of medicine cassettes to adjust a driving condition of the one medicine cassette according to a physical characteristic of the medicine corresponding to the medicine information allocated to the one medicine cassette.

13. A non-transitory computer-readable storage medium storing a medicine dispensing program for allowing a computer to execute a method of dispensing a medicine, the method comprising:
allocating medicine information to one medicine cassette of the plurality of medicine cassettes pertaining to medicine to be dispensed from the one medicine cassette when the medicine information is received by the medicine dispensing apparatus, wherein the plurality of medicine cassettes comprises a plurality of specified medicine cassettes and a plurality of unspecified medicine cassettes, and wherein the allocating portion allocates medicine information to an unspecified medicine cassette of the plurality of unspecified medicine cassettes if no specified medicine cassette of the plurality of specified medicine cassettes contains medicine corresponding to the medicine to be dispensed from the one medicine cassette; and driving the one medicine cassette of the plurality of medicine cassettes to adjust a driving condition of the one medicine cassette according to a physical characteristic of the medicine corresponding to the medicine information allocated to the one medicine cassette.

\* \* \* \* \*